(12) United States Patent
Naranjo-Briceño et al.

(10) Patent No.: US 11,993,068 B2
(45) Date of Patent: May 28, 2024

(54) MYCOTEXTILES INCLUDING ACTIVATED SCAFFOLDS AND NANO-PARTICLE CROSS-LINKERS AND METHODS OF MAKING THEM

(71) Applicant: Spora Cayman Holdings Limited, Vitacura (CL)

(72) Inventors: Leopoldo Naranjo-Briceño, O'Higgins Region (CL); Keyla M. Fuentes, O'Higgins Region (CL); Stalin A. Bermúdez-Puga, O'Higgins Region (CL); Hernán Rebolledo, O'Higgins Region (CL); José Miguel Figueroa, O'Higgins Region (CL); Pablo Zamora, O'Higgins Region (CL)

(73) Assignee: Spora Cayman Holdings Limited, Vitacura (CL)

( * ) Notice: Subject to any disclaimer, the term of this patent is extended or adjusted under 35 U.S.C. 154(b) by 0 days.

(21) Appl. No.: 18/301,203

(22) Filed: Apr. 14, 2023

(65) Prior Publication Data
US 2023/0356501 A1    Nov. 9, 2023

Related U.S. Application Data

(60) Provisional application No. 63/331,734, filed on Apr. 15, 2022.

(51) Int. Cl.
B32B 9/02    (2006.01)
B32B 5/02    (2006.01)
(Continued)

(52) U.S. Cl.
CPC .................. *B32B 9/02* (2013.01); *B32B 5/02* (2013.01); *B32B 7/02* (2013.01); *B32B 9/045* (2013.01);
(Continued)

(58) Field of Classification Search
CPC ..... Y10T 428/24273; Y10T 428/24298; Y10T 428/24322; Y10T 428/24331;
(Continued)

(56) References Cited

U.S. PATENT DOCUMENTS 4,125,708 A * 11/1978 Masri ...................... B01J 20/24
                                                          521/40.5
5,486,474 A    1/1996 Bradley et al.
(Continued)

FOREIGN PATENT DOCUMENTS

AU         212399 A     5/1999
AU     2013251269 B2   10/2015
(Continued)

OTHER PUBLICATIONS

Machine translation (Espacenet) of JP 2006-124267 A. Translated Aug. 12, 2023. (Year: 2023).*
(Continued)

*Primary Examiner* — Maria V Ewald
*Assistant Examiner* — Ethan A. Utt
(74) *Attorney, Agent, or Firm* — Shay Glenn LLP

(57) ABSTRACT

Mycotextiles, methods of making them, methods of processing them, and compositions and apparatuses for making and/or processing them are described herein.

25 Claims, 36 Drawing Sheets

(51) Int. Cl.
- *B32B 7/02* (2019.01)
- *B32B 9/04* (2006.01)
- *B32B 27/22* (2006.01)
- *C12N 1/14* (2006.01)

(52) U.S. Cl.
CPC .............. *B32B 9/047* (2013.01); *B32B 27/22* (2013.01); *C12N 1/14* (2013.01); *B32B 2250/40* (2013.01); *B32B 2262/0261* (2013.01); *B32B 2262/101* (2013.01); *B32B 2262/106* (2013.01); *B32B 2264/062* (2013.01); *B32B 2264/105* (2013.01); *B32B 2264/107* (2013.01); *B32B 2264/108* (2013.01); *B32B 2264/401* (2020.08); *B32B 2264/402* (2020.08); *B32B 2307/54* (2013.01); *B32B 2307/7163* (2013.01); *B32B 2307/7246* (2013.01)

(58) Field of Classification Search
CPC .............. Y10T 428/25; Y10T 428/252; Y10T 428/254; Y10T 428/256; Y10T 428/257; Y10T 428/259; Y10T 428/29; Y10T 428/2982; Y10T 428/2991; Y10T 428/2993; Y10T 428/2995; Y10T 428/2998; Y10T 428/31725; Y10T 428/31971; Y10S 428/904; Y10S 977/773; Y10S 977/775; Y10S 977/776; Y10S 977/777; Y10S 977/778; Y10S 977/779; Y10S 977/783; Y10S 977/788; Y10S 977/81; Y10S 977/811; Y10S 977/831; Y10S 977/84; Y10S 977/894; Y10S 977/902; B32B 5/00; B32B 5/16; B32B 5/22; B32B 5/30; B32B 9/00; B32B 9/02; B32B 9/025; B32B 9/04; B32B 9/047; B32B 2317/00; B32B 2317/08; B32B 2317/10; B32B 2317/18; D06N 3/00; D06N 3/0002; D06N 3/0006; D06N 3/0009; D06N 3/0015; D06N 3/0022; D06N 3/0034
USPC ....... 428/131, 134, 137, 138, 323, 325, 327, 428/328, 329, 331, 357, 402, 403, 404, 428/405, 407, 408, 426, 474.4, 532, 904; 977/773, 775, 776, 777, 778, 779, 783, 977/788, 810, 811, 831, 840, 894, 902

See application file for complete search history.

(56) References Cited

U.S. PATENT DOCUMENTS

| | | | |
|---|---|---|---|
| 5,583,041 | A | 12/1996 | Bradley et al. |
| 5,939,065 | A | 8/1999 | Bradley et al. |
| 8,227,224 | B2 | 7/2012 | Kalisz et al. |
| 8,227,225 | B2 | 7/2012 | Rocco et al. |
| 8,227,233 | B2 | 7/2012 | Kalisz et al. |
| 8,283,153 | B2 | 10/2012 | Rocco et al. |
| 8,298,809 | B2 | 10/2012 | Kalisz et al. |
| 8,298,810 | B2 | 10/2012 | Rocco et al. |
| 9,485,917 | B2 | 11/2016 | Bayer et al. |
| 9,555,395 | B2 | 1/2017 | Araldi et al. |
| 9,714,180 | B2 | 7/2017 | McIntyre et al. |
| 10,537,070 | B2 | 1/2020 | Betts et al. |
| 10,687,482 | B2 | 6/2020 | Ross et al. |
| 11,015,059 | B2 | 5/2021 | Smith et al. |
| 2009/0307969 | A1 | 12/2009 | Bayer et al. |
| 2010/0218878 | A1 | 9/2010 | Wang et al. |
| 2011/0306107 | A1 | 12/2011 | Kalisz et al. |
| 2012/0135504 | A1 | 5/2012 | Ross |
| 2012/0227899 | A1 | 9/2012 | McIntyre et al. |
| 2013/0263500 | A1 | 10/2013 | McIntyre et al. |
| 2014/0097008 | A1 | 4/2014 | Bayer et al. |
| 2014/0120602 | A1 | 5/2014 | Winiski et al. |
| 2015/0247115 | A1 | 9/2015 | Bayer et al. |
| 2015/0293076 | A1 | 10/2015 | Widmaier et al. |
| 2015/0376565 | A1 | 12/2015 | Schaak et al. |
| 2016/0002589 | A1 | 1/2016 | Winiski |
| 2016/0264926 | A1 | 9/2016 | Winiski et al. |
| 2016/0302364 | A1 | 10/2016 | Lucht et al. |
| 2017/0253852 | A1 | 9/2017 | Bayer et al. |
| 2018/0216260 | A1 | 8/2018 | Breslauer et al. |
| 2018/0282381 | A1 | 10/2018 | Kittleson et al. |
| 2018/0282937 | A1 | 10/2018 | Bainbridge et al. |
| 2019/0169242 | A1 | 6/2019 | Boulet-Audet et al. |
| 2019/0338240 | A1 | 11/2019 | Carlton et al. |
| 2019/0359931 | A1 | 11/2019 | Mueller et al. |
| 2019/0389916 | A1 | 12/2019 | Rice et al. |
| 2019/0390156 | A1 | 12/2019 | Bayer et al. |
| 2020/0022451 | A1 | 1/2020 | Smith et al. |
| 2020/0024577 | A1 | 1/2020 | Carlton et al. |
| 2020/0025672 | A1 | 1/2020 | Scullin et al. |
| 2020/0032434 | A1 | 1/2020 | Resneck et al. |
| 2020/0102429 | A1 | 4/2020 | Smith et al. |
| 2020/0131694 | A1 | 4/2020 | Scullin et al. |
| 2020/0196541 | A1 | 6/2020 | Ross et al. |
| 2020/0239830 | A1 | 7/2020 | O'Brien et al. |
| 2020/0268031 | A1 | 8/2020 | Macur et al. |
| 2020/0283750 | A1 | 9/2020 | Gamboa et al. |
| 2020/0362295 | A1 | 11/2020 | Kozubal et al. |
| 2020/0392341 | A1 * | 12/2020 | Smith ................... C08L 31/04 |
| 2020/0399328 | A1 | 12/2020 | Breslauer et al. |
| 2020/0399824 | A1 * | 12/2020 | Stewart ................ D06M 13/148 |
| 2021/0059287 | A1 | 3/2021 | Kozubal et al. |
| 2021/0171896 | A1 | 6/2021 | Harney et al. |
| 2021/0317433 | A9 | 10/2021 | Schaak |
| 2021/0388558 | A1 | 12/2021 | Stewart et al. |

FOREIGN PATENT DOCUMENTS

| | | | | |
|---|---|---|---|---|
| AU | 2019201553 | A1 | 3/2019 | |
| AU | 2019219768 | A1 | 9/2019 | |
| AU | 2020201013 | A1 | 9/2020 | |
| BR | 102013028238 | B1 | 3/2021 | |
| CN | 103171823 | A | 6/2013 | |
| CN | 108503858 | A | 9/2018 | |
| IN | 201921004709 | A | 5/2019 | |
| JP | 2006124267 | A * | 5/2006 | |
| JP | 5131676 | B2 | 1/2013 | |
| KR | 20150014560 | A | 2/2015 | |
| WO | WO92/13960 | A1 | 8/1992 | |
| WO | WO95/010597 | A1 | 4/1995 | |
| WO | WO97/023416 | A1 | 7/1997 | |
| WO | WO2008/118543 | A2 | 10/2008 | |
| WO | WO2010/005476 | A1 | 1/2010 | |
| WO | WO2012/148995 | A1 | 11/2012 | |
| WO | WO2014/031810 | A2 | 2/2014 | |
| WO | WO2015/042164 | A2 | 3/2015 | |
| WO | WO2016/073453 | A1 | 5/2016 | |
| WO | WO2016/168563 | A1 | 10/2016 | |
| WO | WO-2017093759 | A1 * | 6/2017 | .............. B60C 1/00 |
| WO | WO2018/014004 | A1 | 1/2018 | |
| WO | WO2018/053204 | A1 | 3/2018 | |
| WO | WO2018/132821 | A2 | 7/2018 | |
| WO | WO2018183735 | A1 | 10/2018 | |
| WO | WO2019/046480 | A1 | 3/2019 | |
| WO | WO2019/060921 | A1 | 3/2019 | |
| WO | WO2019/099474 | A1 | 5/2019 | |
| WO | WO2019/178406 | A1 | 9/2019 | |
| WO | WO2019/222633 | | 11/2019 | |
| WO | WO2019/226823 | A1 | 11/2019 | |
| WO | WO2020/006133 | A1 | 1/2020 | |
| WO | WO2020/033970 | A2 | 2/2020 | |
| WO | WO2020/072140 | A1 | 4/2020 | |
| WO | WO2020/086907 | A1 | 4/2020 | |
| WO | WO2020/087033 | A1 | 4/2020 | |
| WO | WO2020/102552 | A1 | 5/2020 | |
| WO | WO2020/106743 | A1 | 5/2020 | |
| WO | WO2020/112742 | A1 | 6/2020 | |
| WO | WO2020/115690 | A1 | 6/2020 | |
| WO | WO2020/176758 | A1 | 9/2020 | |

(56) References Cited

FOREIGN PATENT DOCUMENTS

| WO | WO2020/186068 A1 | 9/2020 |
| WO | WO2020/237201 A1 | 11/2020 |
| WO | WO2020/243431 A1 | 12/2020 |
| WO | WO2021/011431 A1 | 1/2021 |
| WO | WO2021/035184 A1 | 2/2021 |
| WO | WO2021/055440 A1 | 3/2021 |
| WO | WO2021/092051 A1 | 5/2021 |
| WO | WO2021/124164 A1 | 6/2021 |
| WO | WO2021/136883 A1 | 7/2021 |

OTHER PUBLICATIONS

Deeg et al.; Greener Solutions: Improving performance of mycelium-based leather; Final Report to MycoWorks; pp. 1-54; 2017.

Wijayarathna et al.; Fungal textile alternatives from bread waste with leather-like properties; Resources, Conservation and Recycling; 179:106041; Apr. 1, 2022.

Genbank JN164989.1; Trametes cubensis voucher CRM90 18S ribosomal RNA gene, partial sequence; internal transcribed spacer 1, 5.8S ribosomal RNA gene, and internal transcribed spacer 2, complete sequence; and 28S ribosomal RNA gene, partial sequence; 1 page; retrived from the internet ( https://www.ncbi.nim.nih.gov/nuccore/JN164989.1) on May 22, 2023.

Genbank JX416577.1; *Basidiomycota* sp. FPF38a internal trascribed spacer 1, partial sequence; 5.8S ribosomal RNA gene, complete sequence; and internal transcribed spacer 2, partial sequence; 2 pages; retrieved from the internet (hhttps://www.ncbi.nlm.nih.gov/nuccore/JX416577.1) on May 22, 2023.

Genbank KX515895.1; Uncultured fungus clone ZMTDH201308-27 small subunit ribosomal RNA gene, partial sequence; internal transcribed spacer 1, 5.8S ribosomal RNA gene, and internal transcribed spacer 2, complete sequence; and large subunit ribosomal RNA gene, partial sequence; 1 page; retrieved from the internet (https://www.ncbi.nim.nih.gov/nuccore/1121643866) on May 22, 2023.

Nam et al.; Role of phosphate-modified mesoporous silica nanoparticles for altering biomimetic metal-induced aggregation process of pluronic F127 block copolymer. Materials Letters; vol. 110, pp. 176-179, Aug. 13, 2013.

Sojka-Ledakowicz et al.; Functionalization of textile materials by alkoxysilane-grafted titanium dioxide; Journal of materials science; vol. 44, pp. 3852-3860; May 15, 2009.

* cited by examiner

| Nomenclature in the Fungal Stock Center of Spora Biotech[1] | Order | Family | Genera | Species | Fruiting body / morphotype |
|---|---|---|---|---|---|
| 0001/280121/ET/BF | Auriculariales | Auriculariaceae | *Auricularia* | *fuscosuccinea* | 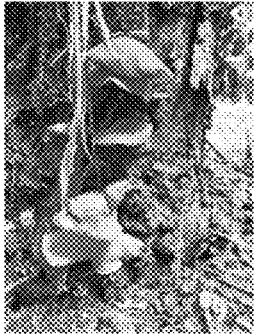 |
| 0002/280121/ET/BF | Polyporales | Polyporaceae | UC | UC | 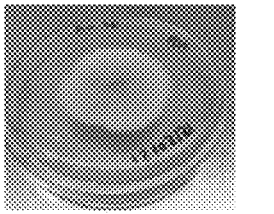 |
FIG. 2A

| | | | | | |
|---|---|---|---|---|---|
| 0006/010221/SS/BF | Polyporales | Polyporaceae | UC | UC | 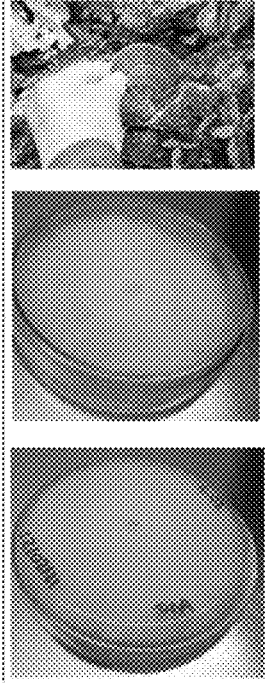 |
| 0007/010221/SS/BF | Polyporales | Ganodermataceae | UC | UC | 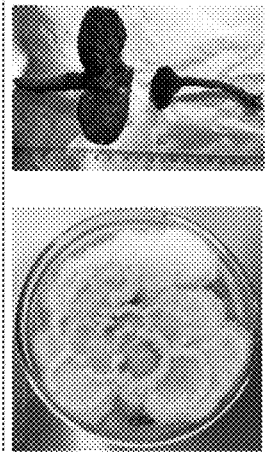 |
FIG. 2B

| | | | | |
|---|---|---|---|---|
| 0011/010221/S S/BF | Xylariales | Xylariaceae | *Xylaria* | *apiculata* |
| 0013/010221/S S/BF | Polyporales | Polyporaceae | *Lentinus* | UC |

FIG. 2C

| | | | | | |
|---|---|---|---|---|---|
| 0014/010221/S5/BF | Polyporales | Polyporaceae | UC | UC | 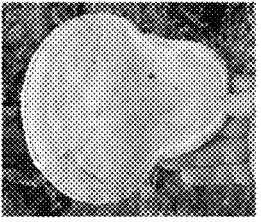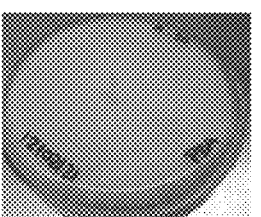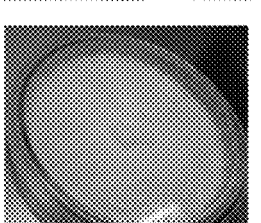 |
| 0018/020221/SM/EW | UC | UC | UC | UC | 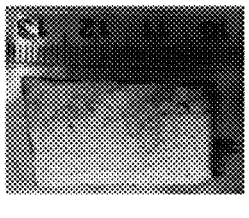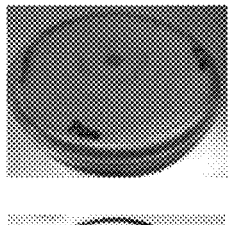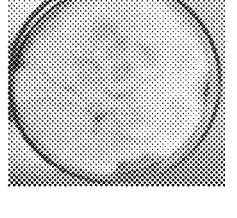 |
FIG. 2D

| | | | | |
|---|---|---|---|---|
| 0020/020221/S M/8F | Xylariales | Xylariaceae | Xylaria | berteri |
| 0021/020221/S M/8F | UC | UC | UC | UC |

FIG. 2E

| | | | | | |
|---|---|---|---|---|---|
| 0023/020221/SM/BF | Polyporales | Polyporaceae | UC | UC | 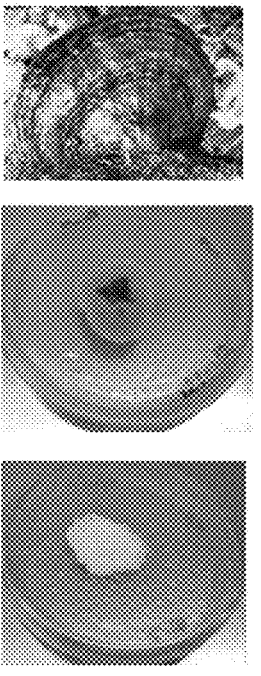 |
| 0026/020221/SM/BF | UC | UC | UC | UC | 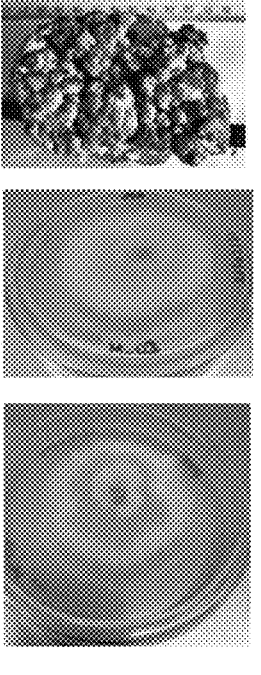 |
FIG. 2F

| 0028/020221/S M/BF | Polyporales | Polyporaceae | UC | UC | 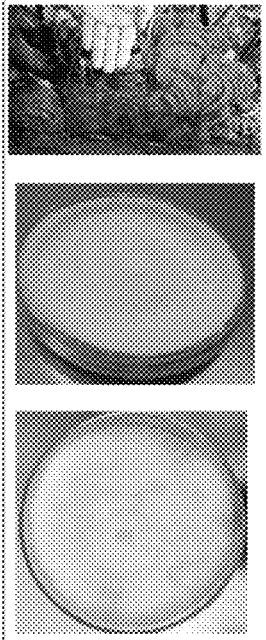 |
| 0031/060221/H M/BF | Polyporales | Polyporaceae | *Pycnoporus* | *sanguineus* | 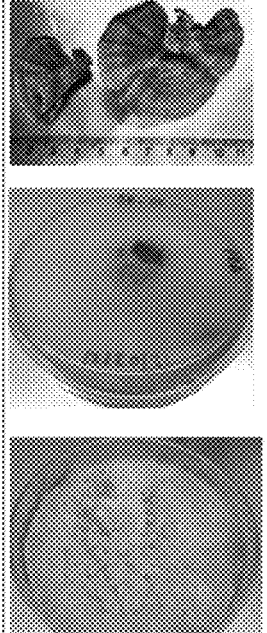 |
FIG. 2G

| | | | | | |
|---|---|---|---|---|---|
| 0037/010320/SS/BF | Polyporales | Polyporaceae | UC | UC | |
| 0038/010320/SS/BF | Polyporales | Polyporaceae | UC | UC | |

FIG. 2H

| | | | | | |
|---|---|---|---|---|---|
| 0039/010321/SS/BF | Polyporales | Polyporaceae | UC | UC | 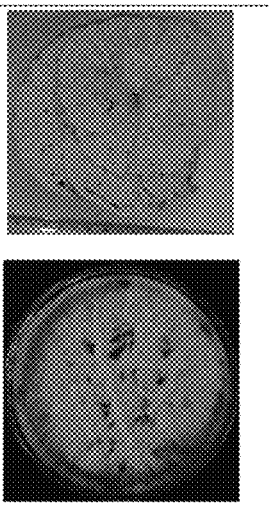 |
| 0040/120621/CU/BF | Polyporales | Polyporaceae | Earliella | scabrosa | 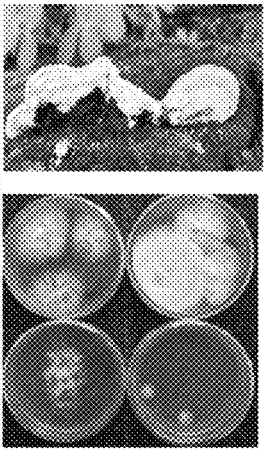 |
| 0042/120621/CU/BF | Polyporales | Panaceae | Panus | UC | 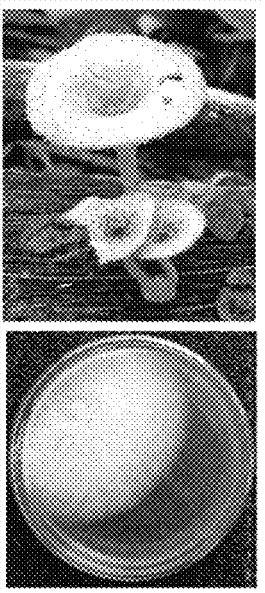 |
FIG. 2I

| | | | | | |
|---|---|---|---|---|---|
| 0045/120621/CU/MY | Xylariales | Xylariaceae | *Hypoxylon* | UC | |
| 0046/120621/CU/BF | Polyporales | Polyporaceae | *Polyporus* | UC | |

FIG. 2J

| | | | | |
|---|---|---|---|---|
| 0047/120621/C U/BF | Xylariales | UC | UC | UC  |
| 0048/120621/C U/BF | Xylariales | Xylariaceae | *Xylaria* | *multiplex* 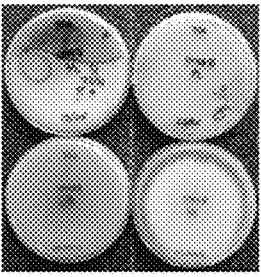 |
| 0049/042021/S T/BF | Agaricales | Hymenogastraceae | *Psilocybe* | UC 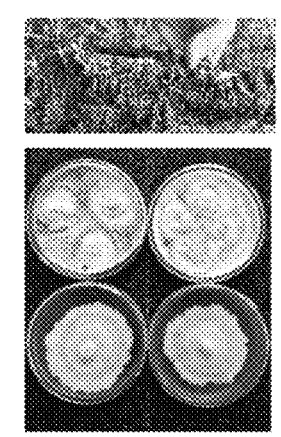 |
FIG. 2K

| Nomenclature FSC¹ Spora Biotech | GenBank Database² | | | | Fungene Database³ | | UNITE Community Database⁴ | | GenBank Accession Number | Taxon Name |
|---|---|---|---|---|---|---|---|---|---|---|
| | Query Cover (%) | E-value | Per Identity (%) | Taxa matched GenBank Accession Number | Score (Bits) | Taxa matched GenBank Accession Number | Score (Bits) | Taxa matched UNITE Species Hypothesis code | | |
| 0000/010120/CH/VM | 100 | 0.0 | 98.62 | Ganoderma lucidum strain ATCC 64251 JQ520182.1 | 1084 | Ganoderma lucidum voucher HMAS86599 | 1121 | Ganoderma sichuanense SH1129801.08FU | OM367922 | Ganoderma lucidum |
| 0001/280121/ET/BF | 100 | 0.0 | 99.36 | Auricularia fuscosuccinea isolate TFB11532 JX046350.1 | - | - | 1198 | Auricularia scissa SH1183178.08FU | OM367923 | Auricularia fuscosuccinea |
| 0002/280121/ET/BF | 99 | 0.0 | 99.85 | Leiotrametes menziesii strain CIRM-BRFM 1781 OL685332.1 | 1181 | Trametes cubensis voucher CIRM30 JN164989.1 | 1198 | Trametes cubensis SH1186669.08FU | OM367924 | Polyporaceae Unclassified |
| 0006/010221/SS/BF | 100 | 0.0 | 100 | Leiotrametes menziesii strain CIRM-BRFM 1781 OL685332.1 | 1181 | Trametes cubensis voucher CIRM30 JN164989.1 | 1198 | Trametes cubensis SH1186669.08FU | OM367925 | Polyporaceae Unclassified aff. Leiotrametes genera |
| 0011/010221/SS/BF | 100 | 0.0 | 99.84 | Xylaria apiculata isolate 942 KP133330.1 | - | - | 1127 | Xylaria apiculata SH1370190.08FU | OM367926 | Xylaria apiculata |
| 0013/010221/SS/BF | 100 | 0.0 | 93.04 | Lentinus crinitus strain DPUA1693 MH915578.1 | 973 | Lentinus scleropus isolate TFB1104 GU207310.1 | 1117 | Lentinus striatulus SH1180314.08FU | OM367927 | Lentinus sp. |
| 0014/010221/SS/BF | 99 | 0.0 | 99.71 | Leiotrametes menziesii strain CIRM-BRFM 1781 OL685332.1 | 1181 | Trametes cubensis voucher CIRM30 JN164989.1 | 1206 | Trametes cubensis SH1186669.08FU | OM367928 | Polyporaceae Unclassified aff. Leiotrametes genera |
| 0020/020221/SM/BF | 100 | 0.0 | 99.34 | Xylaria berteri isolate B10 KP133344.1 | - | - | 1075 | Xylaria ellisii SH1370193.08FU | OM367929 | Xylaria berteri |
| 0023/020221/SM/BF | 99 | 0.0 | 99.54 | Uncultured fungus clone ZMTOH201308-27 KX515896.1 | 1086 | Trechispora spinulifera strain CBS 383.61 FJ711051.1 | 1161 | Fungi (Agaricomycetes) SH1128807.08FU | OM367930 | Polyporaceae Unclassified |
| 0028/020221/SM/BF | 100 | 0.0 | 99.85 | Leiotrametes menziesii strain CIRM-BRFM 1781 OL685332.1 | 1181 | Trametes cubensis voucher CIRM30 JN164989.1 | 1198 | Trametes cubensis SH1186669.08FU | OM367931 | Polyporaceae Unclassified |
| 0037/010320/SS/BF (G1) | 99 | 0.0 | 99.23 | Uncultured fungus clone ZMTOH201308-13 KX515881.1 | 1104 | Trechispora spinulifera strain CBS 383.61 FJ711051.1 | 1148 | Fungi (Agaricomycetes) SH1179607.08FU | OM367932 | Polyporaceae Unclassified |
| 0040/120621/CU/BF | 100 | 0.0 | 100 | Earliella scabrosa strain CIRM-BRFM 1817 OL685338.1 | 1219 | Earliella scabrosa strain MUCL 46097 FJ711056.1 | 1180 | Earliella scabrosa SH1130298.08FU | OM367933 | Earliella scabrosa |
| 0042/120621/CU/BF | 95 | 0.0 | 99.84 | Panus strigellus voucher MIBF208 MT089137.1 | 842 | Panus conchatus voucher JM143 KM267730.1 | 1181 | Panus strigellus SH1177601.08FU | OM367934 | Panus sp. |
| 0045/120621/CU/MY | 97 | 0.0 | 99.24 | Hypoxylon investiens strain CBS 129034 MH866184.1 | - | - | 1131 | Hypoxylon investiens SH1213419.08FU | OM367935 | Hypoxylon sp. |
| 0046/120621/CU/BF | 99 | 0.0 | 99.1 | Polyporus sp. isolate SA23 OK393674.1 | 914 | Polyporus nicholsonii CuTFRM11241.SR.10 AFS16542.1 | 1131 | Polyporus thailandensis SH1198306.08FU | OM367936 | Polyporus sp. |
| 0047/120621/CU/BF | 90 | 0.0 | 99.32 | Xylariales sp. isolate BP0069 MW045878.1 | - | - | 1125 | Hypoxylon SH1213413.08FU | OM367937 | Xylariales |

FIG. 4A

| Nomenclature FSC¹ Spora Biotech | GenBank Database² | | | | Fungene Database³ | | UNITE Community Database⁴ | | GenBank Accession Number | Taxon Name |
|---|---|---|---|---|---|---|---|---|---|---|
| | Query Cover (%) | E-value | Per. Identity (%) | Taxa matched GenBank Accession Number | Score (Bits) | Taxa matched GenBank Accession Number | Score (Bits) | Taxa matched UNITE species Hypothesis code | | |
| 0048/120621/CU/8F | 99 | 0.0 | 98.56 | *Xylaria multiplex* strain DSM 110363 MN833801.1 | - | - | 1080 | *Xylaria multiplex* SH1178117.08FU | OM367938 | *Xylaria multiplex* |

¹ Fungal Stock Center of Spora Biotech
² GenBank Database (https://blast.ncbi.nlm.nih.gov/Blast.cgi)
³ Fungene Database (http://www.fungene-db.org)
⁴ UNITE Community Reference Sequence Database (https://unite.ut.ee).

FIG. 4B

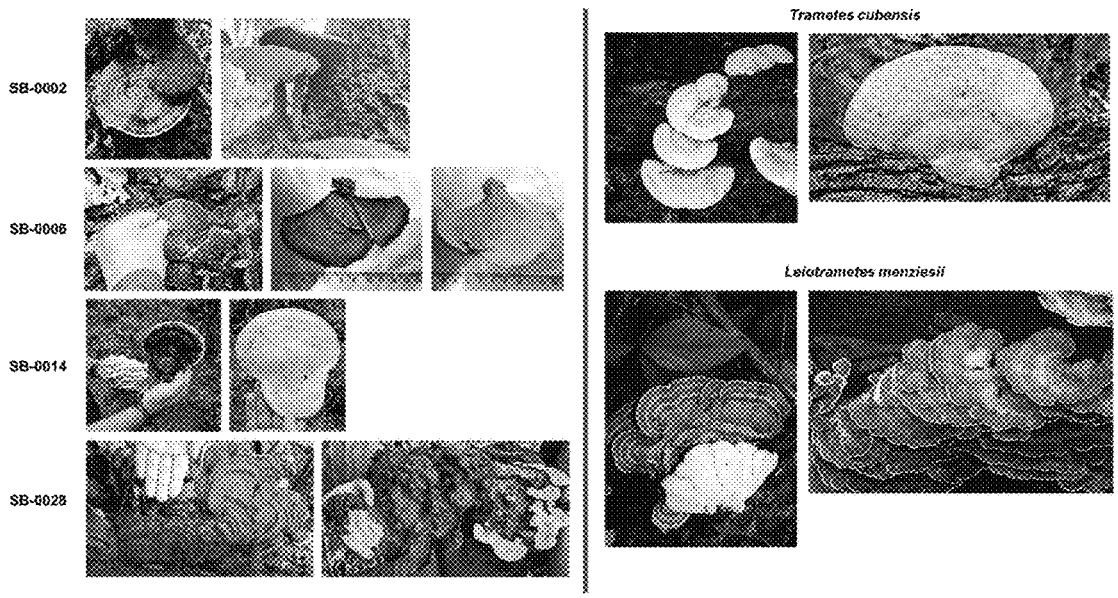

FIG. 4C

| Nomenclature | Cultivation medium | Photograph |
|---|---|---|
| 0000/010120/CH/VM | Sabouraud (SB) | |
| 0002/280121/ET/BF | Sabouraud (SB) | |
| 0006/010221/SS/BF | Sabouraud (SB) | |
| 0013/010221/SS/BF | Sabouraud (SB) | |
| 0014/010221/SS/BF | Sabouraud (SB) | |
| 0023/020221/SM/BF | Sabouraud (SB) | |

FIG. 5A

| | | |
|---|---|---|
| 0028/020221/SM/BF | Sabouraud (SB) | 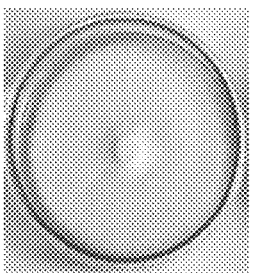 |
| 0037/010320/SS/BF | Sabouraud (SB) | 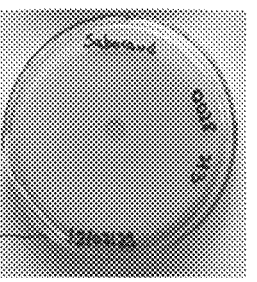 |
| 0046/120621/CU/BF | Sabouraud (SB) | 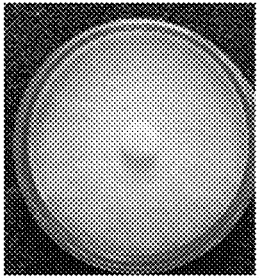 |
FIG. 5B

| Strain | Antibiotics pool | Concentration (μg/mL) |
|---|---|---|
| 0000/010120/CH/VM | Amoxicillin + Ampicillin | 300 + 300 |
| 0002/280121/ET/BF | | 300 + 300 |
| 0006/010221/SS/BF | | 300 + 300 |
| 0013/010221/SS/BF | | 300 + 300 |
| 0014/010221/SS/BF | | 300 + 300 |
| 0023/020221/SM/BF | | 300 + 300 |
| 0028/020221/SM/BF | | 300 + 300 |
| 0037/010320/SS/BF | | 300 + 300 |
| 0046/120621/CU/BF | | 300 + 300 |

FIG. 6A

| Strain | Antibiotics pool | Concentration (μg/mL) |
|---|---|---|
| 0000/010120/CH/VM | Amoxicillin + Ampicillin + Ciprofloxacin | 300 + 300 + 100 |
| 0002/280121/ET/BF | | 300 + 300 + 100 |
| 0006/010221/SS/BF | | 300 + 300 + 100 |
| 0013/010221/SS/BF | | 300 + 300 + 100 |
| 0014/010221/SS/BF | | 300 + 300 + 100 |
| 0023/020221/SM/BF | | 300 + 300 + 100 |
| 0028/020221/SM/BF | | 300 + 300 + 100 |
| 0037/010320/SS/BF | | 300 + 300 + 100 |
| 0046/120621/CU/BF | | 300 + 300 + 100 |

FIG. 6B

| Nomenclature | Medium supplemented with enzyme machinery inducers | Percentage of growth[1] (%) |
|---|---|---|
| 0000/010120/CH/VM | SB + T/M | 100.00 |
| 0002/280121/ET/BF | A/T/M | 77.73 |
| 0006/010221/SS/BF | M | 90.00 |
| 0013/010221/SS/BF | N.D. | N.D. |
| 0014/010221/SS/BF | T/M | 96.00 |
| 0023/020221/SM/BF | N.D. | N.D. |
| 0028/020221/SM/BF | T/M | 95.80 |
| 0037/010320/SS/BF | N.D. | N.D. |
| 0046/120621/CU/BF | M | 75.50 |

[1] Radial growth at 6 days of incubation

FIG. 7

| Nomenclature | mannoproteins and oligosaccharides (%) | (1-3)-D-glucans (%) | (1-6)-β-D-glucans + Chitin (%) | Hyphae diameter (μm) | Tolerance to citric acid (%) | Tolerance to sodium polyphosphate (%) |
|---|---|---|---|---|---|---|
| 0000/010120/CH/VM | 13.3 | 47.4 | 41.5 | 0.9 ± 0.3 | 2 | 2 |
| 0002/280121/ET/BF | 15.0 | 17.4 | 74.2 | 1.3 ± 0.4 | 2 | 2 |
| 0006/010221/SS/BF | 18.4 | 36.7 | 46.1 | 1.4 ± 0.5 | 2 | 2 |
| 0013/010221/SS/BF | 25.8 | 1.6 | 79.9 | NA | 2 | 2 |
| 0014/010221/SS/BF | 33.1 | 15.7 | 49.7 | 1.4 ± 0.4 | 2 | 2 |
| 0023/020221/SM/BF | 25.0 | 21.8 | 51.3 | NA | 2 | <2 |
| 0028/020221/SM/BF | 17.2 | 2.1 | 75.2 | NA | 2 | 2 |
| 0037/010320/SS/BF | 11.4 | 38.4 | 57.6 | 1.6 ± 0.5 | 2 | 2 |
| 0046/120621/CU/BF | 29.1 | 15.1 | 56.8 | 1.0 ± 0.3 | 2 | 2 |
| 0047/120621/CU/B | 15.7 | 21.1 | 78.3 | NA | 2 | <0 |

NA = not applicable

FIG. 13

| Nomenclature | Grain | Colonization %[1] |
|---|---|---|
| 0000/010120/CH/VM | Corn / Wheat | 100 |
| 0002/280121/ET/BF | Corn / Wheat | 100 |
| 0006/010221/SS/BF | Corn / Wheat | 100 |
| 0013/010221/SS/BF | Corn / Wheat | 100 |
| 0014/010221/SS/BF | Corn / Wheat | 100 |
| 0023/020221/SM/BF | Corn / Wheat | 100 |
| 0028/020221/SM/BF | Corn / Wheat | 100 |
| 0037/010320/SS/BF | Corn / Wheat | 100 |
| 0046/120621/CU/BF | Corn / Wheat | 100 |
| 0047/120621/CU/B | Corn / Wheat | 100 |

FIG. 14

| Strain | Mass plate used for inoculation | PDB after 7 days of incubation | Growth kinetics | Homogeneity of colonization | Comments |
|---|---|---|---|---|---|
| 0002/280121/ ET/BF | 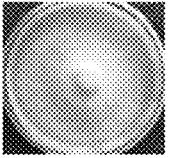 |  | ++ | ++ | - Mycelial growth on inoculated disc and in balls.<br>- Harvested on day 10<br>- There was no color change in the liquid medium |
| 0006/010221/ SS/BF | 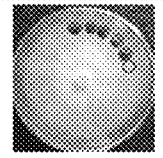 |  | ++++ | ++++ | - The PDB medium changed color due to the homogeneity of the colonization.<br>- Harvested on day 8 |
| 0013/010221/ SS/BF | 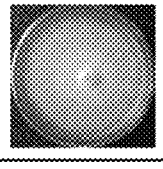 |  | +++ | +++ | - The mycelium colonized the medium without forming tangles and changed coloration.<br>- It was harvested on day 5 |
| 0014/010221/ SS/BF | 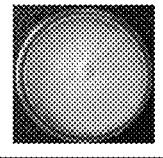 | 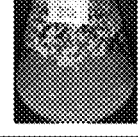 | ++++ | +++ | - The medium changed color due to the homogeneity of the colonization.<br>- It was harvested on day 5 |
| 0023/020221/ SM/BF | 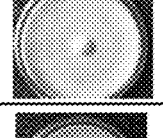 |  | +++ | +++ | - Colonization in the form of balls<br>- It was harvested on day 5 |
| 0028/020221/ SM/BF | 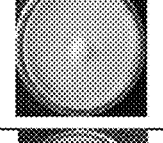 |  | +++ | +++ | - Homogeneous colonization and change of coloration in the medium.<br>- Harvested on day 5. |
| 0037/010320/ SS/BF | 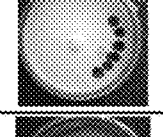 |  | +++ | +++ | - Colonization in the form of balls<br>- Harvested on day 8 |
| 0046/120621/ CU/BF | 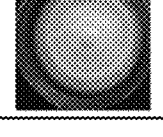 |  | ++ | + | - Slow mycelial growth in the form of tangles<br>- Harvested on day 10 |

FIG. 15

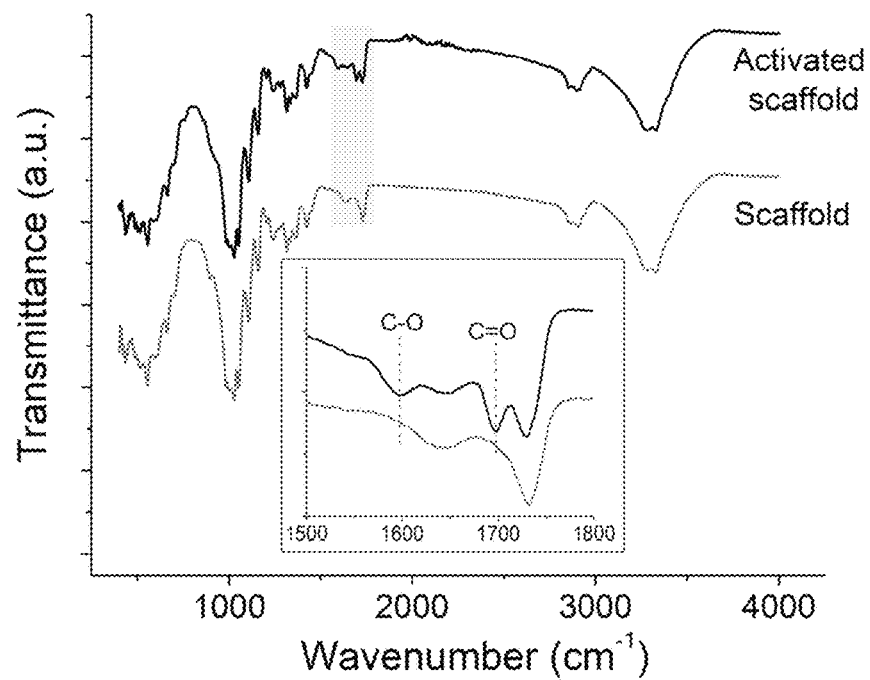
FIG. 18
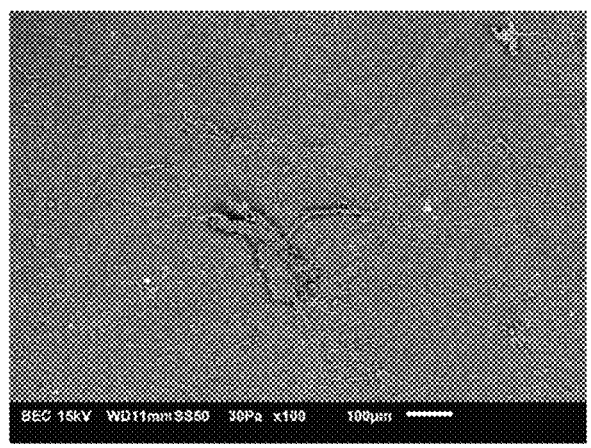 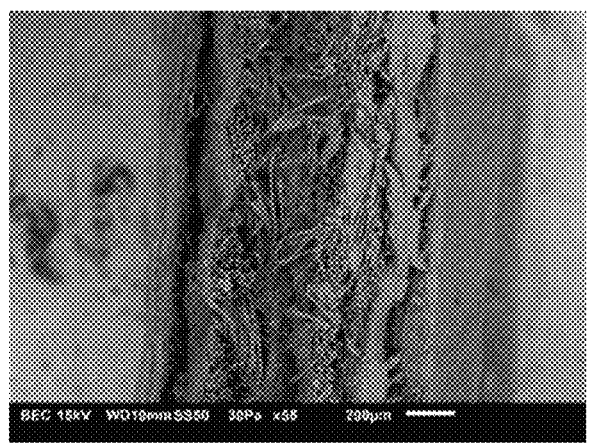
FIG. 19A  FIG. 19B

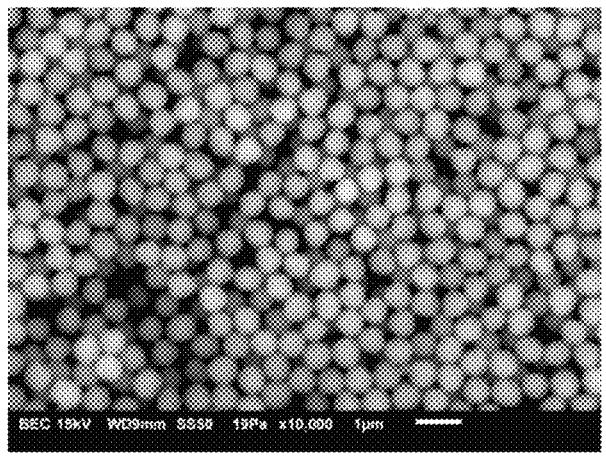
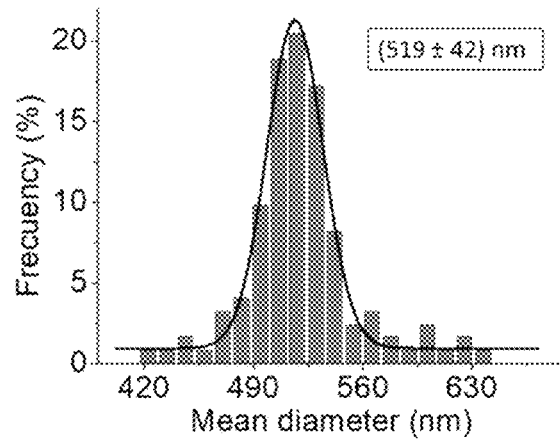
FIG. 22A    FIG. 22B
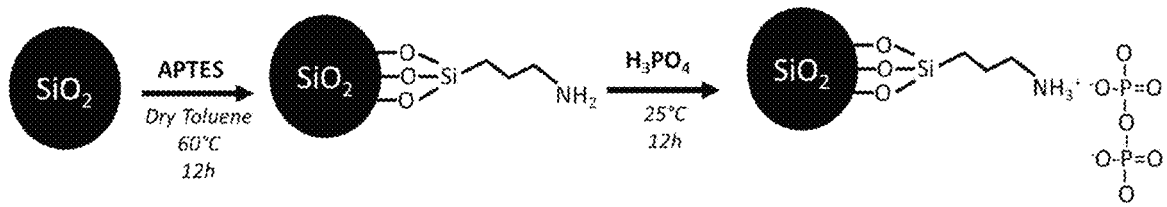
FIG. 23
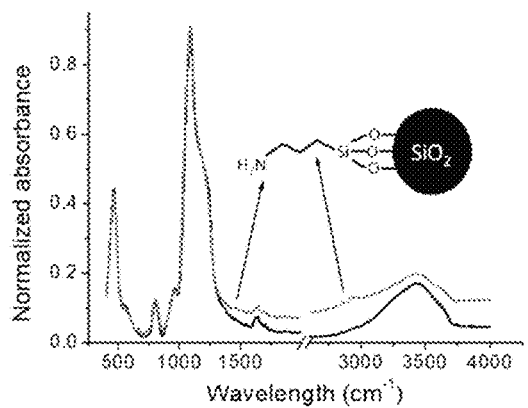
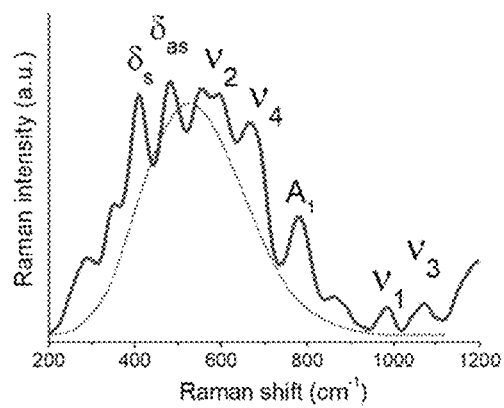
FIG. 24A    FIG. 24B

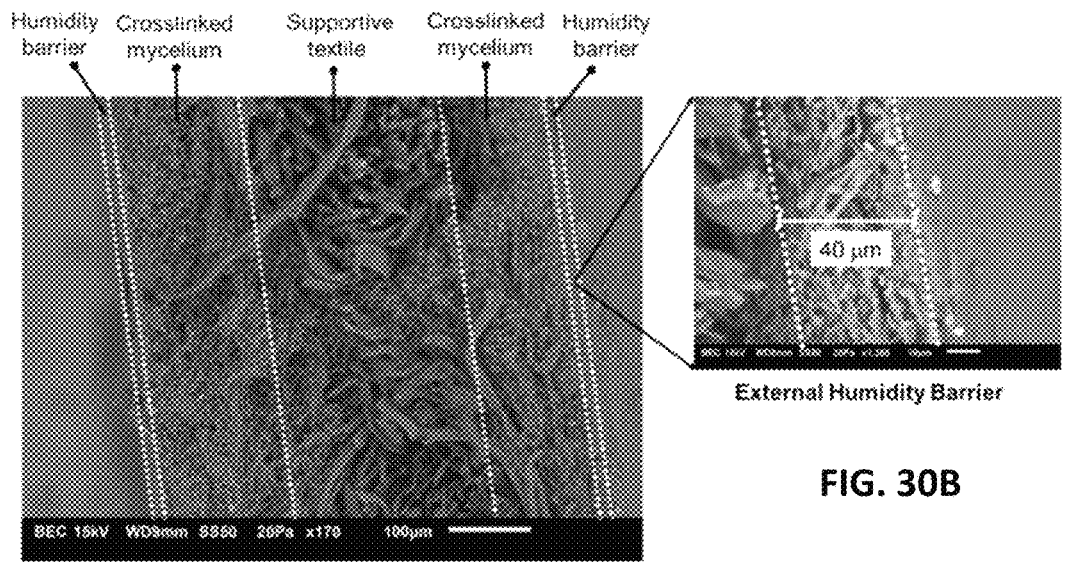
FIG. 30A
FIG. 30B
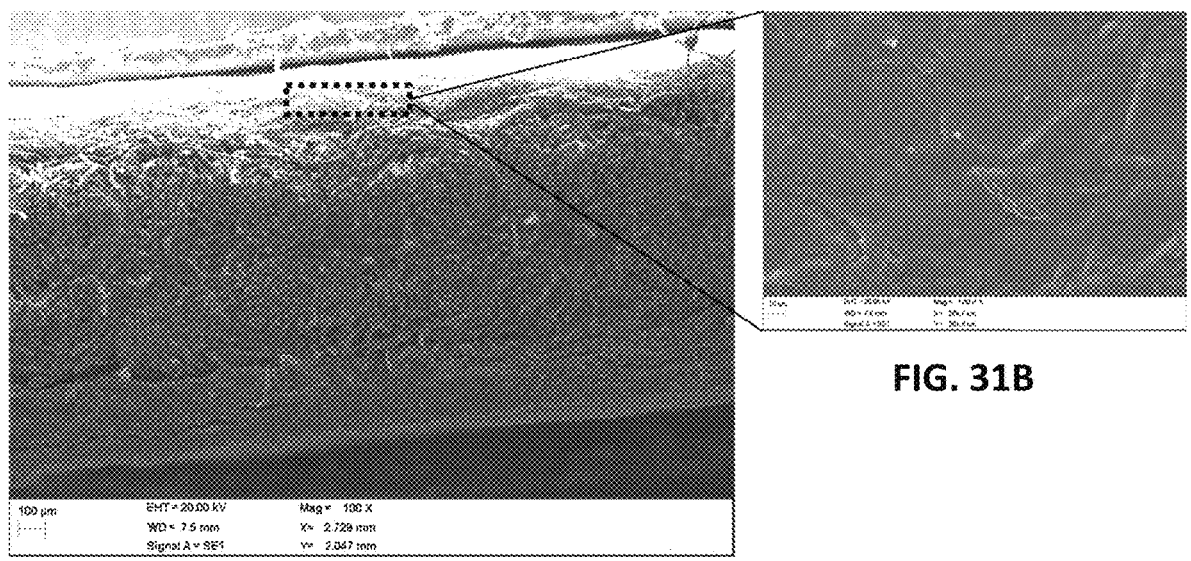
FIG. 31A
FIG. 31B

MYCOTEXTILES INCLUDING ACTIVATED SCAFFOLDS AND NANO-PARTICLE CROSS-LINKERS AND METHODS OF MAKING THEM

CLAIM OF PRIORITY

This patent application claims priority to U.S. Provisional Patent Application No. 63/331,734, titled "MYCOTEXTILES INCLUDING ACTIVATED SCAFFOLDS AND NANO-PARTICLE CROSS-LINKERS AND METHODS OF MAKING THEM," filed on Apr. 15, 2022, and herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Traditional animal-based textile materials, such as leather and synthetic materials, including polymeric materials, create environmental problems during manufacturing, requiring substantial resources, and may also result in significant problems for recycling and disposal of both the textile and the byproducts of manufacture. Mass production of these materials is often associated with negative environmental impacts, both locally and globally since they often involve the generation of toxic and polluting waste and high energy consumption during its production. There is a need for textile materials that may be produced cost-effectively with minimal environmental impact and without animal welfare or other ethical concerns. In particular, there is a need for leather-like materials that have similar or superior physical and/or mechanical properties, e.g., tensile strength, tear strength, flexural rigidity, elasticity, texture, thermal properties, sensory attributes, etc., conventional textile materials, including leather. Described herein are methods and materials that may address these needs.

Although artificial leather material has been previously introduced, including materials based on fungal sources, these materials are less than satisfactory. However, so far, fungal-based leathers (e.g., mycotextiles) have demonstrated relatively poor mechanical characteristics, including abrasion resistance, tearing under low force application, and delamination. What is needed are methods, compositions, and apparatuses for improving mycelium textiles (e.g., mycelium leather) mechanical properties, achieving specific functional and aesthetic properties, quality, durability, and maintaining low margins in production costs.

The methods, compositions, and apparatuses (e.g., materials, such as fabrics) that may address these needs are described herein.

SUMMARY OF THE DISCLOSURE

Described herein are fungal-based textiles (e.g., mycotextiles), methods of making them, methods of processing them, and compositions and apparatuses for making and/or processing them. In general, these fungal-based textiles (which may be referred to herein as mycotextiles) are configured and adapted to be highly durable while resisting tearing and degradation. For example, these mycotextiles may be configured to have high tensile strength, tear resistance, and wear resistance, among other properties. The material may remain supple, e.g., highly flexible, even over extended use, and in various environments, avoiding cracking and peeling.

In some examples, the mycotextiles may include one or more crosslinked mycelium layers, which may be formed of large-diameter hyphae. The material (e.g., fungal strain) used to form the layer may be selected to have properties that enhance the overall appearance and durability of the mycotextile ultimately formed by the fungal strain. In some cases, these properties may be apparent when analyzing the resulting textile, as will be described in detail herein. In general, these mycotextiles may be crosslinked by crosslinking chitin within the cell wall of the hyphae. Thus, described herein are compositions in which this crosslinking is enhanced, through one or more of: the material used (e.g., the shape and/or composition of the mycelium (e.g., hyphae of the mycelium), and/or materials incorporated into the material, including chemically activated support layers/scaffold(s) and, in particular, functionalized nanoparticles.

For example, described herein are mycotextiles that include crosslinking nanoparticles. In some examples, these mycotextiles may include: a support scaffold layer; a first crosslinked mycelium layer extending adjacent to a first side of the support scaffold layer, and a second crosslinked mycelium layer extending adjacent to a second side of the support scaffold layer; and a plurality of nanoparticles within the first and second crosslinked mycelium layers, wherein the plurality of nanoparticles are functionalized to crosslink chitin within hyphae of the first crosslinked mycelium layer and the second crosslinked mycelium layer.

In some examples, the mycotextile includes: a support scaffold layer; a first crosslinked mycelium layer comprising a first hyphal network, wherein hyphae of the first hyphal network have an average diameter of 1 μm or greater, the first crosslinked mycelium layer extending adjacent to a first side of the support scaffold layer; a second crosslinked mycelium layer comprising a second hyphal network, wherein hyphae of the second hyphal network have an average diameter of 1 μm or greater, the second crosslinked mycelium layer extending adjacent to a second side of the support scaffold layer; and a plurality of nanoparticles within the first and second crosslinked mycelium layers, wherein a surface of each nanoparticle of the plurality of nanoparticles is functionalized to crosslink chitin/chitosan within the hyphae of the first crosslinked mycelium layer and the second crosslinked mycelium layer.

A mycotextile may include: a support scaffold layer; a crosslinked mycelium layer extending adjacent to at least a first side of the support scaffold layer; an external humidity barrier on an outer surface of the crosslinked mycelium layer; and a plurality of nanoparticles within the crosslinked mycelium layer, wherein a surface of each nanoparticle of the plurality of nanoparticles are functionalized to crosslink reactive chemical groups within hyphae of the crosslinked mycelium layer.

In any of these mycotextiles, the nanoparticles of the plurality of nanoparticles may have a diameter of between about 60 and 600 nm. The nanoparticles may comprise ceramic nanoparticles, e.g., one or more of: $SiO_2$, $TiO_2$, ZnO, $SnO_2$, $Al_2O_3$, $Fe_2O_3$, and $Fe_3O_4$. The nanoparticles may comprise polymeric nanoparticles, e.g., one or more of: zein, alginate, chitosan, latex, poly(lactide) (PLA), poly (lactide-co-glycolide) (PLGA) copolymers, and poly (ε-caprolactone) (PCL). The nanoparticles may comprise metallic nanoparticles, e.g., one or more of: Au, Ag, Cu, and Pt. The nanoparticles may comprise carbon-based nanostructures, e.g., one or more of: nanofibers, single or multi-walled nanotubes, graphene, and spheres. The nanoparticles may comprise composites among ceramic, polymeric, metallic, and/or carbon-based nanoparticles.

The plurality of nanoparticles may be functionalized nanoparticles. For example, the functionalized nanoparticles may include amino-terminal groups bound to the surface of the nanoparticles, one or more polyphosphate groups, one or more epoxy groups, one or more acrylic groups, one or more isocyanate groups, one or more vinylic groups coupled to the surface of the nanoparticle coupled to the surface of the nanoparticles. In some examples, the plurality of nanoparticles within the crosslinked to hyphae of the first crosslinked mycelium layer may comprise between 0.1% and 5% by weight of the mycotextile.

The average diameter of the hyphae in the first mycelium layer and the second mycelium layer may be greater than about 1 μm. In any of these examples, the chitin fraction ((1-6)-β-D-glucans plus chitin) of the first crosslinked mycelium layer and/or the second crosslinked mycelium layer may be 45 to 80%, and the first crosslinked mycelium layer and the second crosslinked mycelium layer may be enriched for acetamide and/or amide groups.

Any of these mycotextiles may include a support scaffold/layer (generally referred to as a reinforced support scaffold or reinforced support scaffold layer) that may be formed of fibrous or non-fibrous material and may be knitted, woven, etc. The support scaffold layer may form a mesh material having openings there through. The scaffold layer may comprise one or more of: a glass fiber or, a carbon fiber, or carbon nanofibers, or an aramid fiber. The scaffold layer may comprise a vegetable fiber layer, e.g., a cotton layer (that may be formed of cotton fabric).

The first crosslinked mycelium layer may be the same size as the second crosslinked mycelium layer, or it may be thicker than the second crosslinked mycelium layer.

In general, the mycotextiles described herein may include an external humidity barrier on an outer surface of the first crosslinked mycelium layer and/or on an outer surface of the second crosslinked mycelium layer. The external humidity barrier may comprise a soluble biodegradable polymer, a plasticizer, up to 60% wt. of emulsified wax (e.g., between 0.1% and 60%, between about 1% and 60%, between about 5% and 60%, between about 10% and 60%, between about 20% and 60%, etc.), and less than 10% wt. of oil.

Also described herein are mycotextiles comprising: a chemically activated support scaffold layer; a crosslinked mycelium layer comprising a plurality of crosslinked hyphae extending adjacent to at least the first side of the support scaffold layer, wherein the chemically activated support scaffold layer is crosslinked to the mycelium layer, and a plurality of nanoparticles crosslinking chitin within the hyphae of the mycelium layer so that the crosslinked mycelium has a tensile strength that is 5 MPa or greater (e.g., 7.5 MPa or greater, 10 MPa or greater, 12.5 MPa or greater, 15 MPa or greater, etc.).

A mycotextile may include: a chemically activated support scaffold layer; a crosslinked mycelium layer comprising a plurality of crosslinked hyphae extending adjacent to at least the first side of the support scaffold layer, wherein the chemically activated support scaffold layer is crosslinked to the mycelium layer, and a plurality of nanoparticles crosslinking chitin within the hyphae of the mycelium layer so that the crosslinked mycelium has a tensile strength that is at least 10% greater than the tensile strength of the chemically activated support scaffold layer alone.

As mentioned, the chemically activated support scaffold layer may comprise one or more of: a glass fiber or, a carbon fiber or, carbon nanofibers or, an aramid fiber. In some examples, the chemically activated support scaffold layer comprises a carbon fiber reinforcement. The chemically activated support scaffold layer may be chemically activated to covalently bond to chitin within the hyphae of the mycelium layer. The chemically activated support scaffold layer may be between about 0.1 mm to about 0.6 mm.

As mentioned, the plurality of nanoparticles may have a diameter of between 60 and 600 nm. The nanoparticles may comprise ceramic nanoparticles (e.g., $SiO_2$, $TiO_2$, ZnO, $SnO_2$, $Al_2O_3$, $Fe_2O_3$, and $Fe_3O_4$), polymeric nanoparticles (e.g., zein, alginate, chitosan, latex, poly(lactide) (PLA), poly(lactide-co-glycolide) (PLGA) copolymers, and poly (ε-caprolactone) (PCL)), metallic nanoparticles (e.g., Au, Ag, Cu, and Pt), carbon-based nanostructures (nanofibers, single or multi-walled nanotubes, graphene, spheres) and/or composites among them. The plurality of nanoparticles may be functionalized nanoparticles comprising amino-terminal groups bound to a surface of the nanoparticles and/or one or more polyphosphate groups coupled to the surface of the nanoparticles. In some examples functionalized nanoparticles may comprise impregnating nanoparticles having and/or one or more epoxy, acrylic, isocyanate, and/or vinylic groups coupled to the surface of the nanoparticles. In some examples, the plurality of nanoparticles within the crosslinked to hyphae of the crosslinked mycelium layer comprises between 0.1% and 5% by weight of the crosslinked mycelium layer.

The average diameter of the hyphae in the first mycelium layer and the second mycelium layer may be about 1 μm or greater. The chitin fraction of the crosslinked mycelium layer(s) may be 45 to 80%. The crosslinked mycelium layer(s) may be enriched for acetamide and/or amide groups.

Any of these mycotextiles may include an external humidity barrier on an outer surface of the crosslinked mycelium layer, such as (but not limited to) a composition of a soluble biodegradable polymer, a plasticizer, up to 60% wt. of emulsified wax (e.g., between 0.1% and 60%, between about 1% and 60%, between about 5% and 60%, between about 10% and 60%, between about 20% and 60%, etc.), and less than 10% wt. of oil.

Also described herein are methods of forming any mycotextiles described herein. For example, a method of forming a mycotextile may include: selecting a fungal strain, wherein the fungal strain has a hyphal diameter of 1 μm or greater, a chitin fraction of 45 to 80%, and is enriched for acetamide and/or amide groups; generating a pre-inoculum substrate seeded with the selected fungal strain; growing a mycelium mat using the pre-inoculum substrate; processing the mycelium mat to crosslink chitin in the hypha to form the mycotextile.

For example, a method of forming a mycotextile may include: selecting a fungal strain (e.g., in some examples a wild fungal strain), wherein the fungal strain has a hyphal diameter of 1 μm or greater, a chitin fraction of 45 to 80%, and is enriched for acetamide and/or amide groups; generating a pre-inoculum substrate seeded with the selected fungal strain; growing a mycelium mat using the pre-inoculum substrate, wherein a scaffold layer is added while growing the mycelium mat so that the scaffold layer is incorporated into the mycelium mat; processing the mycelium mat to crosslink chitin in the hypha to form the mycotextile.

Selecting the fungal strain may comprise selecting a fungal strain having one or more reactive groups for deacetylation and/or crosslinking apparent between 1500 and 1700 cm$^{-1}$ using attenuated total reflectance (ATR)/Fourier transform infrared (FTIR) spectroscopy. The reactive groups may comprise an additional shoulder around 1700 cm$^{-1}$ visible in ATR/FTIR spectrum, indicating the presence of an additional reactive carbonyl compound as compared to the chitin composition of a control strain of *G. lucidum* SB-0000. In some examples selecting the fungal strain comprises selecting a fungal strain having an additional band in a chitin composition of the strain around 3000 and 3300 cm$^{-1}$ when observed under an attenuated total reflectance (ATR)/Fourier transform infrared (FTIR) spectrum.

In general, any of these methods may include using a custom "foam" method (forming a bio-organic foam). For example, generating the pre-inoculum substrate seeded with the selected fungal strain may include culturing the selected fungal strain in a solid-state bag of substate comprising a sterile grain comprising one or more of: corn, wheat, rice, sorghum, rye, and millet. Growing the mycelium mat using the pre-inoculum substrate may include: preparing a production substrate that is inoculated with the pre-inoculum substrate, preparing a bio-organic foam from the production substrate, and growing the bio-organic foam into the mycelium mat.

Preparing the production substrate inoculated with the pre-inoculum substrate may comprise combining a lignocellulosic material and a nitrogen source having an approximately 40:1 carbon to nitrogen ratio and a moisture content of between 60-75% with the pre-inoculum substrate and incubating the production substrate to grow the selected strain. In some examples, the lignocellulosic material comprises wood chips or sawdust.

Incubating the production substrate may comprise incubating at between 25-30 degrees C. for between 8-14 days.

Preparing the bio-organic foam may include incorporating the production substrate with glycerol (or other polyglycols, e.g., polyethylene glycol and polypropylene glycol, also other compounds, such as polyalkylene oxides, or polyadipates), an activator comprising micronutrients for mycelial development, and water into a homogenized foam.

Incorporating the production substrate may comprise incorporating the production substrate when the selected fungal strain is at a colonization percentage of greater than 90%.

The activator may include a casein solution or a MARILLION activator.

The bio-organic foam may include about 40-50% of colonized production substrate, about 5-10% of 96% w/v of one or more of: a glycerol, a polyglycols, a polyalkylene oxides, or a polyadipates, about 10-15% of activator and water. Growing the bio-organic foam into the mycelium mat may include spreading the bio-organic foam onto a mesh support and incubating for a first time period to form a growing mycelium mat, adding a chemically activated support scaffold layer onto the growing mycelium mat after the first time period, and incubating for a second time period.

Processing the mycelium mat to crosslink reactive moieties in the hypha may comprise impregnating hyphae within the mycelium mat with a plurality of functionalized nanoparticles and covalently or electrostatically crosslinking the functionalized nanoparticles to reactive moieties in the hyphae to form the mycotextile. Growing a mycelium mat may include incorporating a chemically activated reinforced support scaffold within the mycelium mat and covalently crosslinking the chemically activated support scaffold to chitin/chitosan within the mycelium mat.

In some examples, processing the mycelium mat further comprises one or more of: pressing the mycelium mat to a desired thickness, applying a mordant to the mycelium mat, dyeing the mycelium mat, applying an internal wetting composition to the mycelium mat, and/or applying an external wetting barrier composition to the mycelium mat.

In some examples, a method of forming a mycotextile includes: generating a pre-inoculum substrate seeded with a fungal strain; growing a mycelium mat using the pre-inoculum substrate; impregnating hyphae within the mycelium mat with a plurality of functionalized nanoparticles; and covalently crosslinking the functionalized nanoparticles to chitin/chitosan in the hyphae to form the mycotextile.

A method of forming a mycotextile may include: generating a pre-inoculum substrate seeded with a fungal strain; growing a mycelium mat using the pre-inoculum substrate, wherein a scaffold layer is added during while growing so that the scaffold layer is incorporated into the mycelium mat; covalently crosslinking the scaffold layer to chitin within the mycelium mat; impregnating hyphae within the mycelium mat with a plurality of functionalized nanoparticles; and covalently or electrostatically crosslinking the functionalized nanoparticles to chitin in the hyphae to form the mycotextile.

Impregnating the hyphae with the nanoparticles may include soaking or spraying the mycelium mat with a suspension of the functionalized nanoparticles. In some examples impregnating the hyphae comprises applying between about 0.1 g/L and 1 g/L of functionalized nanoparticles acidic aqueous suspension to the mycelium mat. In some examples, impregnating the hyphae comprises impregnating the hyphae with nanoparticles having a diameter of between about 60 and 600 nm. As mentioned above, the nanoparticles impregnated into the hyphae may include ceramic nanoparticles, polymeric nanoparticles, metallic nanoparticles, carbon-based nanoparticles and/or composites among them.

In some examples, impregnating the hyphae with functionalized nanoparticles may comprise impregnating nanoparticles having and/or one or more polyphosphate groups coupled to the surface of the nanoparticles. In some examples functionalized nanoparticles may comprise impregnating nanoparticles having and/or one or more epoxy, acrylic, isocyanate, and vinylic groups coupled to the surface of the nanoparticles. In some examples impregnating the hyphae may comprise impregnating the hyphae with nanoparticles so that the final percentage of nanoparticles is between 0.1% and 5% by weight of the mycotextile.

Covalently or electrostatically crosslinking the functionalized nanoparticles to chitin/chitosan in the hyphae may comprise engaging functional groups with polycarboxylic, polyphosphate, epoxy, acrylic, isocyanate, and/or vinylic groups on a surface of the nanoparticles.

Any of these methods of forming a mycotextile may include: generating a pre-inoculum substrate seeded with a fungal strain; growing a mycelium mat using the pre-inoculum substrate comprising: preparing a production substrate that is inoculated with the pre-inoculum substrate, preparing a bio-organic foam from the production substrate, and growing the bio-organic foam into the mycelium mat; and processing the mycelium mat to crosslink chitin in the hypha to form the mycotextile.

Preparing the production substrate inoculated with the pre-inoculum substrate may include combining a lignocellulosic material and a nitrogen source having an approximately 40:1 carbon to nitrogen ratio and a moisture content of between 60-75% with the pre-inoculum substrate and incubating the production substrate to grow the selected strain. As mentioned, the lignocellulosic material comprises wood chips or sawdust. Incubating the production substrate may comprise incubating at between 25-30 degrees C. for between 8-14 days. Preparing the bio-organic foam may incorporate the production substrate mixed with glycerol (or other polyglycols, e.g., polyethylene glycol and polypropylene glycol, also other compounds, such as polyalkylene oxides, or polyadipates), an activator comprising micronutrients for mycelial development, and water into a homogenized foam.

Incorporating the production substrate may comprise incorporating the production substrate when the selected fungal strain is at a colonization percentage of greater than 90%.

The activator may comprise a casein solution or a MARILLION activator.

The bio-organic foam may comprise about 40-50% of colonized production substrate, about 5-10% of 96% w/v glycerol (or other polyglycols, e.g., polyethylene glycol and polypropylene glycol, also other compounds, such as polyalkylene oxides, or polyadipates), and about 10-15% of activator and water. Growing the bio-organic foam into the mycelium mat may comprise spreading the bio-organic foam onto a mesh support and incubating for a first time period to form a growing mycelium mat, adding a chemically activated support scaffold layer onto the growing mycelium mat after the first time period, and incubating for a second time period.

Processing the mycelium mat to crosslink chitin/chitosan in the hypha may comprise impregnating hyphae within the mycelium mat with a plurality of functionalized nanoparticles and covalently or electrostatically crosslinking the functionalized nanoparticles to chitin/chitosan in the hyphae to form the mycotextile. In some examples growing a mycelium mat comprises incorporating a chemically activated support scaffold within the mycelium mat and covalently crosslinking the chemically activated support scaffold to chitin within the mycelium mat.

As mentioned, processing the mycelium mat may further comprise one or more of: pressing the mycelium mat to a desired thickness, dyeing the mycelium mat, applying a mordant to the mycelium mat, applying an internal wetting composition to the mycelium mat, and applying an external wetting composition to the mycelium mat.

All of the fungal strains, methods, and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments and the accompanying drawings of which:

FIGS. 2A-2K shows tables illustrating examples of fungal strains isolated from the wild that may be tested or screened as described herein as part of a method for generating and/or processing a fungal-deriver textile.

FIGS. 4A and 4B show tables of examples of taxa using the Universal Barcode ITS region for the putative wild strains compared in different public domain Gene Databases. The Accession number of all ITS region sequences deposited in the GenBank DataBase are indicated.

FIG. 4C shows an example of a morphological characterization of collected basidiomes of 0002, 0006, 0014, and 0028 and their comparison with basidiomes from *Trametes cubensis* and *Leiotrametes menziessi* reported in scientific literature, which evidence that taxonomic characteristics of our wild fungal strains do not correspond to those reported for *L. menziesii* and *T. cubensis*.

FIGS. 5A-5B are tables showing examples of which culture media provided the best growth for each tested putative fungal strain.

FIG. 6A is a table showing concentrations of pooled antibiotics (Amoxicillin and Ampicillin) tolerated by promising strains.

FIG. 6B is a table showing the concentrations of pooled antibiotics (Amoxicillin, Ampicillin, and Ciprofloxacin) tolerated by sample fungal strains tested as described herein.

FIG. 7 is a table showing a growth percentage of example fungal strains in culture media supplemented with inducers of enzymatic machinery associated with the lignocellulosic matter degradation.

FIG. 13 is a table summarizing examples of phenotypic features for potential fungal strains that may be used herein.

FIG. 14 is a table summarizing various types of grains used in the pre-inoculum substrate for different potential fungal strains.

FIG. 15 is a table illustrating growth kinetics and colonization homogeneity of example strains inoculated in PDB+antibiotic from fresh mass plates.

FIG. 18 illustrates one example of attenuated total reflectance (ATR)/Fourier transform infrared (FTIR) spectrum of a support structure comprising, in this example, a vegetable support fabric that was chemically activated with 2% w/v citric acid (e.g., activated cotton) as compared with the non-activated textile (e.g., cotton).

FIGS. 19A-19B shows scanning electron micrograph images of one example of a fungal-derived textile formed from a strain of fungus, G. lucidum SB-0000, that has been crosslinked using a conventional scheme of tannic acid. FIG. 19A shows a top view, and FIG. 19B shows a side view through the material.

FIG. 22A is a scanning electron micrograph of $SiO_2$ nanoparticles synthesized as described herein using 3-Aminoproyltriethoxysilane (APTES) and phosphoric acid as functionalizing agents.

FIG. 22B is a graph illustrating the size distribution of the $SiO_2$ nanoparticles shown in FIG. 22A.

FIG. 23 schematically illustrates the functionalization of nanoparticles used as an example the (3-aminopropyl) triethoxysilane (APTES).

FIG. 24A is a graph showing an example of an ATR/FTIR spectra of unmodified $SiO_2$ nanoparticles and APTES-modified nanoparticles.

FIG. 24B is a graph showing a Raman scattering spectrum for nanoparticles (spheres) modified with phosphate groups.

FIG. 30A shows a scanning electron microscopy image of a prototype material prepared as described herein, using the 0006 fungal strain, and applying all the post-treatment strategies described herein, including internal wetting, crosslinking, pressing, activation with mordant, dyeing, and external wetting.

FIG. 30B is an enlarged view of the outer surface (highlighting the thickness of the external humidity barrier).

FIG. 31A shows a scanning electron microscopy image of a prototype material prepared as described herein, using the 0006 fungal strain and, applying all the post-treatment strategies described herein, including internal wetting, crosslinking, pressing, activation with mordant, dyeing, and external wetting based on zein.

FIG. 31B shows a scanning electron microscopy image of the top view of a prototype material prepared as described herein, applying all the post-treatment strategies described herein, including internal wetting, crosslinking, pressing, activation with mordant, dyeing, and external wetting based on zein.

DETAILED DESCRIPTION

Figure 1:
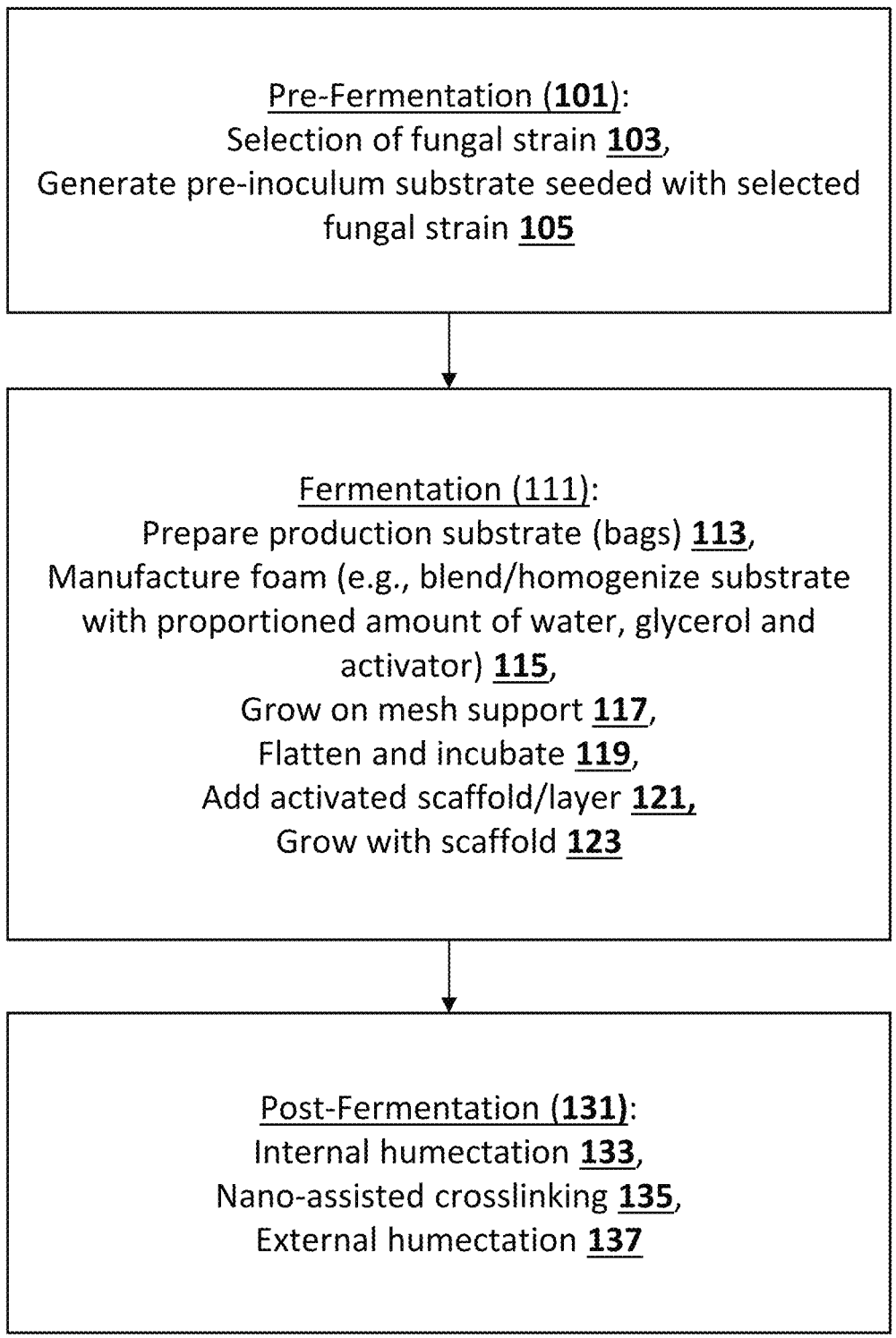
FIG. 1 schematically illustrates one example of a system as described herein.

Described herein are mycotextiles and methods for making them. These mycotextiles provide numerous advantages over previously described materials, including fungal material. Specifically, the material itself may have superior properties and characteristic features (which may be apparent at the ultrastructural level) and the many advantages of the distinct methods of making these mycotextiles compared to the prior art.

In particular, described herein are mycotextiles that may generally include a support scaffold layer crosslinked to one or more crosslinked mycelium layer(s). The mycelium layer(s) may extend adjacent to the first side of the support scaffold layer. In any of these textiles, the mycelium layer(s) may also include functionalized nanoparticles within the crosslinked mycelium layers. Specifically, the nanoparticles may be functionalized to crosslink chitin/chitosan within the hyphae of the first crosslinked mycelium layer and the second crosslinked mycelium layer.

As used herein, the term "hyphae" may refer to a morphological structure of a fungus that is characterized by a branching filamentous shape. The term "hyphal" may refer to an object having a component thereof comprised of hyphae. The term "mycelium" may refer to a structure formed by one or more masses of branching hyphae. A "mass" refers to a quantity of matter.

The methods, compositions, and apparatuses for mycotextiles described herein may us previously unknown strains of white-rot belonging to the Polyporaceae family that have been identified to have characteristics that provide superior features for the development of mycotextiles than those provided by other species of the Ganodermataceae family, such as *Ganoderma lucidum, Ganoderma tsugae, Ganoderma oregonense, Ganoderma tsugae, Ganoderma applanatum, Ganoderma resinaceum*. In some examples, the preferred candidates may include *Trametes versicolor* and *Trametes pubescens*, belonging to the Polyporaceae family. As described in greater detail below, currently used strains, such as the *G. lucidum* SB-0000 strain, are used herein as a control species.

The order Polyporales, which represents 1.5% of all described fungal species worldwide, belongs to the class Agaricomycetes, a large and highly diverse group of fungi within the Phylum Basidiomycota. Polyporales are widely distributed in boreal, temperate, tropical, and subtropical areas. Their high diversification rates are most likely because they could be around 183 million years old, according to molecular clock analysis of an Agaricomycetes phylogenomic dataset. This suggests genomic and enzymatic mechanism adaptations occurred in Polyporales fungi to various ecological niches and substrates, including wood decay. The vast majority of Polyporales are efficient saprotrophs in wood decomposition with a significant contribution to the carbon cycle in forest soils. Depending on the symptoms of degradation, the attack caused by decomposing fungi on wood has traditionally been classified into two types of decomposition: i) white-rot fungi, which degrade all the polymers of the plant cell wall, including the lignin, often leaving behind lighter colored cellulose and, ii) brown rots (brown-rot fungi), which degrade cellulosic and hemicellulosic compounds of the plant cell wall with partial modification of lignin. Each type of rot fungi decomposition type involves a characteristic panel of enzymatic and chemical mechanisms for the degradation of plant cell wall polymers generally reflected in a different repository of genes encoding oxidative degrading enzymes in the genome.

The diverse enzymatic system in Polyporales may be used as described herein to provide biobased chemicals and biomaterials for fungal textiles derived from a renewable carbon source, such as plant biomass, without competing with food or animal feed production, without prejudice to the preservation of natural ecosystems. In this context, the enzymatic machinery of Polyporales white-rot fungi may allow for the transformation of plant tissues and the possibility of using waste or co-products from agriculture and forestry, highly recalcitrant to microbial degradation for the development of multiple industrial bioprocesses, such as the manufacture of mycotextiles.

Described herein are new strains of white-rot fungi belonging to the family Polyporaceae that have been further identified to provide the characteristics that may be particularly beneficial for generating mycotextiles. Appropriate strains (e.g., strains of Polyporaceae) may possess highly active enzymatic mechanisms for the oxidative degradation of non-starch polymers capable of utilizing crude biomasses as a source of carbon and energy in pristine regions of high biological diversity.

In general, strains with the appropriate characteristics may be fermented (as part of a fermentation stage), which gives rise to the formation of a "mycelium mat" that may be treated by the specific physicochemical treatments described herein to improve quality and durability to the biomaterial obtained. The processes of growing and forming the mycelium mat may be carried out as described herein. Whereas previous work has described the use of fungal pulp in the production of textiles, including the specific use of fungal cell wall components, such techniques may be inappropriate for the formation of the mycotextiles described herein. For example, prior formulation methods require surface conditioning, cross-linking, finishing, pressing, and drying. The process, in general, is outlined in the following steps: (i) initially, the precursor tissue can be treated to increase its water content, (ii) the tissue is treated with sodium hydroxide, acetic acid, or alcohol to remove soluble components of the extracellular matrix, (iii) the crosslinking agents react with chitin fibrils, (iv) fungal biomass is hot or cold-pressed, (v) moisture is then returned to the material, (vi) material can be dyed and printed in a specific pattern before for a final drying step to be completed. This process requires a durable internal humectant to be incorporated to avoid losing the moisture content too quickly. Further, the crosslinking step is typically based on traditional vegetable tanning strategies. As mentioned above, these techniques may result in delamination of the material and a woody appearance and may be difficult to control. Finally, an external moisture barrier (or plasticizing stage) has traditionally been required to ensure the durability of the mycotextiles.

Although crosslinking strategies may improve mycelium's mechanical characteristics, they are not sufficient to provide the high resistance that cowhide or synthetic leather presents and, therefore, biotextiles may be used as support. In some examples, vegetable fibers such as cotton, hemp, and jute may be used due to their low environmental risk and excellent mechanical properties. The tensile strength and Young's modulus of such materials may increase with the cellulose content (with the degree of polymerization). Fibers such as cotton, jute, and hemp report tensile strengths in a range of 300 to 800 $N/mm^2$. During the growth process of the layer of aerial mycelium, the structural and mechanical characteristics of the supporting tissue may decrease because they also represent a lignocellulosic substrate. Described herein are methods and compositions that may use scaffolds capable of allowing the growth of the mycelium without negatively affecting its characteristics.

As described above, leather substitutes potentially derived from mycelium of fungi (e.g., one example of a fungal-derived textile), as described herein, may have a low environmental impact. These leather substitutes may be obtained by recycling low-cost agricultural by-products transformed into chitinous polymers and other polysaccharides through a natural biological process during fungal growth. Filamentous fungi display an intrinsic growth pattern that generates a potentially infinite number of microscopically interconnected tubular cells producing a vast macroscopic biomass network known as mycelium. Pure mycelial biomass can be separated from its substrate to produce sustainable materials with adjustable properties ranging from foam, paper, leather, and polymers. After various physicochemical treatments, these layers of fungal biomass may visually resemble leather, as will be described herein.

Thus, described herein are self-generated functional textiles using fungal mycelium. The mycotextiles developed herein may also include methods and compositions using one or more biotechnology approaches using selected native fungal strains, e.g., of the Polyporaceae family, which may have physiological, biochemical, metabolic, enzymatic, and phenotypic characteristics that distinguish them from those species suggested for use with fungal-based materials, including textiles. In some examples, the methods and apparatuses described herein may refer to fungi of the Ganodermataceae family or *Trametes* genera belonging to the Polyporaceae family having specified characteristics.

The use of specified fungal strains in combination with the specified nanotechnological tools, materials engineering, and green chemistry described herein may allow new physicochemical and mechanical properties and functionalities of the mycelium (e.g., for mycotextiles) that are particularly beneficial. Also described herein are mycotextiles that may be configured as so-called "smart" or "intelligent" materials that may have engineered properties.

Described herein are methods, compositions (including mycotextiles, substrate, and components), and apparatuses (e.g., devices, systems, etc.) that may be used to make and/or process (e.g., as part of the manufacturing process) to generate aesthetically pleasing and functional mycotextiles having desired properties that may be manufactured in a manner that can be readily scaled. Thus, described herein are biotechnological and nanotechnological strategies that may cover the entire production process. For example, FIG. 1 illustrates one example of a complete processing flow diagram to manufacture a mycotextile (e.g., mycotextile) having the superior properties as described herein. Each of these stages and steps is described in greater detail herein and may include some or all of those illustrated in FIG. 1, including but not limited to: a pre-fermentation stage 101, a fermentation stage 111, and a post-fermentation stage 131. The pre-fermentation stage 101 may include isolation, identification, and characterization of the substrate fungal strain(s) 103, such as non-Ganodermataceae fungal strains belonging to the Polyporaceae family having one or more characteristics described herein, and generation of the pre-inoculum substrate using this fungal strain 105. The fermentation stage 111 may include including culturing in one or more specifically engineered culture medium, in some cases using one or more solid-state and hybrid fermentation substrates (e.g., substrate "bags" 113) that may be scaled for the fungal strain(s) used, as well as the formation of a foam substrate (homogenizing the inoculated substrate with other components configured to allow rapid growth 115), as well as the addition of an activated scaffold/layer 121. Mid-fermentation steps may include the addition of functionalized nanoparticles and/or the addition of the scaffold/layer, flattening, etc., followed by additional growth and expansion of the material 123. The post-fermentation stage 131 may include treating the material (e.g., adding functionalized nanoparticles and/or nano-assisted crosslinking 135, internal humectation 133, and/or external humectation 137). These steps may include or may be separate from additional dyeing and/or tanning steps.

These methods may result in fungal-derived textiles having superior mechanical and aesthetic characteristics. For example, these methods may result in compositions of fungal derived textiles including mechanical properties such as materials having a tensile strength that is 16 MPa or greater (e.g., 17 MPa or greater, 18 MPa or greater, 19 MPa, 20 MPa or greater, 21 MPa or greater, 22 MPa or greater, 23 MPa or greater, 24 MPa or greater, between about 16-40 MPa, between about 16-35 MPa, between about 16-30 MPa, between about 18-40 MPa, between about 20-40 MPa, etc.), an elongate before breaking of 20% or more (e.g., 25% or more, 30% or more, 35% or more, 40% or more, etc.), a tear strength of 16 KN/m or more (e.g., 18 KN/m or more, 20 KN/m or more, 22 KN/m or more, 24 KN/m or more, 30 KN/m or more, 35 KN/m or more, etc.), able to withstand greater than 1000 abrasion cycles (e.g., greater than 1000 (1 lb) still abrasion cycles). These characteristics are equivalent or better than textiles such as animal leather and are better than those previously described.

The methods described may be performed much faster than previously described techniques, which provide numerous advantages as compared to these techniques, requiring less time and resources to produce large quantities. For example, the methods described herein describe a complete (e.g., "all-in-one") manufacturing method that improves each stage of the bioprocess and allows for the adjustment and improvement of the characteristics of the resulting mycotextile (e.g., mycotextile). Importantly, these methods are also configured to be scalable.

Pre-Fermentation

In general, the methods and compositions (e.g., textiles) described herein may generally be performed with any appropriate fungal strain. However, many of these methods may be performed with a fungal strain having characteristics that may be particularly beneficial. For example, any of the methods and compositions described herein may be used with and/or may include a fungal strain having specific combinations of characteristics that have been identified for the first time herein.

Any of the methods described herein may include selecting a strain of fungus having a chitin fraction of 45 to 80%. For example, the chitin fraction of the cell wall may be between about 45% and about 80%. In particular, the fungal strain used may be enriched for acetamide and/or amide groups, which may be particularly beneficial to the methods described herein in which an activated scaffold (e.g., activated layer) and/or functionalized nanoparticles are used, as described in greater detail below.

In some examples, the selected strain may also have a highly fibrillar morphology and hyphae diameter. For example, the fibrillar morphology of their mycelium may have a hyphae diameter of greater than about 1 µm (e.g., between about 1.0±0.3 to 1.6±0.5). A higher hypha diameter may also further enhance the chitin content and assist with the final product's enhanced mechanical properties.

In any of the methods described herein, the fungal strain may rapidly grow when induced by one or more organic inducers. For example, the strain(s) may be selected for higher growth kinetics in a solid culture media supplemented by organic inducers (1% w/v) on the 3rd day of incubation. Higher growth kinetics in the culture medium may result in a higher growth rate in the pre-fermentation stage, reduced operation times, and reduced contamination probabilities. Alternatively, or additionally, the fungal strains may be selected for a higher growth kinetic and homogeneity growing in PDB liquid medium. Higher growth kinetics and homogeneity in the liquid culture may mean a high reproducibility in the scaling-up bioprocess and/or a higher growth velocity, reduced operation times, and contamination probabilities.

In addition, in some examples, the fungal strains used herein may also be characterized as having a tolerance for citric and phosphate ions. In any of these examples, the fungal strain(s) may include reactive chemical groups for deacetylation. For example, as compared to a fungal control strain G. lucidum SB-0000, the strain used may include (e.g., between 3000 and 3300 $cm^{-1}$ when observed under an attenuated total reflectance (ATR)/Fourier transform infrared (FTIR) spectra (ATR/FTIR spectra) a more hydrophilic surface, observed as a broader band related to the contribution of O—H and N—H groups. The fungal strain(s) may also be selected to include an additional amide moiety in the chitin composition of the strain, e.g., between 1500 and 1700 $cm^{-1}$ (using ATR/FTIR spectra), showed a characteristic C=O and N—H vibrations for amide moiety in chitin, such as an additional shoulder at 1734 $cm^{-1}$ (which becomes more intense after polysaccharides extraction), indicating the presence of another type of carbonyl compound, e.g., an anhydride or an ester which is not observed in the control strain. Thus, the fungal strains used herein may include a carboxylic group on the chitin, e.g., an additional carbonyl moiety that is particularly useful in the crosslinking strategies described herein, which may provide acidic sites able to protonate and provide novel anchoring sites for anions such as phosphate and citrate or for electrostatic interaction with cations or molecules with a positive charge density.

As will be described in greater detail here, the methods and compositions described may use fungal strains that are distinct from those previously used, which are typically within the Ganodermataceae family or Trametes genera. In particular, the fungal strains used may be selected from a genus of the Polyporaceae, Xylariaceae, Auriculariaceae, Panaceae, Hypoxylonaceae, and/or Hymenogastraceae families. For example, these fungal strains may be selected from one or more species of the Lentinus, Polyporus, Xylaria, Earliella, Panus, Auricularia, Hypoxylon, and/or Psilocybe genera. Also, it may be selected from one or more species of the Leiotrametes genus, such as Leiotrametes menziesii, Leiotrametes lactinea, and/or Leiotrametes sp., and/or it may use a distinct species of Trametes genus never used previously, such as Trametes cubensis. Leiotrametes menziesii has been recently classified as Cubamyces menziesii (Berk.). For the purposes of the present document Leiotrametes menziesii name will be used.

A variety of different white-rot fungi of the family Polyporaceae were isolated, identified, and examined to be used as a starter culture (e.g., wild fungal strain) in the methods described herein. Strains of the order Polyporales may be identified by morphological characteristics of their fruiting bodies growing on decomposing lignocellulosic substrates. However, fungal species of the Xylariaceae, Auriculariaceae, Panaceae, Hypoxylonaceae, and/or Hymenogastraceae families may also be used. The methods described herein may be applied to known or novel fungal strains, including newly identified strains or unclassified strains.

Table 1 (FIGS. 2A-2K) illustrates examples of fungal species that may be used as described herein. In some cases, these fungi were identified from native fungi (e.g., hotspots of high biological diversity worldwide), recorded photographically, measured, and georeferenced. In the case of fruiting bodies, at least one for each phenotype observed in the field was collected as completely as possible and stored in autoclaved jars with lids. Each collected sample was labeled, transported in a cooler, and stored at 4° C. Fresh fruiting bodies were washed with sterile distilled water to remove impurities and particles of soil. In a vertical laminar flow chamber, the samples were introduced into vials with 5% v/v chlorine for 5 minutes and manual agitation. After the time, they were washed with abundant autoclaved distilled water, and, subsequently, the samples were treated with 70% v/v ethanol with the help of an atomizer. Using dissection forceps and a scalpel, three segments of the internal tissue between 0.1-1 mm were removed and seeded in duplicate in Petri dishes with PDA culture medium supplemented with a broad-spectrum antibiotic (e.g., ampicillin-amoxicillin) and incubated at 28° C. for 7 days.

Fungal strains were isolated in axenic culture, and each strain was conserved at +4° C. to create a germplasm bank and backup for subsequent research activities. Table 1 shows information regarding the 26 wild fungal strains isolated as described above. The strains were phenotypically characterized according to their ability to grow on various lignocellulosic substrates, and their growth kinetics and potential for developing mycotextiles were evaluated as described herein. 16 isolates were molecularly identified based on PCR amplification and DNA sequencing of diverse DNA barcodes. In addition, a commercial strain Ganoderma lucidum SB-0000 (GL), was included in the molecular identification.

E.Z.N.A. Fungal DNA Mini kit de OMEGA BIO-TEK was used for DNA extraction and purification. Specific for the rapid and reliable isolation of high-quality DNA from a wide variety of fungal species and tissue. From vegetative mycelium, approximately 300 mg of lyophiles were taken in a 1.5 mL Eppendorf tube for each strain. Subsequently, the mycelia were crushed with a plastic pestle, and 800 µl of FG1 buffer was added to the tube; these were mixed vigorously with a vortex. Once the pellet separated from the walls of the tube, it was incubated at 65° C. for 30 minutes, gently mixing the tube every 5 minutes. Subsequently, 180 µl of FG2 buffer was added, vigorously vortexed, and incubated on crushed ice for 10 minutes. The tube was centrifuged at 10,000×g for 10 minutes.

Next, the supernatant was transferred to a new tube avoiding touching the pellet (approx. 750 µl). 750 µl of isopropanol was added (1:1 ratio) and centrifuged for 5 minutes at RT to precipitate the DNA. In the next step, all the supernatant was discarded, resuspended in deionized water heated to 65° C., and carefully resuspended with a vortex. Once the pellet was resuspended, 4 µl of RNase A was placed and incubated at 37° C. for 30 min. Next, in the same tube, 150 µl of FG3 buffer and 150 µl of absolute molecular grade ethanol were placed and mixed gently with a vortex. The entire sample was transferred to a HiBind DNA mini-column inserted in a 2 ml collection tube, and centrifuged at 10,000×g for 1 minute. Consecutively, the filtrate from the collection tube was discarded for the addition of 750 µl DNA wash buffer, and it was centrifuged at 10,000×g for 1 minute. The column membrane was dried by centrifugation at 12,000×g for 1 minute. The content was transferred to a new Eppendorf tube, 75 µl of elution buffer was added, incubated at 65° C. for 5 minutes, and then centrifuged at 10,000×g for 1 minute. The same procedure was repeated but using 50 µl of elution buffer. Finally, the DNA was stored at −20° C. until its quantity and quality were determined using a Thermo Fisher Scientific Nano-Drop One UV-Vis spectrophotometer. The concentration of nucleic acids and DNA purity was calculated from the ratios of two absorbance purity indices $A_{260}/A_{280}$ and $A_{260}/A_{230}$.

Molecular identification was performed by PCR amplification and SANGER sequencing of two DNA barcodes: i) the nuclear ribosomal internal transcribed spacer (ITS) region, as a universal DNA barcode marker for Fungi, and ii) the RPB2 nucleotide sequences (RNA polymerase II second largest subunit) as a second molecular marker, widely used for Basidiomycota Phylum. The sequences were edited and assembled with SnapGene Software (https://www.snapgene.com) and compared with various databases to confirm the results obtained: i) GenBank (http://www.ncbi.nlm.nih.gov/Genbank/) using BLASTN (https://blast.ncbi.nlm.nih.gov/Blast.cgi); ii) Fungene-db (http://www.fungene-db.org), a taxonomic classification platform for the authentication of Polyporales strains that resides in the Mycobank Database (https://www.mycobank.org/), property of the International Mycological Association (IMA, http://www.ima-mycology.org); and iii) UNITE Community Reference Sequence (https://unite.ut.ee), a database and sequence management environment focused on the eukaryotic ITS nuclear ribosomal region and its communication via DOIs. The multiple alignments of the sequences were performed with the MUSCLE algorithm integrated into the MEGA X software version 10.1.8. Phylogenetic trees were inferred by using the Maximum Likelihood method and Tamura-Nei model. The bootstrap consensus tree inferred from 2000 replicates represents the evolutionary history of the taxa analyzed.

Figure 3A:
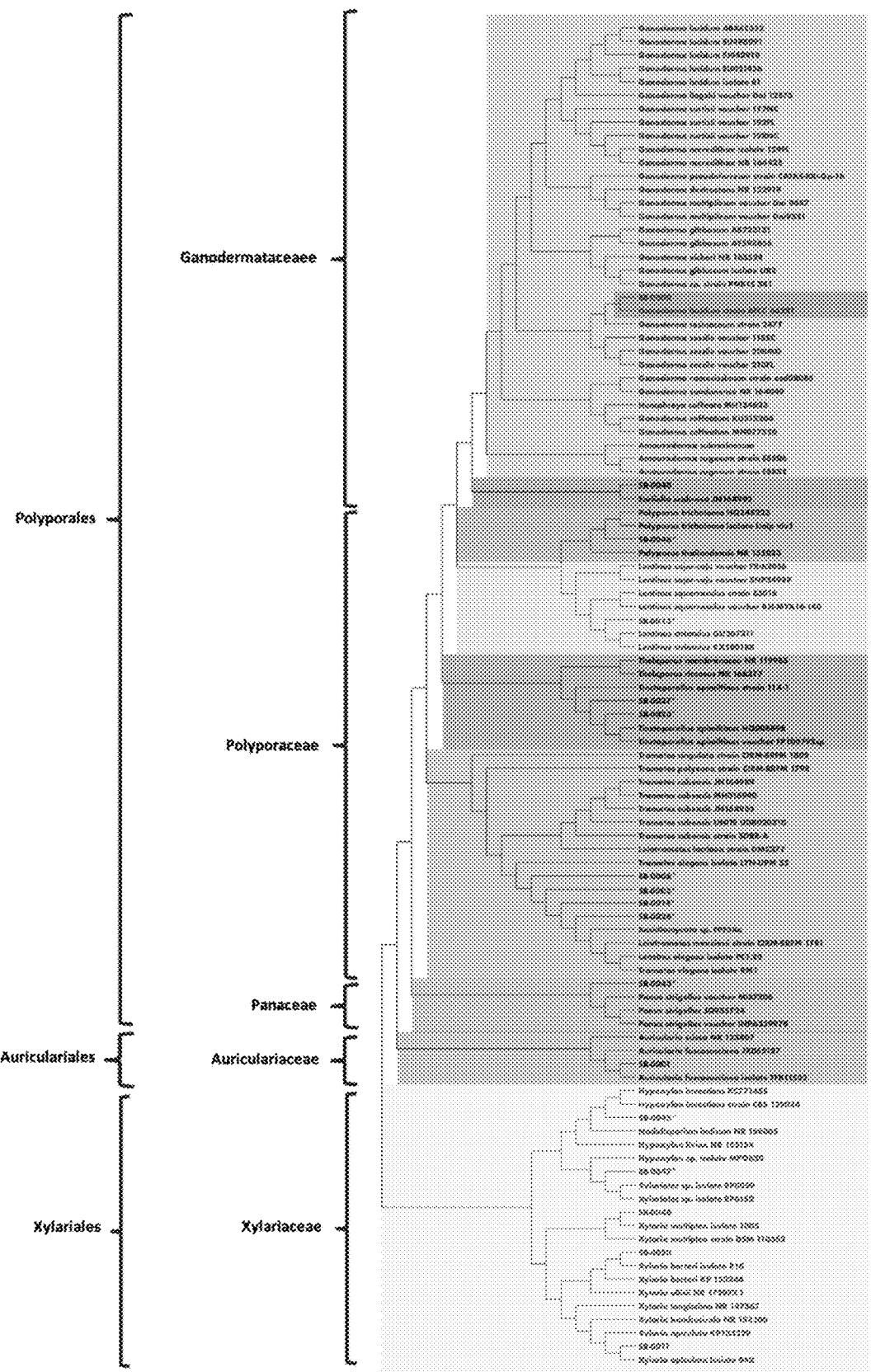
FIG. 3A shows an example of a phylogenetic tree using the ITS region sequences of the 16 sampled collections with 100 homologous DNA sequences downloaded from the GenBank Database.
Figure 3B:
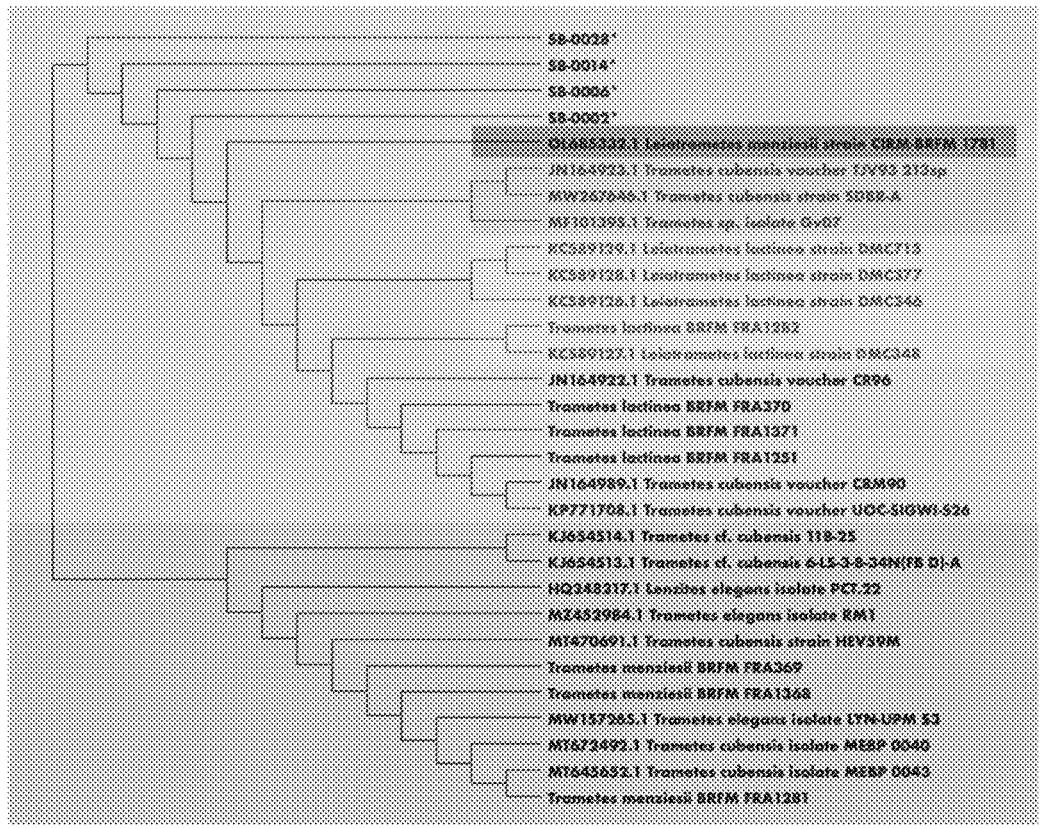
FIG. 3B shows an example of a phylogenetic tree using 30 ITS region sequences downloaded from the GenBank Database, highlighting the clade grouping the 0002, 0006, 0014, and 0028 fungal strains with species of the genera *Trametes* and *Leiotrametes*.
Figure 3C:
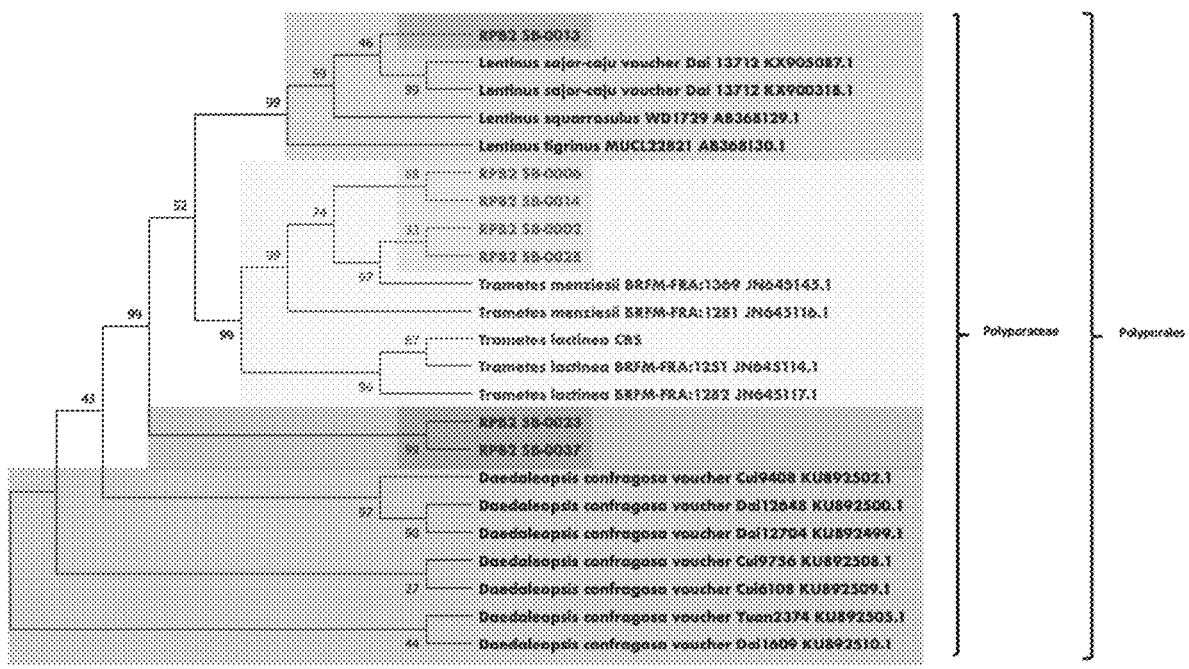
FIG. 3C shows an example of a phylogenetic tree using 23 sequences downloaded from the GenBank Database of the partial RNA polymerase II core subunit RPB2, used as a second molecular marker (DNA barcode), also highlighting the clade grouping the 0002, 0006, 0014, and 0028 fungal strains with species of the new genera *Leiotrametes*.
Figure 3D:
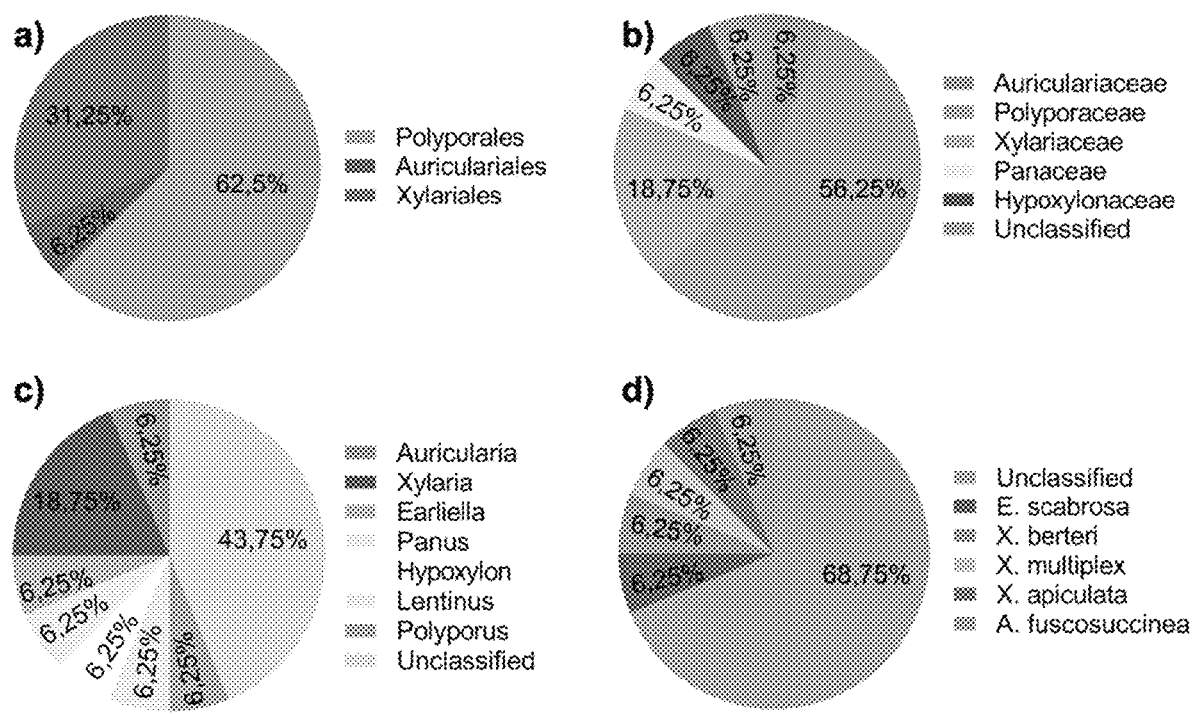
FIG. 3D shows the distribution of isolated wild fungal strains according to taxon: a) Order, b) Family, c) Genus, and d) Species.

From the results obtained through molecular identification, the constructed phylogenetic trees (see, e.g., FIG. 3A-3C) and the morphological descriptions (FIG. 4C) show that, of the total number of specimens collected and molecularly identified (e.g., 16 strains), 68.75% correspond to new species, 43.75% could correspond to new genera, and 56.25% of the isolates belong to the Polyporaceae family. Only one specimen, identified as *Earliella scabrosa* (SB-0040), belongs to the Ganodermataceae family. In total, 62.5% of the collections belong to the Polyporales order, 31.25% to the Xylariales order, and 6.25% to the Auriculariales order. FIG. 3D shows the distribution of isolated wild fungal strains according to the taxon, and Table 2 (FIGS. 4A-4B), indicates the list of taxa using the universal DNA Barcode ITS region of the wild fungal strains based on the results obtained in the different Gene Databases, including the commercial strain *G. lucidum* SB-0000 (GL), used as a control in all the experimental tests.

Two strains were identified at the genus level within the Polyporaceae family, such as *Polyporus* sp. SB-0046 and *Lentinus* sp. SB-0013, while six strains 0002, 0006, 0014, 0028, 0023 and 0037 remain unclassified (named Polyporaceae Unclassified). Despite that, the sequences of the strains 0002, 0006, 0014, and 0028 obtained 99-100% identity (Table 2) with the sequences of *Leiotrametes menziesii* strain CIRM-BRFM 1781 (Accession number GenBank OL685332.1), reported by Hage et al., (2021), and the sequence of Basidiomycota sp. FPF38a (Accession number GenBank JX416577.1), reported by López-Quintero et al., (2013) in the GenBank Database, also showed homologies to the sequences of *Trametes cubensis* voucher CRM90 (Accession number GenBank JN164989.1) and *Trametes cubensis* (Accession number GenBank SH1186469.08FU) in the databases Fungene and UNITE Community, respectively. These results reveal divergences in the repositories to molecularly identify these new collections at the genus and species levels. For this reason, we decided to build a phylogenetic tree using a total of 100 sequences from the ITS region downloaded from the GenBank Database homologous for each of the studied strains.

The phylogenetic tree obtained (FIG. 3A) reveals a group of strains 0002, 0006, 0014, and 0028 within a shared clade with species of the Polyporaceae family belonging to the *Trametes* and *Leiotrametes* genera, which is clearly separated from the clade formed by species of the Ganodermataceae family. However, despite the phylogenetic closeness with species of the *Trametes* and *Leiotrametes* genera, it is impossible to obtain a clear and conclusive classification. A second phylogenetic tree was carried out to elucidate these results (FIG. 3B) using a total of 30 DNA sequences from the ITS region, including species of the genus *Trametes*, such as; *T. cubensis*, *T. lactinea*, *T. elegans*, *T. menziesii*, and the *L. menziesii* and *L. lactinea* species belonging to the *Leiotrametes* genus. These species are the same previously used in phylogenetic analyses supporting the *Leiotrametes* genus description. Notably, *L. Lactinea* was documented in South America and the south of the USA, while *L. menziesii* was reported in the Neotropics.

The obtained phylogenetic tree (FIG. 3B) shows a clade that again groups strains 0002, 0006, 0014, and 0028 with species of the genera *Trametes* and *Leiotrametes*. However, in addition to not forming sub-clades with them, they are separated from the rest of the studied sequences. Inconclusive results are obtained again, suggesting that isolates 0002, 0006, 0014, and 0028 could be considered a new species or genus within the Polyporaceae family. For this reason, a phylogenetic tree was constructed using the partial RNA polymerase II core subunit RPB2 as a second molecular marker (DNA barcode) with a total of 23 DNA sequences downloaded from the GenBank Database homologous for each of the studied strains.

The obtained phylogenetic tree (FIG. 3C) using the partial RNA polymerase II core subunit RPB2 as a second molecular marker shows a clade that again groups strains 0002, 0006, 0014, and 0028 with species of the new genera *Leiotrametes*, such as *L. menziesii* and *L. lactinea*; however, these strains do not form sub-clades with any of them. The results suggest that isolates 0002, 0006, 0014, and 0028 could be considered a new species within the *Trametes* or *Leiotrametes* genera or a new genus within the Polyporaceae family.

The morphological characterizations of the basidiomas collected strains 0002, 0006, 0014, and 0028 did not correspond to the taxonomic characteristics reported for *L. menziesii* (FIG. 4C). The genera Artolenzites, *Trametes*, and *Leiotrametes* contain some species with a laminated hymenophore. Although the type of hymenophore is usually stable at the species level, its structure is variable within the *Trametes* and even more so in *Leiotrametes* sp., depending on the specimen (mainly daedalian, mainly lamellated, or mixed pattern). In *L. menziesii*, young specimens show regular pores, of which only radial spreads develop with age to give a secondarily false daedalian or somewhat lenzitoid structure, with the primary septa still visible at the bottom of the alveoli. However, the types of hymenophores of the collections 0002, 0006, 0014, and 0028 are not similar to those reported for *L. menziesii*. In fact, are more similar to those described for *L. lactinea*, which are characterized by being poroid with round pores.

Likewise, *L. menziesii* is characterized by having a thin to a slightly fleshy cap, sessile to slightly stipitate, mostly gregarious. The hairy surfaces are glabrous, concentrically zoned by various shades of gray, white, and brown. As shown in FIG. 4C, collection 0002 has a thick foot or stem and a very fleshy cap. Collection 0014 and 0028 have a fleshy cap with red and dark brown colors, respectively, despite not having a foot. The crown of collection 0006 is the one that could be closest to the morphological characteristics of *L. menziesii*; however, the divergences observed in the molecular identification, the evidence obtained in the phylogenetic trees (FIG. 3A-3C), and the type of hymenophore observed (FIG. 4C) do not allow to achieve a complete classification at genus and/or species levels (named Polyporaceae Unclassified).

Species collections 0023 and 0037 within the species of the Polyporaceae family belong to the species *Tinctoporellus epimiltinus* and two species of the *Theleporus* genus. However, these last two sequences form a separate sub-clade. The sequences of the strains 0023 and 0037 do not present any homology with any sequence of the ITS region deposited in the GenBank Database (Uncultured fungus clone ZMTDH201308-27 and Uncultured fungus clone ZMTDH201308-13, respectively), while with the UNITE Community Database match was only obtained at the Class Agaricomycetes level (SH1179607.08FU). Likewise, the construction of a third phylogenetic tree with 10 sequences from *Tinctoporellus epimiltinus* and *Tinctoporellus* sp. showed that strains 0023 and 0037 formed a separate sub-clade of the sequences, so they could not be classified at the genus and species level (named Polyporaceae Unclassified).

From the 26 collections, 9 fungal strains were characterized for suitability with the methods, compositions, and apparatuses described herein. These 9 fungal strains were: SB-0002, SB-0006, SB-0013, SB-0014, SB-0023, SB-0028, SB-0037, SB-0046, and SB-0047. The rest of the fungal strains, or a combination of them, may also be characterized and used as described herein.

Growth and Maintenance of Fungal Species

Once the aseptically isolated mycelium was obtained in Petri dishes, mass plates of all promising strains were reseeded. 20 mL of culture medium previously sterilized for 35 min at 121° C. and 15 psi supplemented with a pool of antibiotics (amoxicillin and ampicillin) at a concentration of 300 µg/mL was used for the seeding. Then, a 1 cm$^2$ fresh mycelial agar disc previously grown in PDA solid medium was seeded at 25° C. for 7 days. Finally, the plates were incubated at 28° C. for 7 days. Mass plates were made in different culture media: i) Potato Dextrose Agar (PDA, Sigma-Aldrich, USA), ii) Sabouraud Dextrose Agar (SB, Sigma-Aldrich, USA), iii) Malt Extract Agar (MEA, Sigma-Aldrich, USA), iv) Rose Bengal (RB, Sigma-Aldrich, USA) and, v) Czapek Dox Agar (Cz, Sigma-Aldrich, USA). Given the exclusive genetic characteristics of each strain, their growth parameters and their nutritional requirements could vary between each one, so different nutrient sources were evaluated to know with which formulation each strain shows optimal kinetics of growth (Table 3, FIGS. 5A-5B).

Tolerance of Antibiotics to Mitigate Bacterial Contamination During Bioprocess

Strains may also be selected based on their ability to tolerate one or more antibiotics. To prevent bacterial contamination in the mass plate, it may be helpful to add antibiotics to the culture media. Therefore, the effect of different concentrations of antibiotics on the growth of the working fungal strains may be evaluated. For example, a completely randomized design (CRD), consisting of 6 treatments with five repetitions each, with eighteen (18) experimental units, was done. Each experimental unit consisted of a Petri dish with 20 mL of SB medium with a specific concentration of antibiotics (amoxicillin and ampicillin). The treatments were designated as: 1) 20 mL of SB medium in each Petri dish (control); 2) 20 mL of SB medium supplemented with 0.1 mg of amoxicillin and 0.1 mg of ampicillin; 3) 20 mL of SB medium with 0.2 mg of amoxicillin and 0.2 mg of ampicillin; 4) 20 mL of SB medium with 0.3 mg of amoxicillin and 0.3 mg of ampicillin; 5) 20 mL of SB medium with 0.4 mg of amoxicillin and 0.4 mg of ampicillin and; 6) 20 mL of SB medium supplemented with 0.5 mg of amoxicillin and 0.5 mg of ampicillin. Prepared dishes were autoclaved for 20 min at 121° C. and 15 psi and allowed to cool to room temperature. The antibiotic solutions were added to the culture medium according to the concentrations described above for each treatment and dispensed in a Petri dish (inside a horizontal laminar flow hood). Subsequently, an agar disk with fresh mycelium of 1 cm$^2$ previously grown in solid PDA medium at 25° C. for 7 days was seeded in the center of the plate. Finally, the plates were placed in an incubator at 28° C. for 7 days. After 7 days, measurements of colonization of mycelium in the plates were carried out by analyzing the corresponding photographs with the ImageJ Software. The data obtained were statistically processed using R with a significance level of $\alpha=0.05$. The tested fungal strains used in this assay were 0000, 0002, 0006, 0013, 0014, 0023, 0028, 0037, and 0046. FIG. 6A describes the concentration of antibiotics at which the various tested fungal strains were able to tolerate after 7 days of incubation (e.g., 300 µg/mL of Amoxicillin and 300 µg/mL of Ampicillin).

The concentration that the fungal strains can tolerate using ciprofloxacin, amoxicillin, and ampicillin together was also determined. For this, the experiment mentioned above was carried out with the following modification: the concentrations of amoxicillin and ampicillin were maintained in the medium at a final concentration of 300 µg/mL, while the concentration of ciprofloxacin was varied. The treatments were the following: 1) 20 mL of SB medium in each Petri dish; 2) 20 mL of SB medium supplemented with 0.3 mg of amoxicillin, 0.3 mg of ampicillin, and 0.1 mg of ciprofloxacin; 3) 20 mL of SB medium supplemented with 0.3 mg of amoxicillin, 0.3 mg of ampicillin and 0.2 mg of ciprofloxacin and; 4) 20 mL of SB medium supplemented with 0.3 mg of amoxicillin, 0.3 mg of ampicillin and 0.3 mg of ciprofloxacin. FIG. 6B describes the concentration of the antibiotic pool at which the tested fungal strains can tolerate after 7 days of incubation (e.g., 300 µg/mL, 300 µg/mL, and 100 µg/mL of Amoxicillin, Ampicillin, and Ciprofloxacin, respectively).

Induction of the Degradation of the Plant Cell Wall Biopolymers

The saprophytic extracellular multi-enzymatic system that degrades lignocellulosic biomass of lignocellulosic fungi may be activated depending on the type of nutrients in the culture medium and the availability of carbon and energy sources. The methods and compositions described herein may supplement the culture media with organic growth inducers, including a lignocellulosic component (cellulose, hemicellulose, and lignin) and a protein component (corn, wheat, sawdust). Applying different growth inducers may strengthen the physiological conditioning of the extracellular oxidative enzymatic machinery required to efficiently degrade structurally complex and recalcitrant carbohydrates in the pre-fermentation (pre-inoculum substrate) and fermentation (production substrate) stages.

A fungal strain may be screened to determine the strain's effectiveness with a growth inducer. For example, growth inducers may include one or more of: i) wheat grains; ii) grams of corn, and iii) sawdust. In some examples, they may be ground in the grain grinder and subsequently sterilized in an autoclave and supplemented at a final concentration of 1% (w/v).

A completely randomized design (CRD) was carried out with the tested strains, consisting of 7 treatments with two repetitions each, with fifteen (16) experimental units. The treatments were the following: 1) Sawdust (A); 2) Wheat (T); 3) Corn (M); 4) Sawdust/Wheat (A/T); 5) Sawdust/corn (A/M); 6) corn/wheat (M/T); 7) Sawdust/corn/wheat (A/T/M) and; 8) the control (without organic inducer). Once the media supplemented with growth inducers to be studied were autoclaved, the antibiotics ampicillin and amoxicillin were added (300 μg/mL) to avoid bacterial contamination, and 20 mL of each medium was added to each of the Petri dishes. Next, a 1 $cm^2$ agar disc colonized by the fungus understudy was seeded in the center of each mass plate. Once the plates were seeded, the Petri dishes were incubated at 28° C. for 6 days. Photographs were taken on the third and sixth days of incubation. The percentage of colonization at the plaque level was measured using ImageJ software with the captured images. FIG. 7 illustrates the results among all the organic inducers studied, showing the best growth inducer for each strain examined.

Morphological and Structural Description of the Mycelium

The fungal strands may be morphologically examined, e.g., to confirm that the mycelium has a highly fibrillar morphology and hyphae diameter within a desired range. For example, the fibrillar morphology of their mycelium may be selected to have a hyphae diameter greater than about 1 μm (e.g., between about 1.0±0.3 to 1.6±0.5).

Figure 8:
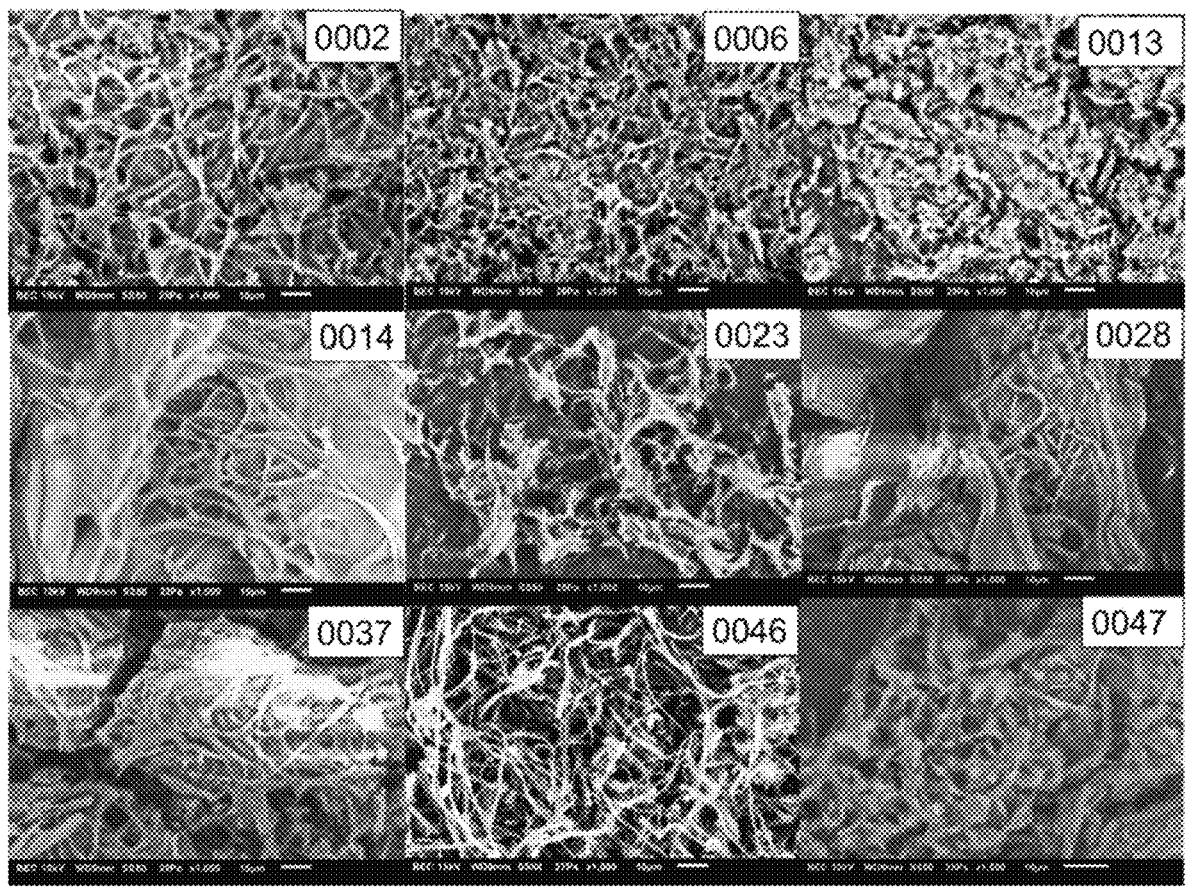
FIG. 8 shows scanning electron microscopy images of examples of fungal strains screened as described herein.

For example, the putative strains described above were examined using a JEOL brand scanning electron microscope, model 6010 Plus, in image collection mode with secondary electrons. The lyophilized mycelium was deposited in aluminum supports covered with carbon tape to prevent its detachment during analysis. The images were collected using an accelerating voltage of 15 kV and a magnification of 1000×. FIG. 8 shows a representative image of each fungal strain with which the mycelium development in each fungal strain examined can be compared. Strains 0002, 0006, 0023, and 0046 showed hyphae with the best fibrillar development, with diameters close to 1 m with good length. Strains 0013 and 0047 strains did not show fibrillar development but rather revealed an amorphous morphology. In contrast, strains 0014, 0028, and 0037 showed a mixture of thin and elongated fibers with other amorphous and larger structures. The values measured for the average diameter of the hyphae for strains 0002, 0006, 0014, 0023, and 0046 strains are indicated in FIG. 13, below, along with other characteristics. In this example, fungal strains 0002, 0006, and 0046 showed a fibrillar morphology of their mycelium. Therefore, these strains may be selected as part of the methods of manufacturing a mycotextile (e.g., mycotextile).

Chemical Composition of the Mycelial Cell Wall

Any of these methods may include determining at least a partial indication of the chemical composition of the fungal strain, including the chemical composition of the fungal wall. In particular, these methods or compositions may include the percentage of chitin and/or the type of chitin. For example, the cell wall composition of a fungal strain may be determined by extracting proteins and sugars in water, followed by the extraction of soluble glucans in 1 M aided with ultrasonic radiation (35 KHz) to speed up the process. In one example, both the initial solids and the residues were evaluated by Fourier transform infrared spectroscopy in attenuated total reflectance mode (ATR/FTIR) to identify the characteristic functional groups of each strain.

Figure 9A:
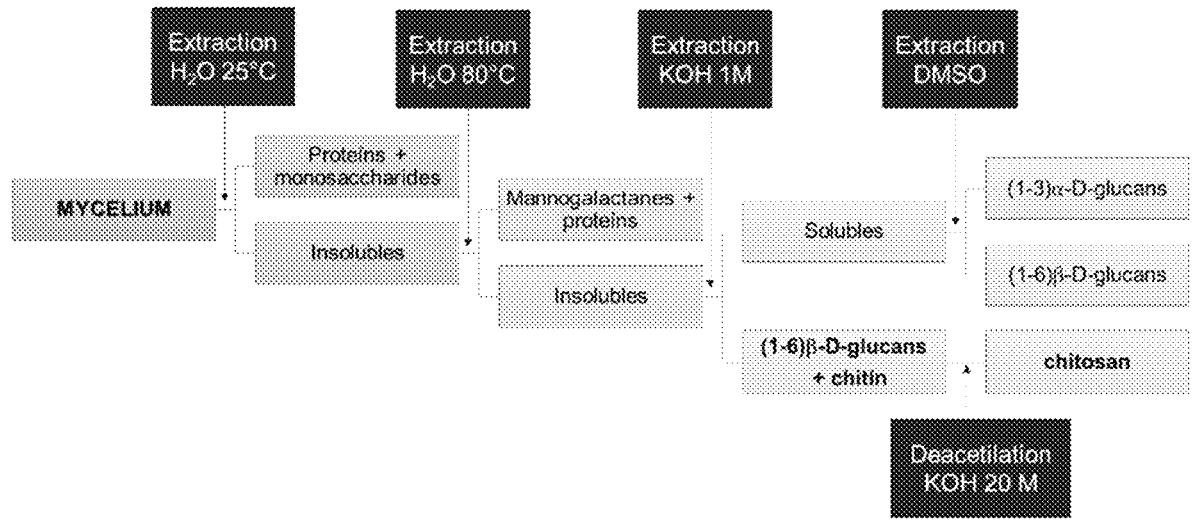
FIG. 9A schematically illustrates one example of a procedure for polysaccharide extraction of a fungal strain as described herein.
Figure 9B:
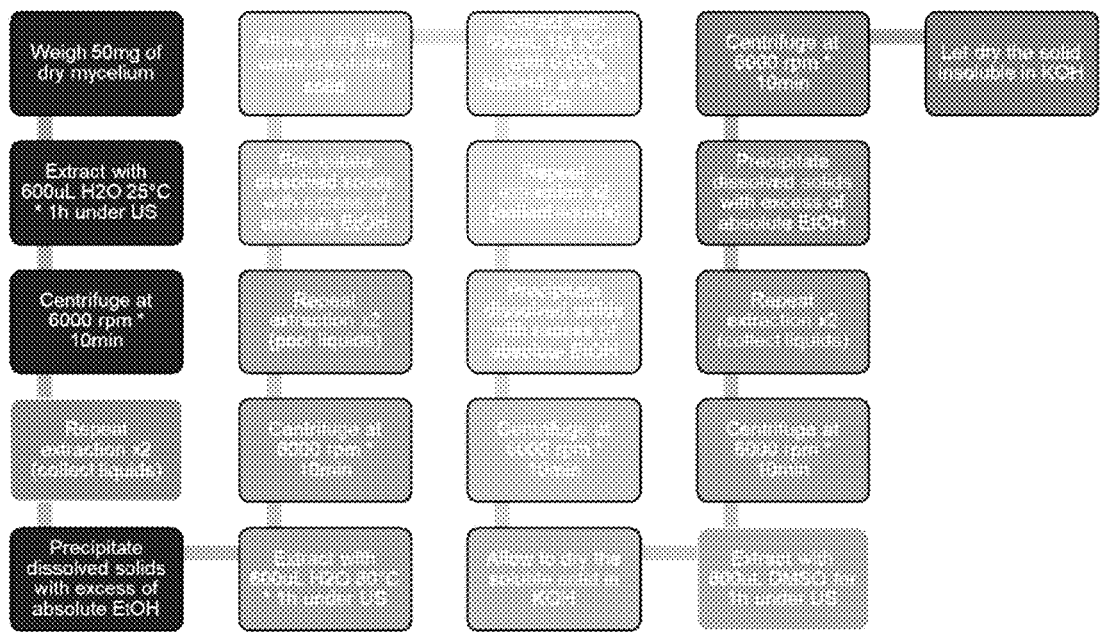
FIG. 9B schematically illustrates another example of an outline of a polysaccharide extraction protocol that may be used as described herein (e.g., to determine the amount and/or type of chitin).

For example, as a reference experiment, the residue of one of the strains of interest (0006) was selected for treatment with 20 M KOH to deacetylate the amide groups of the chitin present in the residue. The general scheme is shown in FIG. 9A. FIG. 9B schematically illustrates a more specific example.

Figure 10:
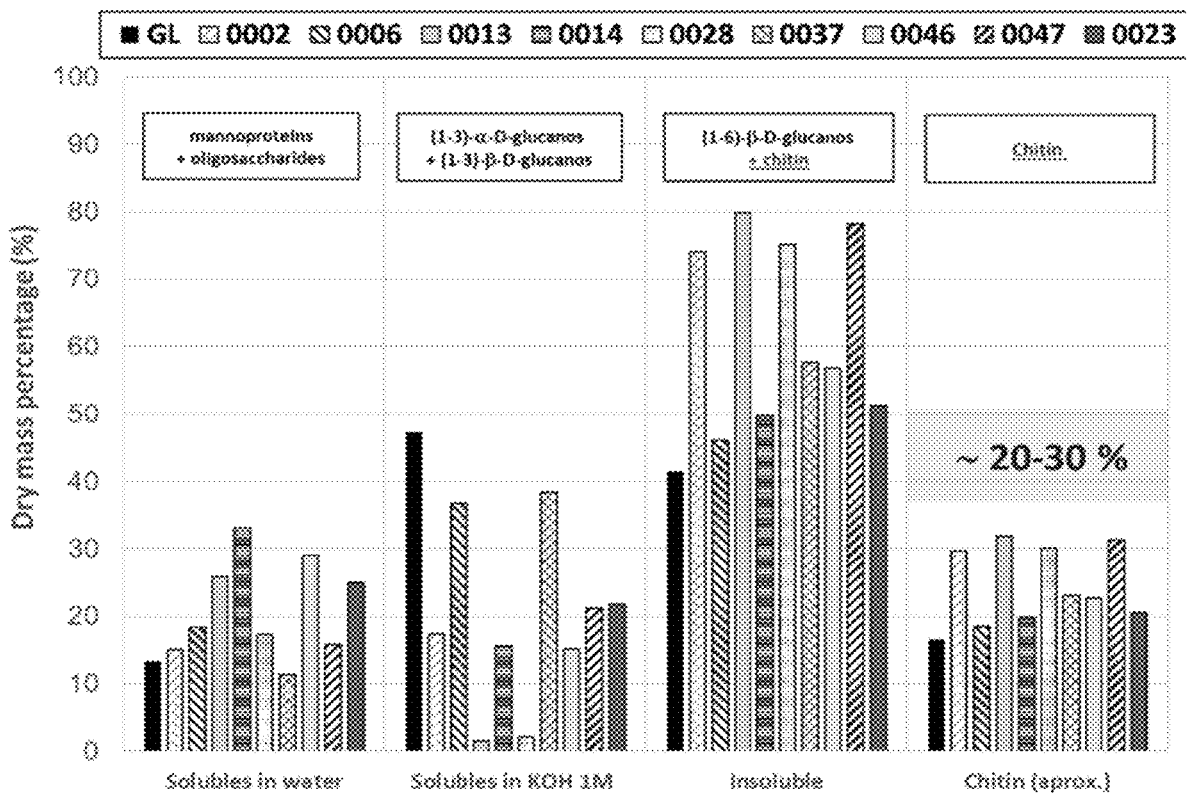
FIG. 10 is a graph illustrating the distribution of proteins, oligosaccharides, polysaccharides (glucans), and chitin fractions of 9 potential fungal strains plus the commercial strain *G. lucidum* SB-0000 used as control.

In this example, water extraction was performed to quantify: (a) cold-water-soluble proteins and monosaccharides and (b) hot water-soluble proteins and manogalactans. As shown in FIG. 10, 0014 strain revealed the highest proportion of this fraction, 33% of the dry weight. Meanwhile, the 0037 strain presented 11.4%, being the lowest value within the analyzed group; that is, this strain has a lower proportion of sugars and proteins of a hydrophilic nature. Subsequently, the (1-3)-α-D and (1-6)-β-D-glucans extracted in a caustic solution of KOH 1 M were found in greater proportion in 0037 strain, representing 38% of its weight. In this case, 0013 and 0028 strains have only 1.6 and 2.1% dry weight, respectively.

The remaining solid fraction is of great interest because it contains the (1-6)-β-D-glucans and chitin. The chitin polymer may be a target component for cross-linking as described herein (e.g., nanoparticle cross-linking) and may provide structural rigidity to the cell wall. In this example, it was observed that the 0013 strain has about 80% insoluble solid, while the 0006 strain has 46% by weight. The percentage of chitin shown in the last section of the graph is an estimate considering a 60:40 ratio of glucans:chitin in the insoluble fraction. Considering the values of the control strain *G. lucidum* SB-0000, we can see that it has a higher proportion of polysaccharides soluble in KOH than the selected strains. At the same time, the percentage of insoluble solids is slightly lower than for the 0006 strain, which indicates that if the relationship between (1-6)β-D-glucans and chitin were similar in all these species, the control strain would be at a disadvantage regarding chitin content, which represents a differentiating characteristic of the target fungal strains that may be used in some examples described herein.

Figure 11:
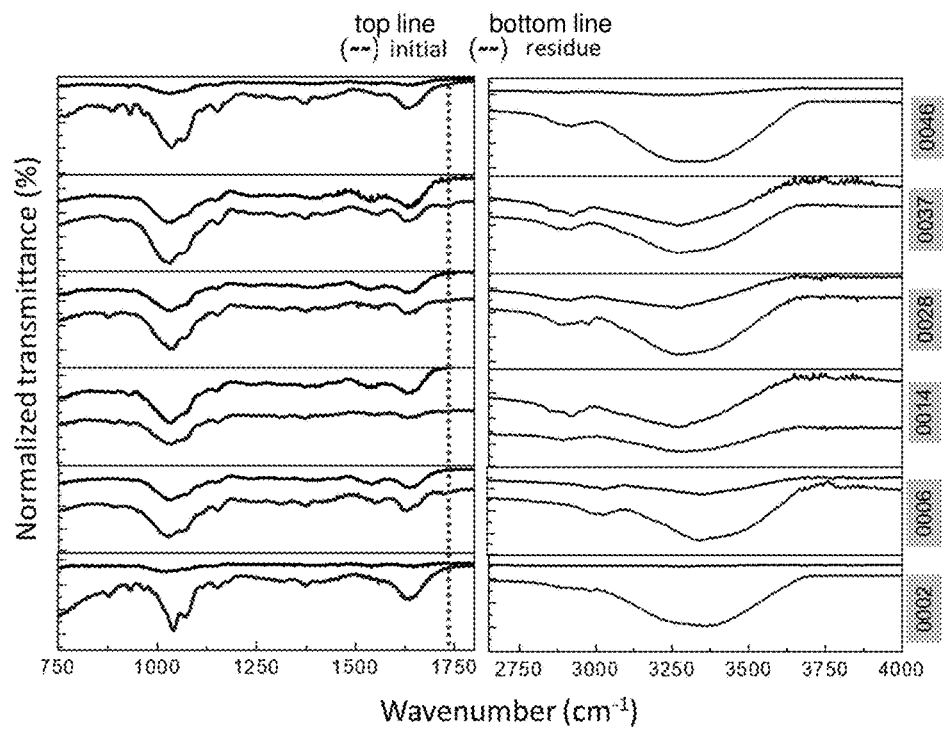
FIG. 11 is a graph showing infrared spectra of the fungal test strains (upper/top lines) and the insoluble fraction after extraction with water and KOH 1M (lower/bottom lines).

Spectroscopic characterization of the six selected strains in this example was performed (shown in FIG. 11) by measuring the ATR/FTIR spectrum before (upper lines) and after (lower lines) polysaccharide extraction. The normalized spectra are shown in FIG. 11 and were divided into two regions, one from 2700 to 3800 $cm^{-1}$ and the second from 500 to 1700 $cm^{-1}$. In the first region (between 2700 and 3800 $cm^{-1}$), the following signals can be observed: the OH bond stretching band appears around 3300 $cm^{-1}$ in 0002, 0006, and 0046 strains and near 3270 $cm^{-1}$ for 0014, 0028, and 0037 strains. After polysaccharide extraction, the band is more intense and wider for the first-mentioned strains. The apparition of a second peak suggests that there are two contributions to the signal. These peaks appear at 3250, 3240, and 3245 $cm^{-1}$ for 0002, 0006, and 0046 strains, respectively. Stretching vibrations for NH bonds in amido groups ($CONH_2$ or CONRH) also appear between 3200 and 3300 $cm^{-1}$ in primary amides or secondary amides, respectively. So, we could infer that in strains 0002, 0006, and 0046, the amido groups (most probable secondary amides) are more exposed after the polysaccharides extraction. Next, characteristic bands at 2953, 2918, 2873, and 2850 cm$^{-1}$ correspond to the symmetric and asymmetric stretching of the ethylene (—CH$_2$) and methylene (—CH$_3$) groups, respectively. After the polysaccharide extraction, the normalized signals are more intense for 0002, 0006, 0028, and 0046 strains. In the second region (between 500 and 1700 cm$^{-1}$) appear other characteristic bands of the biopolymers conforming to the cell wall. Around 1630 cm$^{-1}$, a peak of medium intensity can be observed in all cases, which is attributed to the stretching of the carbonyl bond (C═O) in the amido groups that appears approximately at the same wavenumber for all cases and is that expected for associated secondary amides (e.g., chitin). The relative intensity of this band increases markedly in 0002 and 0046 strains after polysaccharide extraction, suggesting that chitin is more exposed in these strains. In the case of 0006, 0037, and 0046 strains, a small shoulder around 1700 cm$^{-1}$, which becomes more visible after extraction, suggests the presence of another type of carbonyl compound.

The position of this additional carbonyl band could be associated with the presence of an anhydride or an ester group. Because of the persistence of the band after harsh treatments under basic conditions and ultrasonic radiation, it is likely that this group belongs to polysaccharide existing in the cell wall. An example is the β-(1,4)-D-Polyglucuronic acid existing in some fungi cell walls. These are polysaccharides containing carboxyl groups that could be present and could also be partly esterified as methyl esters. The presence of carboxylic groups is consistent with the additional contribution to the O—H stretching band discussed above. The presence of other chemical reactive groups other than chitin/chitosan is highly desirable to increase crosslinking options. Thus, any of the fungal strains described herein may be selected as being enriched for β-(1,4)-D-Polyglucuronic acids in the fungi cell walls, which would be present in the final product (e.g., as part of the crosslinked mycelium layer). Thus, any of the compositions described herein may include β-(1,4)-D-Polyglucuronic acids within the crosslinked mycelium layer(s) forming the material (e.g., 0.1% or greater of the polysaccharides within the mycelium layer(s), 0.2% or greater, 0.5%, or greater, 0.7% or greater, 1% or greater, 2% or greater, 5% or greater, etc.).

The band near 1540 cm$^{-1}$ assigned to the bending vibration of the NH band in secondary amides appears with greater intensity in 0006, 0014, 0028, and 0037 strains. The bands around 1400, 1370, and 1270 cm$^{-1}$, of weak intensity, are present in all strains and correspond to bending vibrations of OH, CH, and CN bonds, respectively. The most intense band around 1030 cm$^{-1}$ is assigned to COC stretching of the biopolymers (glycosidic linkage), while the shoulder at 1070 cm$^{-1}$ is attributed to COH stretching in primary alcohols. Finally, the bands at 970, 930, and 880 cm$^{-1}$ are assigned to CH bond bending vibrations and appear with greater intensity in 0002 and 0046 strains.

Figure 12A:
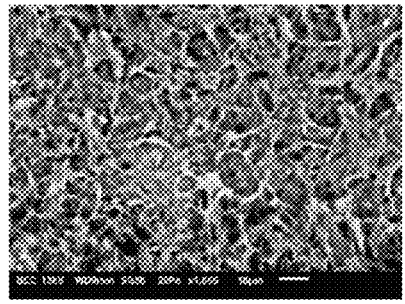
FIGS. 12A-12G show SEM images for one example fungal strain (e.g., the 0006 strain): fresh (FIG. 12A), after polysaccharides extraction (FIG. 12C), after treatment with KOH 20 M (FIG. 12E). Images for control strain *G. lucidum* SB-0000 are shown for fresh (FIG. 12B), after polysaccharides extraction (FIG. 12D), and after treatment with KOH 20 M (FIG. 12F). ATR/FTIR spectra for the residue after the treatment with KOH 20M are shown in FIG. 12G. The spectrum of the initial strain is shown at the top of each group.
Figure 12B:
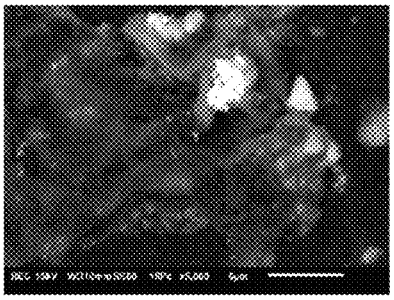
Figure 12C:
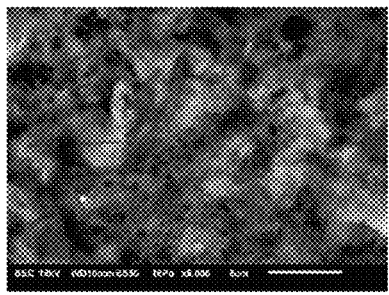
Figure 12D:
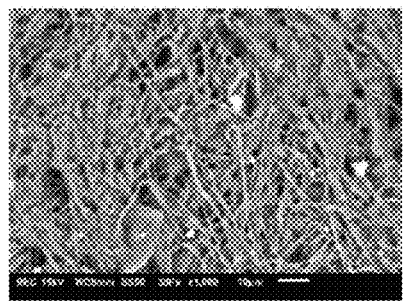
Figure 12E:
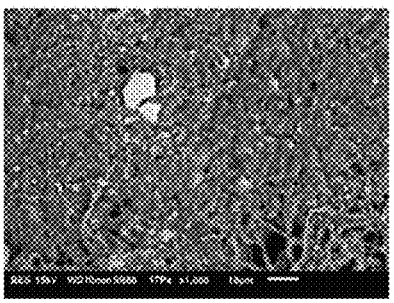
Figure 12F:
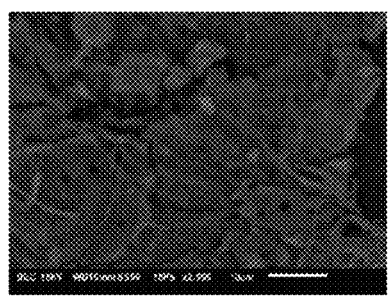

Comparing the effect of the treatment on the morphology of the mycelium for the example of one strain (e.g., wild fungal strain 0006, shown in FIG. 12A) versus the control strain *G. lucidum* SB-0000 (FIG. 12B), it can be seen in the SEM images that a remarkable change in the morphology occurs in both cases. For the 0006 strain, after polysaccharide extraction, the distribution of hyphae is lost, and the structure becomes amorphous (FIG. 12C). The treatment with a higher base concentration (e.g., 20 M) increases this effect leading to a more porous structure (FIG. 12E). For *G. lucidum* SB-0000, the structure is not completely lost after polysaccharides extraction (FIG. 12D). However, the treatment under harsh conditions also transforms the mycelium network (FIG. 12F). This change in morphology suggests that aggressive deacetylation strategies affect cell wall structure, which could be reflected in a lower mechanical resistance of the mycelium. Therefore, finding new approaches to increase the mechanical resistance without affecting the structure is essential.

Figure 12G:
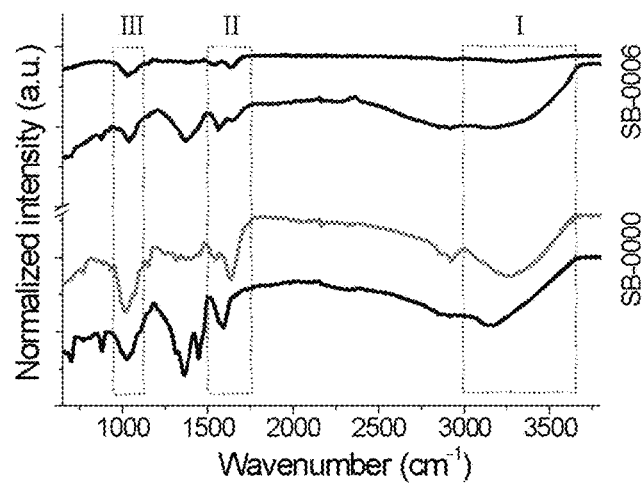

The ATR/FTIR spectra of the solids obtained after the treatment with KOH 20 M are compared in FIG. 12G. Three regions could be highlighted to confirm chitin deacetylation to obtain fungal-chitosan. First, between 3000 and 3300 cm$^{-1}$, related to the stretching vibration of O—H and N—H bonds. A shift to lower wavenumbers was observed after the treatment, which could be related to the obtention of the primary amine. The example 0006 strain (as one example of a fungal strain having characteristics that may be used to determine a desired fungal strain) shows a broader band, suggesting the presence of adsorbed water which could be related to a more hydrophilic surface or the contribution of another O—H group, as for example from a carboxylic acid. The second region used to confirm the chitin to chitosan transformation is between 1500 and 1700 cm$^{-1}$, where C═O stretching and N—H bending vibrations appear; both groups constitute the amide moiety in chitin. As observed in the bottom spectra of each group, the intensity of the band around 1640 cm$^{-1}$ decreased, suggesting the loss of the C═O bond. Moreover, the band around 1540 cm$^{-1}$ is shifted to a higher wavenumber related to the amide (OCNHR) to amine (RNH$_2$) transformation. The band around 1700 cm$^{-1}$ in 0006 appears slightly shifted to lower wavenumber but is absent in the control sample, indicating that the control *G. lucidum* SB-0000 lacks additional reactive carbonyl moieties. Finally, the bands highlighted in region III, around 900 and 1200 cm$^{-1}$, remain unaltered, indicating that the backbone of the polysaccharide is not altered after the deacetylation (the procedure does not cause depolymerization). Therefore, the morphological change observed in SEM images could be merely a mechanical effect after the US irradiation.

Phenotypic Characterization of Fungal Strains Based on the Growth

In any of the compositions and methods described herein, the interaction between the mycelium and the support (layer/scaffold) may be modulated by including one or more chemical moieties that may be introduced to favor the interaction between both components, considering the organic nature of the scaffold. In this regard, polycarboxylic and polyphosphate groups may be used to achieve this specificity in the chemical interaction. Both compounds may allow the development of interactions by hydrogen bonds (citric acid) or electrostatic (sodium polyphosphate) with the polysaccharides present in the cell wall in a way that guarantees the "fixation" of the hyphae to the cellulose fibers of the layer/scaffold. In any of these methods and compositions, the fungal strain may be selected based on the tolerance of the fungal strain to citric acid and sodium polyphosphate.

Tolerance to Citric Acid

The methods described herein may also include determining the tolerance of the fungal strains (including wild fungal strains) to citric acid, such as having a tolerance between about 1 to 20%, preferably between about 1 to 10%, preferably between about 2 to 5%. For example, the activation of the layers/scaffolds may be determined, e.g., by immersing for 1 hour in solutions containing different concentrations of citric acid: 0%, 2%, 4%, and 6% w/v. In one example, once the time had elapsed, samples were dried in a convection oven at 180° C. for 30 minutes. Subsequently, a circular piece of the activated layer/scaffold with a diameter of 85 mm was placed on a solid culture medium in each Petri dish (90 mm in diameter), and an agar disc of 1 cm² with fresh mycelium previously grown on solid medium (PDA at 28° C. for 7 days) was seeded. Finally, the plates were placed in an incubator at 28° C. for 14 days. Mycelial colonization measurements were made on the plates through photographs and ImageJ Software on days 7 and 14. The data were statistically processed using R and the Levene, Shapiro-Wilks, and Kruskal-Wallis tests with a significance level of $\alpha=0.05$. The results obtained (FIG. 13) show that all the promising fungal strains can tolerate citric acid up to 2% w/v. It should be noted that, for the functionalization of the layers/scaffolds in the development of a mycotextile (e.g., mycotextile) as described herein, the concentration of citric acid to prepare depends on the tolerance of each fungus according to the information provided in the table shown in FIG. 13. To prepare a 2% w/v solution, 16 g of citric acid are added to 800 mL of distilled water and autoclaved for 35 minutes at 121° C. and 15 psi.

Tolerance to Sodium Polyphosphate

The methods described herein may also include determining the tolerance of the fungal strains (including wild fungal strains) to sodium polyphosphate, such as having a tolerance between about 1 to 20%, preferably between about 1 to 10%, preferably between about 2 to 5%. To activate the layers/scaffolds with polyphosphate groups, the fabrics (e.g., layers/scaffolds) were immersed for 1 hour in solutions with different concentrations of sodium polyphosphate: 0%, 2%, 4%, and 6% w/v. Once the time had passed, they were dried in a convection oven at 180° C. for 30 minutes. Subsequently, a circular piece of layer/scaffold with a diameter of 88 mm was placed on a solid culture medium in each Petri dish (90 mm in diameter), and an agar disc with fresh mycelium of 1 cm² previously grew in the PDA medium at 28° C. for 7 days) was seeded. Finally, the plates were placed in an incubator at 28° C. for 14 days. At 7 and 14 days, mycelial colonization measurements were made on the plates using photographs and ImageJ Software. The data were statistically processed using R and using the Levene, Shapiro-Wilks, and Kruskal-Wallis tests with a significance level of $\alpha=0.05$. The results obtained (FIG. 13) show that most of the promising fungal strains can tolerate sodium polyphosphate up to 2% w/v, except for 0023 and 0047 strains, which are highly susceptible to this compound.

Preparation and Seeding of Pre-Inoculum Substrates.

As part of the pre-fermentation process, any of the methods described herein may include generating a pre-inoculum substrate colonized with the selected fungal strain. The pre-inoculum is a substrate that is used as a nutritional vehicle to promote efficient and effective colonization. It allows it to scale towards other selective substrates and in greater quantity for productive purposes. The pre-inoculum may be made up of sterilized grains that provide the nutrients and growth conditions necessary for the mycelial development of fungi. Among the most common grains used in this phase may include one or more of: i) wheat, ii) rice, iii) sorghum, iv) rye, v) millet, and vi) corn. Any of these may be used individually or in combination. The selection may depend on the available agro-industrial wastes or local agri-productive areas (e.g., near or adjacent to the production plant) and the nutritional requirements of the selected fungal strain. Also described herein are methods that may act as standards for obtaining pre-inoculum of a fungal strain that may be appropriate for the other methods described herein.

For example, described herein are methods for forming pre-inoculum from solid-state fermentation substrates (SSFS). In some cases, the substrate may be based on the type of fungal strain used. Thus, any of these methods may include identifying the type of pre-inoculum solid-state substrate. For example, to determine the type of substrate that promotes the best mycelial growth for 0000, 0013 and 0028, 0014, and 0002 strains in the pre-inoculum substrate, the grains were soaked for 24 hours, renewing the water every 12 hours. Subsequently, the excess water was drained off, and 200 g of grains were placed inside each polyfoam bag (8"×12"), and each bag was autoclaved for 35 min at 121° C. and 15 psi.

In one example, a completely randomized design (CRD) was carried out, consisting of 3 treatments with five repetitions, each with a total of fifteen (15) experimental units. Each experimental unit consisted of a polyfoam bag with 200 g of grains (corn, wheat, or oats) soaked for 24 hours and drained inside. Treatments were designated as: 1) corn, 2) wheat, and 3) barley. Four agar disks with fresh mycelium of 1 cm² previously grown in solid PDA medium at 25° C. for 7 days were placed inside each bag (using a horizontal laminar flow hood). Finally, the bags were placed in an incubator at 28° C. for 14 days. Every 7 days, from the beginning of the experiment, colonization measurements were carried out using photographs and the ImageJ Software. The data were statistically processed using R with a significance level of $\alpha=0.05$. the table of FIG. 14 shows the type of grain in which each fungal strain grows best after 7 days of incubation. It is observed that both corn and wheat reach 100% colonization for all of the strains tested.

In general, to mitigate undesirable contamination of bacteria or fungi, a cleaning protocol for the selected grain (e.g., FIG. 14) may be used as a 2×2 physical and chemical pretreatment. A first step of rinsing the grain with water was performed to remove any impurity or unwanted particulates. The excess water was drained off, and the grains were sterilized in an autoclave for 45 minutes at 121° C. and 15 psi. Then, they were soaked for 12 hours in a 5% v/v chlorine solution (first chemical treatment) with stirring every hour to ensure the homogeneity of the treatment. Subsequently, these grains were washed with abundant water, ensuring that no trace of chlorine could affect the growth of the fungus in the following phases. Then, the grains were immersed in a 2% w/v lime solution for 12 hours with periodic stirring (second chemical treatment). As in the previous case, it was rinsed with abundant water and allowed to drain until excess water was eliminated.

Once the chemical pretreatment was performed, 500 g of grains were weighed in each bag and subjected to a second sterilization in an autoclave for 45 minutes at 121° C. and 15 psi. After this, it was allowed to cool to room temperature. The prepared grains were then used to form the pre-inoculum substrate. The grains may be seeded with the fungal strain to be used. For example, each of the example strains described above was seeded in the pre-inoculum substrate. For this, fresh mycelial agar sections of 1 cm² were placed inside the pre-inoculum bag. The mass plate was prepared with 7 days of growth in a modified SB culture medium supplemented with a pool of antibiotics. Each mass plate was sufficient to prepare two 500 g bags (forming the seeded pre-inoculum substrate). Finally, the substrate was homogenized, labeled, and left to incubate in the dark at 28° C. for 7 days.

As an alternative to the grains used as pre-inoculum (due to its higher risk of contamination), a liquid culture medium Potato Dextrose Broth (PDB, Sigma Aldrich, USA), may be used to promote mycelial growth. In some examples, 5-10 sections (1×1 cm$^2$) of agar colonized by vegetative mycelium for 7 days were dissected from a fresh mass plate and inoculated in an Erlenmeyer flask with 100 mL of PDB culture medium supplemented with an antibiotics pool (Amoxicillin 100 mg/mL and Ampicillin 100 mg/mL). The nozzle of each flask may be covered with a gauze and cotton plug so as not to cut off the gas exchange with the outside.

Various liquid pre-inoculum substrates were tested against different fungal strains. For example, flasks with the liquid culture medium were incubated in an orbital shaker at 28° C. and 250 rpm for 7 days to promote gas exchange and mycelial growth in the culture broth and mycelial fractionation. Qualitative estimation using a range from nothing (−) to higher growth (++++): (the scale was the following: −, +, ++, +++ and, ++++) were made to evaluate both the kinetics of mycelial growth and the homogeneity of colonization in the culture media studied.

In some examples, growth in either the solid or liquid substrate may be used as another parameter for selecting the fungal strain to be used. For example, in relation to the kinetics of mycelial growth, 6 strains had a higher growth (++++) including: 0006/010221/SS/BF, 0014/010221/SS/BF, 0018/020221/SM/EW, 0038/010320/SS/BF, 0045/120621/CU/MY and 0047/120621/CU/BF. While 9 strains had slower growth kinetics (+++): 0007/010221/SS/BF, 0011/010221/SS/BF, 0013/010221/SS/BF, 0020/020221/SM/BF, 0023/020221/SM/BF, 0028/020221/SM/BF, 0037/010320/SS/BF, 0039/010321/SS/BF, and 0042/120621/CU/BF.

Homogeneity of growth may also or alternatively be used as a parameter for selecting the fungal strain to be used. For example, In relation to the homogeneity of the mycelial colonization, 6 strains had a greater homogeneity (++++) in the medium: 0006/010221/SS/BF, 0007/010221/SS/BF, 0011/010221/SS/BF, 0018/020221/SM/EW, 0045/120621/CU/MY and 0047/120621/CU/BF. While 8 strains had homogeneity of (+++): 0013/010221/SS/BF, 0014/010221/SS/BF, 0023/020221/SM/BF, 0028/020221/SM/BF, 0037/010320/SS/BF, 0038/010320/SS/BF, 0039/010320/SS/BF, and 0042/120621/CU/BF.

The strains that showed growth kinetics and colonization homogeneity with the highest range (++++) for both parameters include: 0006/010221/SS/BF, 0018/020221/SM/EW, 0045/120621/CU/MY, and 0047/120621/CU/BF. In this example, the potential fungal strains with growth kinetics and/or colonization homogeneity of (++++) or better may be selected to produce a fungal-derived textile (e.g., mycotextile). These characteristics may be of particular interest for the development the fungal-derived textile, since it represents an alternative to replace the use of pre-inoculum based on solid-state fermentation substrate (SSFS) in the Pre-fermentation stage, which contributes to improving efficiency in production processes, pollution mitigation, as well as time reduction in bioprocesses.

In any of the methods and apparatuses described herein, an inducer composition may be included. For example, organic inducers may be used to activate the enzymatic system of plant cell wall biopolymer degradation and promote mycelial vigor for mycotextiles purposes, as described in greater detail below. The table in FIG. 15 illustrates qualitative information about the growth kinetics of some examples of fungal strains described herein, as well as the homogeneity of colonization in said culture medium.

Fermentation Stage

Following the completion of the pre-fermentation stage, the seeded pre-inoculum (which may be referred to herein as the inoculum) may be used as part of the fermentation process. In general, the fermentation process may be configured as described herein to occur over a period of less than 14 days, and more particularly, less than 10 days, less than 9 days, less than 8 days, etc., which is considerably faster than previously described fermentation methods.

For example, described herein are methods for fermenting (growing the fungal-based material from the inoculum) by preparing and seeing a production substrate. As described herein, a production substrate may include a lignocellulosic source, such as sawdust and chips, and a nitrogen source, such as wheat, corn, barley, sorghum, among others, formulated to ensure an approximately (or in some cases, exactly) 40:1 carbon to nitrogen ratio and approximately a 70% of moisture content. The sawdust and shavings may be used from, e.g., byproduct lumber materials (in some examples, the sawdust and shavings came from the same trees from which the example fungi were isolated). The organic substrates used to prepare the production substrates in some example were derived from: Tamburo (*Vochysia leguiana*), Cedar (*Cedrela odorata*), Laurel (*Cordia alliodora*), Chuncho (*Cedrelinga cateniformis*), Huarango (*Prosopis pallida*), Jacaranda (*Jacaranda copaia*), Pehuén or Araucanian Pine (*Araucaria araucana*), Star Pine (*Araucaria angustifolia*), Pino Insigne (*Pinus radiata*) and Pigie (*Piptocoma discolor*), among others. In one example, the proportion of sawdust and chips as a lignocellulosic source and of wheat, corn, barley, sorghum, among others, as a source of nitrogen, where the best colonization of vegetative mycelium with the fungi studied was obtained included approximately 73.125% Sawdust (from a lignocellulosic source) and 24.375% wood chips (from the same or a different lignocellulosic source), and 2.5% whet or corn (e.g., nitrogen source).

A chemical pre-treatment similar to that used for the pre-inoculum substrate may be used for the production substrate to eliminate environmental contaminants and any endophytic microorganism associated with the lignocellulosic source. For example, the sawdust and chips may be soaked in a 2% (w/v) in lime solution for 24 hours. Similarly, grains of wheat or corn were treated with the pretreatment mentioned above (for the pre-inoculum substrate). After rinsing the lignocellulosic substrate with water, it may be drained and air-dried. Subsequently, the nitrogen source may be added (e.g., wheat, corn, barley, sorghum, etc.), homogenized, and weighed in bags of 750 g each. Immediately, the production substrate may be sterilized for 135 minutes at 121° C. and 15 psi. It is allowed to cool to room temperature, and 500 g of pre-inoculum colonized with fresh mycelium previously incubated at 28° C. for 8 days (e.g., inoculum), as described above, may be placed in each production substrate bag to obtain a total weight. 1,250 g per bag. Finally, the inoculated production substrate is homogenized and incubated in the Growing Room at 28-30° C. for 8-14 days. Once this time has elapsed, and with high colonization and free of contamination, the production substrate will be ready for foam fabrication as described herein, which may be referred to herein as BIOrganic foam fabrication (or simply "bio-organic foam").

The foam fabrication method described herein may be used to scale-up the fungal-derived textiles production using a hybrid fermentation substrate (HFS), which may include an activated scaffold, as will be described below. The comparative advantages of the foam fabrication techniques described herein as compared with conventional techniques include a greater homogeneity of the substrate since the same nutritional and microclimatic conditions are supplied to the fungus throughout the surface/growth support where the foam is deposited. The foam fabrication techniques described herein may also provide a more uniform and vigorous aerial mycelium growth. The aerial mycelium is distributed more uniformly and reproduces with greater vigor when it is fractured. These form fabrication techniques may also reduce contamination, which is a main obstacle in the bioprocesses for growing fungal materials, since the substrate has a 90-100% colonization of the fungus and, by fracturing it, secondary metabolites and antibiotics are generated that inhibit the growth of bacteria and other fungi. The bio-organic foam manufacturing technique described herein may also ensure efficiencies and reproducibility in the prototyping processes and scalability. Using a semi-solid substrate may make automation more manageable and less expensive, including additive manufacturing of micromaterials. The foam manufacturing techniques described herein also increase production capacities and reductions in production time, while using the same fewer materials, equipment, and man-hours.

In general, the foam fabrication methods described herein may include the use of a production substrate bag that is combined with the pre-inoculum substrate that has been seeded with the selected fungal strain. Thus, the fermentation techniques described herein may include the preparation and production of the substrate bag(s). The foam may then be formed from the substrate bag, e.g., by blending/homogenizing the substrate bag with a proportioned amount of water, glycerol (or other polyglycols, e.g., polyethylene glycol and polypropylene glycol, also other compounds, such as polyalkylene oxides, or polyadipates), and (optionally) an activator. The resulting foam may be grown on a sterile, releasable (e.g., mesh) support, flattened, and incubated to allow growth. During the growth period, an activated scaffold/layer may be added, and the material may be permitted to continue to grow on the scaffold, incorporating the activated scaffold/layer.

The production substrate bags may be used to form the foam material with a colonization percentage of 90 to 100%, which may be reached in a growth period of between 8 and 14 days, depending on the fungus used. The mass of the rest of the foam components may be estimated from the weight of the colonized production substrate, e.g., according to a predetermined set of proportions, such as those illustrated in the table below, table 1. In some examples, the component proportion may be as described in the example percentage (and/or example weight); in others, the proportion may vary within the indicated example range.

TABLE 1

Components of BIOrganic Foam Mixture

| Component | Example Weight (g) | Example range (%) | Example Percentage (%) |
|---|---|---|---|
| Production substrate colonized | 1000 | +/−10% | 46.4 |
| Glycerol 96% (or other polyglycols, e.g., polyethylene glycol and polypropylene glycol, also other compounds, such as polyalkylene oxides, or polyadipates) | 167.6 | +/−4% | 7.7 |

TABLE 1-continued

Components of BIOrganic Foam Mixture

| Component | Example Weight (g) | Example range (%) | Example Percentage (%) |
|---|---|---|---|
| Activator (e.g., casein solution or MARILLION) | 262.9 | +/−5% | 12.2 |
| Distilled water | 723.8 | +/−7% | 33.6 |
| Total | 2154.3 | | 100 |

All of the components may be blended, e.g., by placing them in an industrial blender. The colonized production substrate may be blended first, and then the 96% v/v glycerol (or other polyglycols, e.g., polyethylene glycol and polypropylene glycol, also other compounds, such as polyalkylene oxides, or polyadipates), activator (e.g., casein solution or MARILLION activator), and distilled water may be added to complete the mixture. All of the components of the mixture (glycerol, activator, and distilled water) may be previously autoclaved, and one or more compounds included for example, the distilled water may contain 0.1-1% calcium oxide (CaO) and a pool of antibiotics (amoxicillin and ampicillin) at a concentration of 300 µl/mL to eliminate possible bacterial contamination.

Figure 16:
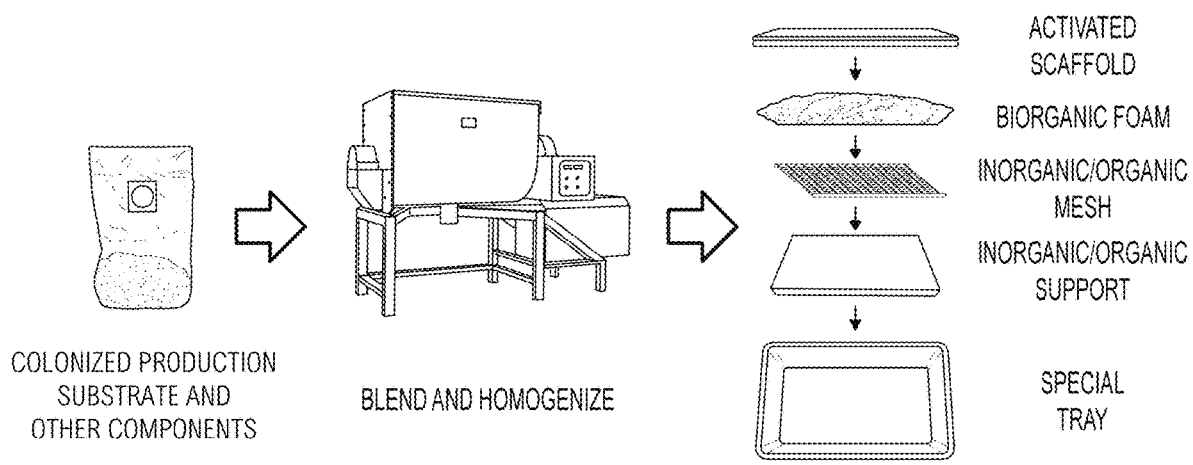
FIG. 16 illustrates one example of a process flow for fermentation (e.g., using the form fermentation technique described herein).

Once the mixture is mechanically disaggregated and homogenized for 5 to 10 minutes using the industrial blender, under sterile conditions, the resulting foam material may be placed onto inorganic or organic support. For example, the support may be a 2.5 to 5.0 cm thick polyurethane support or an organic support (e.g., luffa, coconut fiber, jute fiber, among other vegetable fibers) to absorb any excess of moisture. The foam material may be applied in a 5 to 20 kg/m² ratio or more with a thickness of, e.g., between about 0.5 to 2.5 cm. FIG. 16 schematically illustrates this fermentation (BIOrganic foam) technique. The inorganic support can be recovered and reused as needed to avoid the generation of polluting waste. The support may be held in an inorganic or organic support tray. The tray, support, and mesh system may be assembled in a kit inside a polypropylene cover, which may have been previously autoclaved, e.g., for 180 minutes at 121° C. and 15 psi, to eliminate any possible contaminating agent. In some examples, the kit can be sterilized by exposure to UV light and ozonation for 1 hour. Once the foam material is added to the mesh support, its surface may be flattened manually or using a vibrating plate. Finally, the trays are incubated (e.g., in a grow room) at about 28-30° C., in the dark, with fresh air ventilation and 99-100% relative humidity for between 2 to 5 days before placing the activated layers/scaffolds onto the foam material. The timing of the addition of the activated layer/scaffold may depend on the candidate fungus used (in particular, the growth rate) and the components used to manufacture the foam, including the activator. For example, table 2 (below) illustrates examples of the timing before adding the activated layer/scaffold. The data in Table 2 illustrates differences in mycelial growth by day according to foam components. In general, the data shows that when an activator is used, such as casein or MARILLION, the number of days of incubation required to obtain a dense and profuse mycelial growth before the addition of the activated substrate is reduced by more than half (e.g., from 5 days to 2 days) and the number days required after addition of the activated substrate is significantly reduced as well (from 9 days to 7 days). Thus, the total number of days required to incubate the foam material prior to harvesting is reduced from 14 to 9 when using an activator, regardless of the amount of nitrogen, from 2.5% nitrogen source to 25% nitrogen source.

TABLE 2

Differences of days in mycelial growth according to components of BIOrganic Foam

| Variations on the components | Number of days of incubation required to obtain dense and profuse mycelial growth (# days) | Number of days of incubation required after layer/scaffold placement (# days) | Number of total days of incubation required to harvest the mycotextiles (# days) |
|---|---|---|---|
| Addition of casein in Production Substrate with 25% nitrogen source | 2 | 7 | 9 |
| Addition of casein in production substrate with 2.5% nitrogen source | 2 | 7 | 9 |
| No addition of casein in production substrate with 25% nitrogen source | 5 | 9 | 14 |
| No addition of casein in production substrate with 2.5% nitrogen source | 5 | 9 | 14 |

Thus, if the foam contains an activator such as casein solution, a two-day incubation period is sufficient before placing the chemically activated layer/scaffold. If no activator (e.g., casein solution) is added to the mix, the trays should be incubated for about 5 days before layering/scaffolding. Likewise, if the mixture has an activator, 7 days of incubation will be required after placing the layer/scaffold to harvest the mycotextiles, while without the activator solution, the trays should be incubated for about 9 days before harvesting.

The chemically activated scaffolds described herein may be fabric or non-fabric materials. In general, the chemically activated scaffold may be alternatively and equivalently referred to as an activated layer or activated fabric, or reinforcement layer, reinforcement scaffold or reinforcement fabric. In some examples, the activated layer is configured as a support fabric that supports the growth of the aerial mycelium. The activated layer may include multiple reactive groups that bond to the chitin within the mycelium and may also provide mechanical support. The activation of the layer may be essential to prevent delamination of the final material from the layer. It may dramatically improve the mechanical characteristics of the material, as described herein. In some examples, a high resistance material (e.g., activated layer or scaffold) is formed of a plant-based fiber, such as cotton or jute, with a tensile strength value of between 280 and 800 MPa. However, in practice, such plant-based textiles may decrease their tensile strength over time, as reported for prior versions of mycelium leather, which typically have a tensile strength of between 0.8 and 12.5 MPa.

Alternatively, the activated scaffold/layer may be formed of a complex fiber such as a glass fiber (GF), carbon fiber (CF), or polyaramid fiber (PAF), each of which has remarkable mechanical properties. These fibers may be used as mechanical reinforcement for the fungal-based fabrics described herein. In general, these fibers may be referred to as non-plant fibers or synthetic fibers (e.g., glass, carbon and/or polyaramid fibers). Tensile strength values using non-plant fibers (e.g., synthetic fibers) may range between 2000 and 4000 MPa.

In general, the activated layer comprising a non-plant-based fiber (such as a glass, fiber, a carbon fiber and/or a polyaramid fiber) may be incorporated from continuous yarns and a sewing machine as a first approximation. The incorporation of the thread can be done in various patterns such as square mesh, honeycomb, or zigzag to optimize reinforcement in different directions of the fabric. Likewise, the reticulation degree can be varied to increase the effect. For example, this reticulation could be changed by varying the diameter of the repeating units, which would increase the number of repeating units per unit area.

Activated scaffold material (e.g., the activated non-plant, such as activated glass fiber, carbon fiber, and/or a polyaramid fiber) may be applied as a sheet onto the foam, as shown in FIG. 16 (e.g., after between 2-5 days of incubation of the foam material. The sheet of material may have an open pore arrangement and may include very small pores (e.g., less than 5%, 4%, 3%, 2%, 1%, 0.5%, 0.1%, etc. of the open). The sheet of material may include a pattern (honeycomb pattern, square pattern, etc.) and may be woven, knit, braided, etc. The material may be activated as described in more detail below. The material may be formed of a filament or bundle of filaments. The filaments may have an appropriate diameter, such as between 0.01- and 1-mm diameter (e.g., between 0.01 mm and 0.5 mm diameter, between 0.05 and 0.5 mm diameter), etc.

In some examples, the fiber (non-plant fiber) may be sewn or stitched into the material instead of or in addition to adding it during the foaming procedure as described above. For example, incorporating a 0.18 mm diameter glass fiber by following a bioinspired honeycomb pattern of 1024 units per $m^2$ caused a 43% decrease in tensile strength from the original fabric and a 55% drop in elongation percentage before the break. A higher density of repeating units (4096 units per $m^2$) reduced only 7% in tensile strength. A square lattice pattern with the same density of repeating units decreased the tensile strength by 1%. All this indicates that other options for incorporating GFs in the layer should be explored to observe the desired effect on resistance. Both the reticulation degree and the pattern play a significant role in the property evaluated.

For example, a carbon fiber with a fiber diameter of 0.2 mm may increase tensile strength when a piece of cotton fabric is used as a substrate material. In this example, the cotton fabric's tensile strength may increase by about 23% and may decrease elongation by about 11% when introducing 4096 repetitive units per $m^2$. This example has a value of 20.3 MPa and an elongation of 21.2%.

Figure 17:
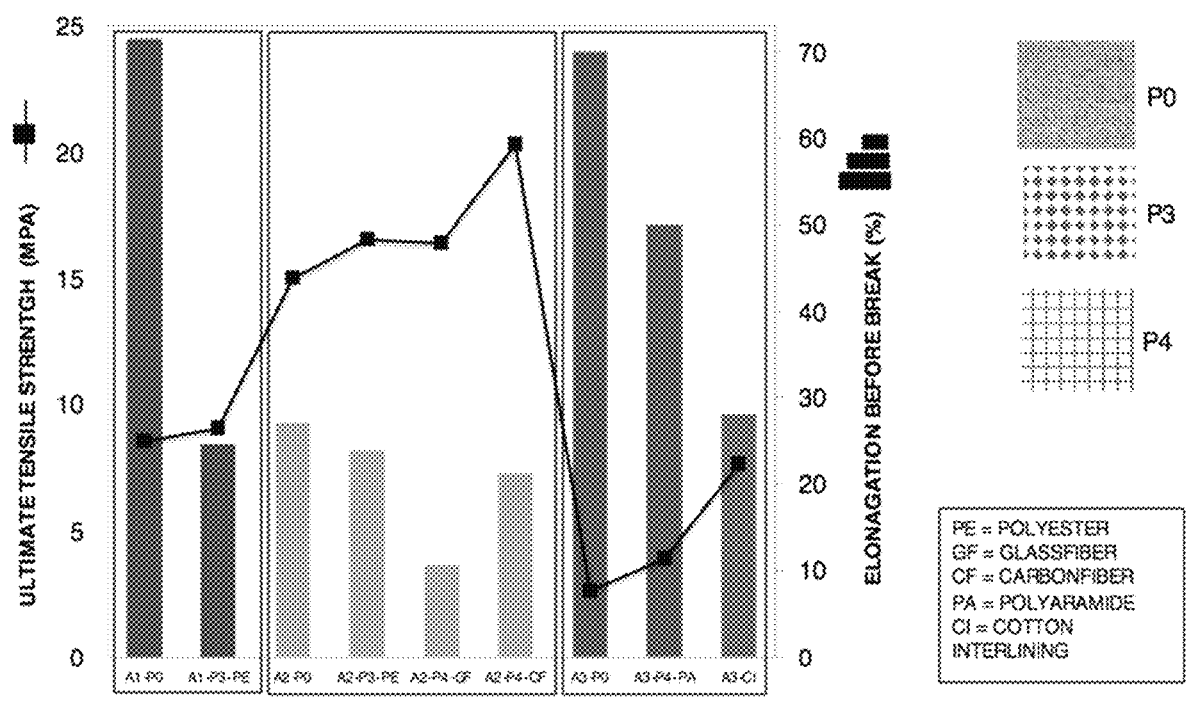
FIG. 17 is a graph showing a comparison of the tensile strength and elongation values (reinforced fabric) and the vegetable fabric used as a layer.

In other examples, polyaramid fiber increased in 32.56% of a raw cotton fabric having an initial tensile strength of 2.63 MPa by introducing 4096 repetitive units per $m^2$. This thread also diminishes the elongation from 70 to 50%. Cotton interlining with a mesh pattern as described above increased the tensile strength up to 7.6 MPa and diminish the elongation to 28%. FIG. 17 illustrates examples of the tensile strength and elongation values for various scaffolds compared to non-reinforced layers.

The interaction between the support fabric and the growing mycelium layer could be modified by suitable functionalities chemically related to the polymers/biopolymers present in both the scaffolding (e.g., cotton, etc.) and the mycelium to avoid detachment of the mycelial layer from the support layer/scaffold. Thus, the methods and compositions (e.g., mycotextiles or mycotextiles) described herein may generally include a support scaffold/layer that is chemically activated to increase this binding. For example, vegetable support scaffold/layers (such as cotton) may be chemically activated with citric acid or sodium polyphosphate before forming the scaffold (e.g., with one or more synthetic fibers as inorganic reinforcements). As can be seen in FIG. 18, in the case of incorporating the citric acid, the functionalization may be confirmed by the appearance of the signals corresponding to the stretching vibrations (v) and deformation (p) of the carboxyl group (COO$^-$) of citric acid when comparing a cotton substrate to a modified (activated) cotton substrate. As used herein, the terms "activated" and "functionalized" may refer to the inclusion of reactive groups configured to bind with cell wall material (e.g., chitin).

Following the first 2-5 days of mycelial growth on the BIOrganic foam material, the support layer/scaffold (e.g., activated and/or reinforced) may be placed onto the growing foam material, which in one example, has been activated with 2% citric acid. The placement of the layers/scaffolds may be done uniformly, gently pressing the sheet on the mycelium with a roller and avoiding the formation of air bubbles between both parts. The tray may be incubated under the same conditions described.

In some examples, the MARILLION activator is a mixture of A and B solutions. For example, to prepare solution A, each component described in the table below (table 3) may be weighed and made up to 998 mL with distilled water.

TABLE 3

Components and solutions to prepare solution A

| Component | Chemical formula | Example amount or volume |
| --- | --- | --- |
| Ammonium nitrate | $NH_4NO_3$ | 1.2-2.4 g |
| Urea | $CO(NH_2)_2$ | 0.41-0.82 g |
| Calcium chloride | $CaCl_2$ | 1.00-2.00 g |
| Magnesium sulphate heptahydrated | $MgSO_4*7H_2O$ | 1.00-2.00 g |
| Monopotassium phosphate | $KH_2PO_4$ | 5.00-10.00 g |
| Glycerol | $HOCH_2-CHOH-CH_2OH$ | 50-100 mL |
| DI-water | $H_2O$ | 446-892 mL |

This recipe may be used to prepare 1 liter of MARILLION solution. In some examples, 100 mL of solution B may be prepared according to the formula detailed in the table below (Table 4).

TABLE 4

Components and solutions to prepare solution B

| Component | Chemical formula | Example amount (g) |
| --- | --- | --- |
| Iron (II) sulfate heptahydrate | $FeSO_4*7H_2O$ | 0.499-0.998 |
| Zinc sulfate heptahydrate | $ZnSO_4*7H_2O$ | 0.220-0.440 |
| Manganese (II) chloride tetrahydrate | $MnCl_2*4H_2O$ | 0.05-0.101 |
| Cobalt (II) chloride hexahydrate | $CoCl_2*6H_2O$ | 0.016-0.032 |
| Copper (II) sulfate pentahydrate | $CuSO_4*5H_2O$ | 0.015-0.031 |

Once both solutions are ready, 2 mL of solution B may be placed in 998 mL of solution A, obtaining a final volume of 1000 mL. The activator described in this example may be referred to as the MARILLION activator. Finally, the solution may be sterilized for 35 minutes at 120° C. and 15 psi and placed in a sterile atomizer to evenly distribute it over the layers/scaffolds (or may be added to the production substrate, as described above).

Any of the methods described herein may include, e.g., as part of the fermentation (including the foam) technique, a change in the microclimatic incubation conditions (e.g., in the Growing Room), for example, after the placement of the activated layers/scaffolds. In some examples, the temperature (e.g., 28-30° C.), darkness, and 99-100% relative humidity may remain the same. However, the $CO_2$ concentration may be increased to 20,000-50,000 ppm within 48-72 hours after the activated layer/scaffold is placed. The growing mycelium may therefore have enough time to colonize the layer/scaffold before applying the high concentrations of $CO_2$ which may displace the oxygen in the growth chambers, resulting in faster and more uniform growth.

After complete incubation, following the addition of the activated scaffold/layer and incubation period, the putative mycotextile may be removed from the tray. A spatula may be used to separate the foam from the support mesh for this operation. Subsequently, the material may be dried, e.g., in a convection oven for 15 minutes at 60° C. and then exposed to UV light for 15 to 20 minutes to inactivate the fungus and to continue the post-fermentation stage.

Post-Fermentation

After the fermentation stage, when the aerial mycelium has formed below, above, and between the support layer/scaffold (which in some examples may be activated), the resulting material may be treated to form a resistant mycelium textile. These post-fermentation treatment steps mainly involve hydration, crosslinking to provide greater mechanical strength (usually carried out using vegetable tanning schemes), pressing, drying, and in some cases, embossing. Also described herein are methods that include the addition of nanoparticles. In some examples, the nanoparticles may be added during the fermentation stage or during both the fermentation stage and post-fermentation stages. Some or all of these post-fermentation treatments may be performed. In some examples, the post-fermentation stage(s) may depend on the fungal strain, or the process parameters used.

Any of these methods may include the use of a plasticizing agent. In some examples, suitable results may be obtained in appearance by using only glycerol as a plasticizing agent. However, further processing steps may be useful to prevent brittleness and the loss of internal moisture. Besides, additional processing may dramatically increase the durability of the resulting material; durability may allow more environmentally friendly materials that are also highly functional.

In some examples, the post-fermentation stage may include one or more (or all of): (1) internal wetting, (2) nano-crosslinking; (3) pressing (which may include embossing); (4) activation with mordant; (5) dyeing; and (6) external humidity barrier (plasticizing).

Development of a Formulation for Internal Wetting

Any of the methods described herein may include increasing the internal wetting of the hyphal network by incorporating one or more additives that may increase flexibility. The compositions may be referred to as internal wetting compositions or humectants (internal humectants). These internal wetting compositions may include a vegetable oil and, a surfactant or a surfactant blend and, water. In some examples are vegetable oils (as fatliquoring agents), such as sulfated castor oil, beeswax, coconut oil, olive oil, linseed oil, oleic acid, sulfated fish oil, sulfated canola oil, soybean oil, palm oil, fatty acids, etc., may be included or incorporated as a moisturizer.

Some examples described herein are humectant formulations developed to transport soybean oil using a polysorbate with HLB between 15 and 16.7 as an emulsifying agent. In general, the emulsion mixture should remain stable over time (e.g., longer than 24 h) without separating, and should prevent detachment of the mycelium from the support layer/scaffold and should not dry out over time. An example of a soybean-oil based mixture includes soybean oil (e.g., 12% p/p), tween 20 (e.g., 12% p/p), water (e.g., 70% p/p), and glycerol (e.g., 6% w/w). The emulsion presented good fluidity but low stability (approx. 24 h). Despite good fluidity and the increase in the wetting of the prototypes, a detachment of the mycelium was observed in some areas. The solubilization of some cell wall components is caused because of the composition, affecting its adherence to the support layer/scaffold.

Some examples described herein comprises coconut oil-based O/W emulsions using surfactant blends to achieve HLB values of approximately 8. A matrix was made based on the HLB values and possible proportions of each candidate component. The calculation was made in first approximation as: HLB final=(% A×$HLB_A$)+(% B×$HLB_B$)+(% C×HLBc) . . . , some examples may include polysorbates with HLB between 15 and 16.7, e.g., Tween 20, Tween 60 or Tween 80 and, a surfactant with HLB between 3.8 and 6.7, such as, sorbitan oleate (Span 80), sorbitan stearate (Span 60) or glyceryl monostearate (GMS).

Some examples described herein use a surfactant blend of Tween 20 (HLB of 16.7), and GMS (HLB of 3.8). A mix of 30% Tween 20 and 70% GMS was initially chosen. Oil/surfactant (O/S) and water/oil (W/O) ratios were varied. The compositions evaluated herein showed a single phase. The selection was based on empirical criteria such as the fluidity of the mixture and stability (a single milky phase). Examples of mixtures examined included 30% Tween 20 and 70% GMS, and 50% Tween 20 and 50% GMS. A general procedure for the preparation of each mixture is the following: each component is weighed separately. The water was mixed with the surfactant with higher HLB and heated to about 80° C. The surfactant with the lower HLB and the oil phase was mixed and brought to an equal temperature than the aqueous phase. The oily phase was transferred to a container for mixing under high shear force (e.g., 15,000 rpm/min). The aqueous phase was slowly added slowly. Constant stirring continued for 5 min. A proper mixture should be fluid, milky in appearance, and homogeneous (no phase separation). Some examples of proper mixtures presented as references are shown in Table 5, below: ("O", Coconut oil), 2% surfactant blend ("S", a mixture of 50:50 Tween 20 and GMS), and 78% water ("W").

TABLE 5

O, S, W proportions to prepare emulsions

| X | O (% w/w) | S (% w/w) | W (% w/w) | O/S | W/O |
|---|---|---|---|---|---|
| 1 | 40 | 10 | 50 | 4 | 1 |
| 2 | 29 | 7 | 64 | 4 | 2 |
| 3 | 20 | 5 | 75 | 4 | 4 |
| 4 | 10 | 5 | 85 | 2 | 9 |
| 5 | 20 | 5 | 75 | 4 | 4 |

TABLE 5-continued

O, S, W proportions to prepare emulsions

| X | O (% w/w) | S (% w/w) | W (% w/w) | O/S | W/O |
|---|---|---|---|---|---|
| 6 | 20 | 2 | 78 | 10 | 4 |
| 7 | 5 | 2 | 93 | 2.5 | 19 |

Thus, the methods described herein may include using an internal wetting composition, including those described herein that include a combination of vegetable oil (e.g., coconut oil), a surfactant blend, and water, in which the oil is between 5-40% w/w, the surfactant is between 2-10% w/w, with water making up the difference (e.g., between 50-93%). The surfactant may be a combination of a non-ionic surfactant with high HLB (e.g., Tween 20, Tween 60, Tween 80) and a fatty acid ester (e.g., Span 60, Span 80, glyceryl monostearate) in a ratio of between about 40%-60%, 30%/70% (e.g., 50%/50%). These internal wetting compositions may be particularly well suited and formulated specifically to the fungal-derived textiles described herein.

The internal wetting composition may be applied to the material's surface following fermentation and before further processing. In some examples, internal wetting using the emulsion composition (e.g., the internal wetting composition described herein) may be achieved by soaking the mat of material for approximately 30 min, followed by drying up to 20% of humidity, preferably between 20 and 50%. The volume used for the treatment may depend on the putative fabric surface. For example, the minimum volume used for treatment may be about 1.5 to 2.5 L/$m^2$ for fabrics with about 1 to 2 mm of thickness, respectively. For example, between 1-2 L/$m^2$ of internal wetting composition may be used for every 1 mm of the thickness of the material (prior to compression).

In some examples, the material may incorporate 20 wt. % of coconut oil in the internal wetting composition emulsion, with 78 wt. % of water and 2 wt. % of the surfactant blend (e.g., 1% of tween 20 and 1% of glyceryl monoestearate (GMS) or 0.6% of Tween 80 and 1.4% of Span 80). Outside of the range of compositions described herein, the internal wetting composition may result in phase separation (i.e., oil and aqueous phases), a very high viscosity, or a low stability over time (e.g., low shelf-life). In general, coconut oil may be optimal, as different types of oil or other amounts of coconut oil (outside of the specified range) may require a particular composition because the hydrophilic to lipophilic balance (HLB number) will change. The principal component is the water to obtain an oil-in-water emulsion (O/W). This value may depend on the other components (e.g., it may be adjusted but should be above 50 and below 100 wt. %). To obtain a liquid and fluid emulsion, the oil incorporated into the micelles should be below 30 wt. % to obtain a liquid and fluid emulsion; a minimal value is above 0%. However, as mentioned before, each concentration of coconut oil may be optimized for the mixture composition. The oil-to-surfactant ratio (O/S) may be between 4 and 10. The surfactant blend may be around 2 to 5 wt. % to avoid increasing the viscosity. The droplet size of a typical mixture containing the Tween 80 and Span 80 blend (as the example 7 in Table 5) is around 3.27 μm, measured using a Malvern Mastersizer 2000 instrument. The effect on the hyphae includes swelling and coating according to SEM images.

Any of the fungal-derived textiles described herein may be formed by including an additional crosslinking step following fermentation (e.g., post-fermentation). Although animal-derived textiles such as leather may be crosslinked using vegetable tanning agents, such agents may be ill-suited for the fungal-derived textiles described herein and/or may result in an undesirable amount of waste and industrial byproducts. Conventional crosslinking consists of an inter-action scheme by hydrogen bonds using polyphenolic molecules of plant origin. The use of natural tanning is a widely used strategy in the leather industry.

Such conventional tanning techniques may be used; preliminary tests showed that the mycotextiles described herein may be submerged for 5 to 7 days in 2% w/w tannic acid solution. As seen in the scanning electron microscopy image of FIG. 19, taken of a prototype material prepared with a commercial strain of G. lucidum (SB-0000), the treatment with tannic acid causes compaction of the hyphae in the most superficial levels of the mycelial layer (FIG. 19A). FIG. 19B shows that the mycelial layer (in the outermost areas of the material) is slightly separated from the layer/scaffold located in the center of the material, suggesting that the mycelial layer is detaching from the supporting textile (delamination) in this example.

Figure 20:
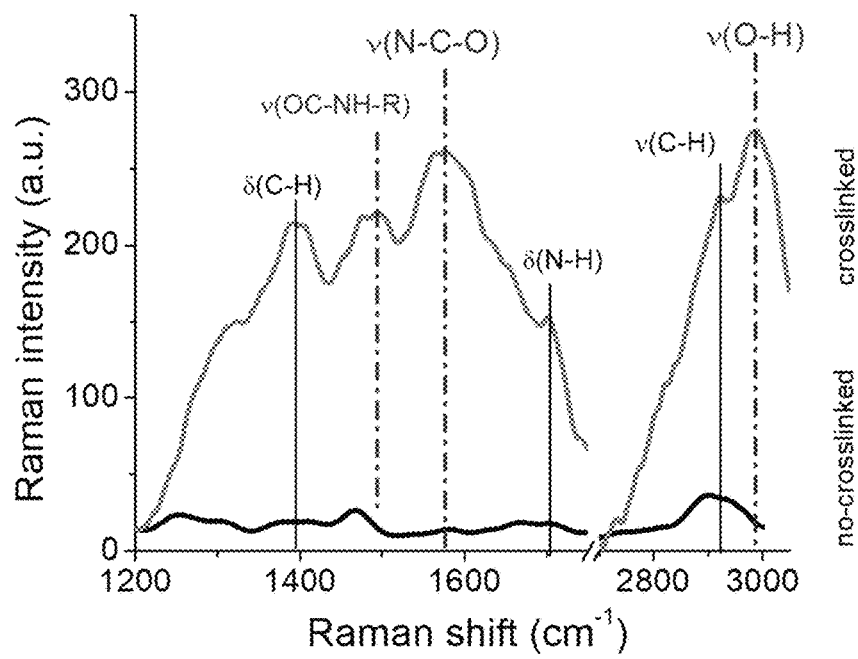
FIG. 20 shows an example of a Raman scattering spectrum of the sample material shown in FIGS. 19A-19B both without crosslinking (lower black color) and after crosslinking with tannic acid (upper gray color).

FIG. 20 shows an example of a Raman scattering spectrum of a material such as that shown in FIGS. 19A-19B, showing the chemical changes experienced by the "control" (non-optimized) fungal strain G. lucidum (SB-0000) after crosslinking with tannic acid. The bands at 1490 and 1580 $cm^{-1}$ are characteristic of the amide groups from the chitin group involved in the crosslinking are shown highlighted in the dot-dashed lines. Meanwhile, the appearance of signals around 3000 $cm^{-1}$ (stretching of the OH bond) evidenced the presence of phenolic groups from the tannic acid used as a crosslinking agent. The tensile strength values achieved after applying this strategy were considerably higher. However, this treatment appears to cause delamination of the mycelial layer, as reflected in the microscopy images. This means that this strategy is very efficient in achieving crosslinking and hyphae but may be too aggressive for the final aesthetic characteristics.

Nanoparticle Crosslinking

Surprisingly, the inventors have found that including nanoparticles within the fungal material may dramatically and unexpectedly enhance the stability and mechanical properties of the fungal-derived textiles described herein, including the tensile strength and modulus as well as the tear strength and abrasion resistance. Functionalized nanoparticles may be added to the material following fermentation. The functionalized nanoparticles may be selected to crosslink with the cell wall material readily and controllably, e.g., chitin (or chitosan). This crosslinking strategy may include incorporating reactive functionalities via the inorganic nanoparticles, which, in addition to functioning as a carrier (crosslinking bridge), can impart other characteristics such as thermal stability due to their inorganic nature. Moreover, nanoparticle-assisted crosslinking may provide greater versatility by adsorbing functional interest groups on these nanoparticles.

The use of functionalized nanoparticles provides several advantages when controlling the crosslinking process and may be modulated by controlling variables such as the density of functional groups on the nanoparticles, the number of nanoparticles (carrier), and the size of the nanoparticles, etc. The size of the nanoparticles may be modified during formation, e.g., by varying the stoichiometric ratios between the reagents, which will allow control of the separation between the hyphae. The shape of the nanoparticles may also be selected, including spherical, non-spherical, ovoid, filamentous, non-filamentous, rod, sickle, etc.

The crosslinking agent used with the nanoparticles can be modified depending on the chemical functionality of the cell wall, which in turn may depend on the fungal strains used. This may allow unprecedented advantages in tailoring the fungal-derived textile's cross-linking strategies. Additionally, incorporating functionalized nanostructures may provide novel qualities to the material, such as magnetism, fluorescence, fire resistance, and/or mechanical resistance, among others.

Figure 21:
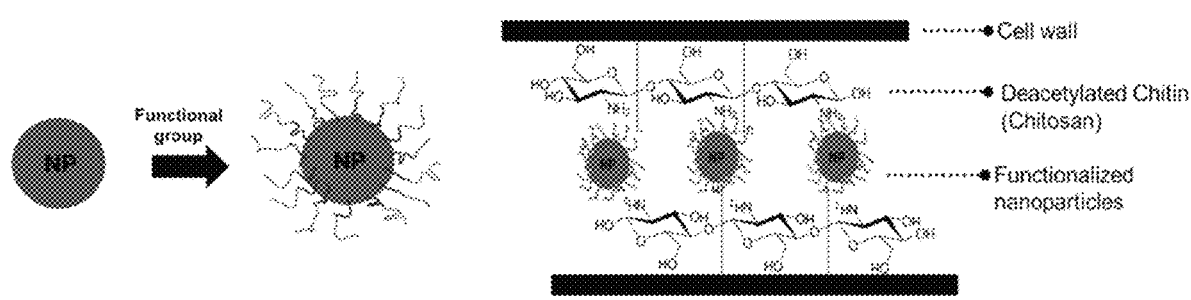
FIG. 21 schematically illustrates one example of a crosslinking technique using nanoparticles; in this example, $SiO_2$ nanoparticles as shown as a model of functionalized nanoparticles and the interaction with the amino groups of the deacetylated chitin.

FIG. 21 schematically illustrates one example of a nanoparticle, showing functionalization and incorporation into a mycotextile as described herein. In FIG. 21 the nanoparticle (NP) is shown as a spherical silicon oxide ($SiO_2$) nanoparticle. Such particles may be prepared by the Stöber-Fink-Bohn method, described below. In this example, nanoparticles (nanospheres) of 500 nm were functionalized with (3-aminopropyl triethoxy) silane (APTES) to confer amino terminations on the surface. These moieties allow altering the surface charge through variations in the pH of the medium where they are dispersed. Subsequently, phosphate groups were incorporated, taking advantage of the electrostatic interactions. These reactive polyphosphate groups will act as connectors between the protonated amide groups and/or the deacetylated amido groups (chitin transformed into chitosan), e.g., in the cell wall. Additionally, this functionality may involve polysaccharides that are also part of the fungal cell wall, which may prevent aggressive deacetylation steps for the mycelium.

In general, any appropriate nanoparticle may be used, not limited to $SiO_2$ nanoparticles. For example, ceramic materials, such as $TiO_2$, $ZnO$, $SnO_2$, $Al_2O_3$, $Fe_2O_3$, $Fe_3O_4$ either porous or non-porous and, nano-composites derived from these, may be used and may beneficially provide thermal resistance, photo-resistance, magnetism, and other properties. Polymeric particles could be used as well; some examples include (but are not limited to): zein, alginate, chitosan, latex, poly(lactide) (PLA), poly(lactide-co-glycolide) (PLGA) copolymers, poly (ε-caprolactone) (PCL), etc. These nanoparticles may be preferred, for instance, for the encapsulation of some aromatic compounds or thermoregulators. Likewise, metallic nanoparticles such as Au, Ag, Cu, Pt may be used, and may convey antimicrobial and self-cleaning and electrical properties. Carbon-based nanoparticles such as carbon nanofibers, single or multi-walled carbon nanotubes, graphene, and carbon spheres may provide electrical conductivity. Any combination among these different materials may achieve multifunctional mycotextiles.

In general, the nanoparticles may be easily functionalized to ensure and assist in their fixation on the material. In general, neither the nanoparticles nor the resulting fungal-derived textile is environmentally toxic or harmful to human health. Thus, the nanoparticles described herein may modulate one or more additional properties of the fungal-derived textile, such as thermal resistance, photo-resistance, magnetism, encapsulation, thermoregulation, conductivity, self-cleaning, superhydrophobicity, omniphobicity, pollutants capture, luminescence, UV-barrier.

Although the crosslinking particles described herein are referred to herein as nanoparticles and may preferably have a diameter of between about 60 and 600 nm, in some examples, this component may more correctly and generically be referred to in any of the examples described herein as crosslinking particles.

As mentioned above, any range of sizes of nanoparticles may be used. For example, the nanoparticles may generally be less than 1 um in diameter (e.g., largest/longest diameter), making them invisible to the naked eye and sufficiently small to penetrate and incorporate into the materials described herein. For example, the nanoparticles may be between about 10 and 650 nm (e.g., between 60-600 nm, between 420-630 nm, between 150-400 nm, etc.). In some examples, the nanoparticles are about 200 nm in diameter. In some examples, the properties (e.g., optical properties) may be tuned with the size of the particle. For example, the nanoparticles used herein may have a mean diameter of between 60 and 600 nm. Particles below 60 may result in cell endocytosis, and above 600 nm may not provide stable suspensions.

In some cases, the nanoparticles are spherical. However, the shape is not relevant for the property described herein. For instance, carbon nanotubes or nanofibers can also be used and may provide mechanical reinforcement. Amorphous silica products, such as Aerosil®, precipitated silica, or silica gel, could be used as reinforcements. Similarly, porous (e.g., meso, micro, or macroporous) nanoparticles (including but not limited to $SiO_2$ particles) may be used.

In all of these examples, the nanoparticles may be functionalized; functionalization is critical because it provides relevant properties that may be absent in the original material and may guarantee the fixation of the nanoparticles within the material. In the particular case of phosphate moieties, functionalizing agents may also include 3-(Trihydroxysilyl)propyl methylphosphonate, sodium polyphosphate, and phosphorous acid. For example, the number of phosphate groups incorporated on the $SiO_2$ surface may be optimized for each case. Silica is one of the most studied and one of the most industrialized ceramic supports. Several agents are known whose adsorption on the silica surface has been confirmed and will allow the development of a wide variety of different configurations. Some examples include: polyamines (e.g., Polyethylenimine) to capture cations, $H_2S$, $CO_2$, or acid vapors. Epoxy silanes (e.g., (3-Glycidyloxypropyl)trimethoxysilane) may be used as coupling agents to improve the bond strength of some organic resins with the mycelium. Alkyl silanes (e.g., Chloro(dimethyl)octylsilane) for superhydrophobicity. Methacrylate silanes (e.g., 3-methacryloxypropyltrimethoxysilane) may increase color adhesion. Other examples of functionalizing agents are: 3-(triethoxysilyl)propyl isocyanate, vinyltrimethoxysilane, hexadecyltrimethoxysilane, bis(3-triethoxysilylpropyl)tetrasulfide, etc.

Nanoparticles may be applied to the material (e.g., the putative fungal-derived textile) by soaking or spraying. For example, soaking the material in a colloidal suspension of the nanoparticles and/or by spraying (atomization). The concentration range evaluated was between about 0.1 g/L and 1 g/L, being the preferred concentration 1 g/L. Spraying (atomization) of functionalized nanoparticles a 10-times increase regarding the soaking approach should be applied.

In general, the use of nanoparticles in the methods and compositions (e.g., fungal-derived textiles) described herein takes advantage of crosslinking of the hyphae of the mycelium mat layer(s) in the textile. As described above, the nanoparticles are functionalized, e.g., on a surface of the nanoparticle, so that they bind to chitin within the hyphae, effectively crosslinking the hyphae. Therefore, the nanoparticles may act as a crosslinking intermediary, crosslinking to multiple hyphae. This process may be considered a green (e.g., environmentally friendly) nanocrosslinking scheme.

Nanoparticle Example

For example, the nanoparticles described herein may be $SiO_2$ nanospheres that may be formed by the Stöber-Fink-Bohn method. This exemplary method may consist of the controlled hydrolysis of an organic silicon compound in an alkaline medium. During a second stage, the condensation of the monomeric units causes the growth of the $SiO_2$ polymer network (Si—O—Si) that self-assembles in the geometric shape that provides the highest area-volume ratio (spheres). The components required for this synthesis are a few: tetraethyl orthosilicate (TEOS), ammonium hydroxide, ethanol, and water. The synthesis is usually completed after 120 min followed by the corresponding washes to neutralize the medium's pH and drying at 120° C. By varying the molar ratio between the components, the final diameter of the particles can be easily changed. To obtain 10 g of particles, a procedure such as the outlined below may be used: in a 1 L Erlenmeyer flask, a mixture of 355 mL of absolute ethanol, 25 mL of deionized water, and 90 mL of technical grade ammonium hydroxide (28-30%) may be homogenized under vigorous stirring (approx. 500 rpm) and at room temperature. Subsequently, 30 mL of TEOS may be added drop by drop. The solution may change from colorless to cloudy and then milky white over 30 minutes. It may be left under constant stirring until the completion of 120 min of reaction. 10 mL of concentrated HCl may be added very carefully to stop the reaction. After a few minutes, the flask contents may be transferred to 50 mL Falcon tubes and centrifuged at 6000 rpm for 10 min. The clear supernatant may then be removed and replaced with a 0.5 M HCl solution. The mixture may be vortexed to resuspend the particles and re-centrifuged. The clear supernatant liquid may then be removed, replaced with deionized water, and re-suspended using a vortex and centrifugation. This step may be repeated until verifying neutral pH in the remaining liquid. Finally, the white solid obtained may be placed in an oven under an air atmosphere at 120° C. for 2 h. The obtained particles may be seeded in an aluminum sample holder through carbon tape and taken to a scanning electron microscope for morphological analysis. As shown in FIG. 22A, spherical particles are obtained with the distribution of diameters represented in the graph of FIG. 22B. The frequency of particles is shown as a function of diameter. Measurement deviation is 8%, indicating slight size variation. Energy-dispersive X-ray microanalysis told the expected composition for $SiO_2$.

Nanoparticles may be functionalized in any appropriate manner. The functionalization of the particles may refer to the adsorption of groups of interest for the interaction with a specific chemical functionality existing in the fungal cell wall. In some examples, an amino functionality may be incorporated as a "binder" for either citrate and/or phosphate groups. These functionalities were evaluated for more interactions between the hyphae to promote crosslinking and were found to strengthen the mycelium mechanically. Once an amino functionality is covalently bound to the nanoparticle's surface, the interaction with the polycarboxylic or polyphosphate groups will occur electrostatically, controlling the pH of the medium where the particles are dispersed. This approach serves as a proof of concept regarding the feasibility of using $SiO_2$ spheres as a vehicle for different chemical groups of interest. In one example, a functionalization scheme may incorporate APTES followed by incorporating phosphate groups. This is illustrated schematically in FIG. 23.

In FIG. 23, amino groups were incorporated into the nanoparticles by a grafting procedure. As an example, each 0.5 g of $SiO_2$ spheres were dispersed in 50 mL of dry toluene, then 5 mL of (3-aminopropyl) triethoxysilane (APTES) was added, and the mixture was heated under reflux at 80° C. for 12 h. The suspension was filtered, washed twice with acetone, and the solid was dried in an oven under airflow. FIG. 24A shows an example of the ATR/FTIR spectra for $SiO_2$ and $SiO_2$—$NH_2$. The functionalized particles show the vibrational modes corresponding to the stretching vibrations of the methylene group $-CH_2$ (2930, 2860 cm$^{-1}$), confirming the presence of propyl chains corresponding to APTES molecules. The band for NH bending at 1560 cm$^{-1}$ also ensures the incorporation of the amino groups in the sample.

In another example, phosphate groups may be incorporated into the nanoparticles. For example, $SiO_2$-$NH_2$ particles were suspended in 50 mL of water with the help of an ultrasonic bath, and then 0.5 mL of polyphosphoric acid were added and left stirring at 800 rpm for 6 h at room temperature. The solid was separated by centrifugation at 8,000 rpm for 10 min and washed three times with distilled water. Raman spectrum of FIG. 24B shows the ($PO_4^{3-}$) phosphates characteristic vibrations overlapped with the broad signal around 550 cm$^{-1}$ corresponding to the Si—O—Si bond of the support simulated as a dotted line. The main bands are assigned to: symmetric stretching mode (v1) at 960 cm$^{-1}$; antisymmetric (v3) at 1070 cm$^{-1}$, bending mode v2 and v4 around 550 cm$^{-1}$ and 610 cm$^{-1}$, respectively; symmetric and antisymmetric deformation modes between 400 and 500 cm$^{-1}$; stretching band (A1) of the P—OH bond near 800 cm$^{-1}$.

The functionalized nanoparticles may be added to the fungal-derived textile material following the fermentation, as mentioned above. Although the discussion above described the impregnating with the nanoparticles after the internal wetting step, in some examples, the nanoparticles may be added/impregnated into the material before internal wetting or concurrent with internal wetting.

In one example, a prototype fungal-derived textile may be formed as described above using fungal strain 0006 (see above) for pre-fermentation and fermentation stages, and an activated scaffold/layer of carbon fiber may be used during the BIOrganic foam procedure. Following fermentation, the material may be internally wetted, as described, and nanoparticles (e.g., $SiO_2$ particles) may be added. This example demonstrates the interaction between the proposed functional groups and the mycelium. After immersion for more than 15 min and less than 24 h, in an acidic suspension of the functionalized nanoparticles (1 g/L), the prototype was allowed to dry in the air to 20% moisture content and later subjected to a pressing process at 70° C. for 60 s on both sides of the textile, while applying sufficient pressure to allow the heat to diffuse inside the mat. The soaking with the acidic suspension of nanoparticles was sufficient for incorporating the nanoparticles and the cross-linking between the hyphae. This was confirmed by scanning electron microscopy. At the same time, the interaction between the phosphates and the acetamide group was confirmed by FTIR spectroscopy. Changes in the thermal behavior of the material were analyzed by measuring the respective thermograms under $N_2$ flow in a range from room temperature to 1000° C. These analyzes were performed in a TA Instruments SDT Q600 equipment, using 90 μL alumina crucibles, at a heating rate of 10° C./min, with a UHP nitrogen gas flow of 100 mL/min.

Figure 25A:
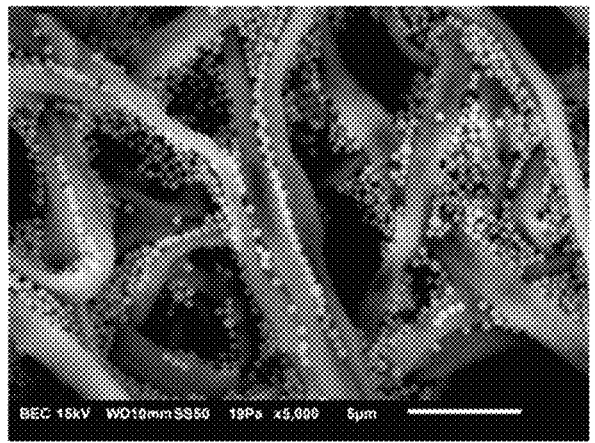
FIG. 25A is a scanning electron microscopy image of a section through a sample of fungal-derived textile (using fungal strain 0006) formed as described herein, in which nanoparticles have been impregnated, showing the nanoparticles' interaction with the hyphae.
Figure 25B:
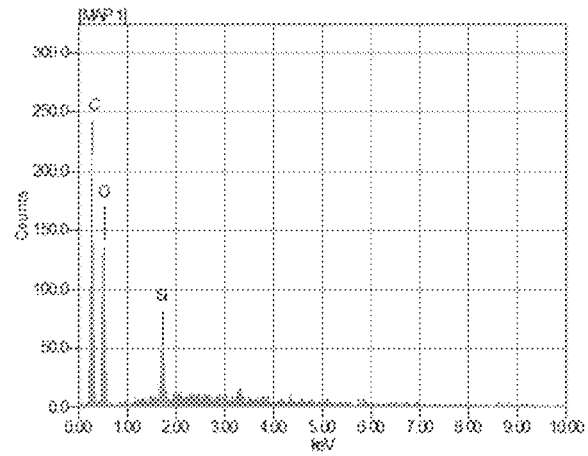
FIG. 25B shows an example of an EDS spectrum showing the presence of silicon in the sample.
Figure 25C:
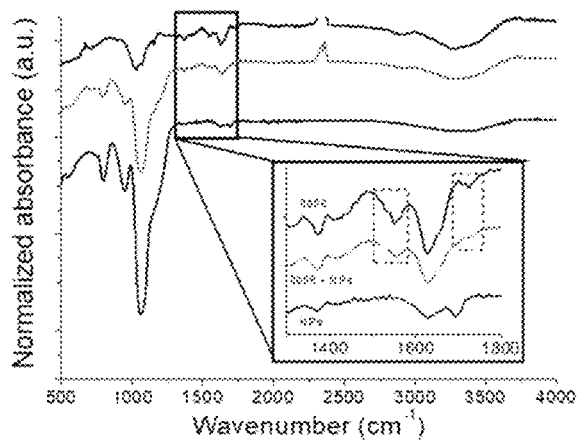
FIG. 25C shows an example of an ATR/FTIR spectra for the same sample material, showing the signals for this 0006 fungal strain that can be compared before and after incorporating the functionalized nanoparticles with phosphate groups.

These results are shown in FIGS. 25A-25D. In FIG. 25A, the scanning electron microscopy image confirms the presence of the particles, immediately apparent as electron-dense spheres or dots located between the walls of the hyphae, achieving the desired effect of bringing the hyphae closer together (e.g., by crosslinking). Energy-dispersive X-ray spectroscopy (EDS) analysis shows the signals of the main elements present in the sample, in this case, carbon, oxygen, and silicon. Under the conditions described before, the chemical analysis at different points of several samples indicates a concentration by weight of $SiO_2$ of (3.3±0.9) %, as shown in FIG. 25B. Analyzing the position and intensity of the bands relative to acetamide groups in the infrared spectra (the stretching vibrations of the NH bond around 1500 cm$^{-1}$ and the C=O bond around 1700 cm$^{-1}$), it was possible to determine that these moieties are involved in the interaction of the cell wall with the nanoparticles. This is illustrated in FIG. 25C. This interaction is possible through electrostatic forces between the protonated amide and the negatively charged polyphosphate groups on the nanoparticle's surface, mediated by the acidic medium.

Figure 25D:
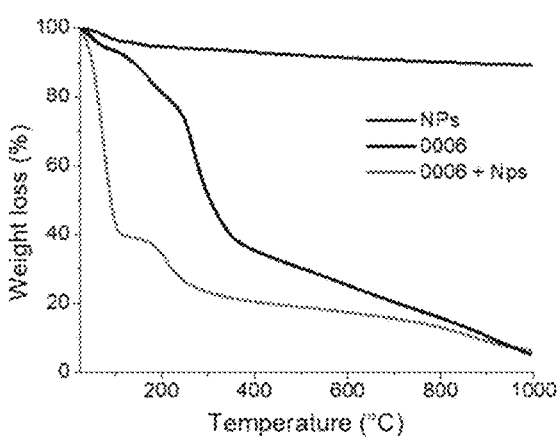
FIG. 25D is a graph of the profiles of the thermogravimetric analysis showing the variation in the behavior of the 0006 fungal strain under a thermal treatment before and after the incorporation of the nanoparticles.

FIG. 25D shows an exemplary thermogravimetric profile for the fungal strain (e.g., wild fungal strain 0006), showing changes in its thermal behavior after incorporating the nanoparticles. The total weight change in the nanoparticles after heating up to 1000° C. is only 11%. In the material without nanoparticles, a first mass loss of 5.3% occurs in the range from room temperature to 200° C., attributed to the evaporation of free and chemically bound water. Above 200° C., silica undergoes dehydroxylation of the surface silanol (Si—OH) groups, causing the rest of the loss. On the other hand, mycelium alone presents a significant loss of mass in the studied range due to its organic nature. The first change occurs from room temperature to 250° C., also associated with the loss of water molecules, representing 26% in weight. After, a mass loss of 36% occurs between 200-375° C., possibly due to the breakdown of organic constituents (e.g., amino acids, polysaccharides, chitin, etc.). Finally, a third mass loss occurs between 375-1000° C., due to further degradation of the primary residual carbon, which produces methane ($CH_4$) and the consequent formation of a carbonaceous residue (biochar). When the nanoparticles are incorporated, the thermal profile changes completely. In this case, the most significant decrease in mass is associated with water evaporation and occurs between room temperature and 110° C., representing 60% of the loss. Then, between 110-250° C., a second water loss occurs, possibly due to more strongly associated water molecules, representing 14% of the mass loss. Subsequently, between 250-1000° C., the material only experiences a mass loss of 19%, which is lower than the observed in the mycelium alone. The onset temperature for this event is lower than that observed in the mycelium alone, suggesting that the decomposition mechanism is different. As expected, incorporating these more refractory particles confers thermal stability to the material.

Figure 26A:
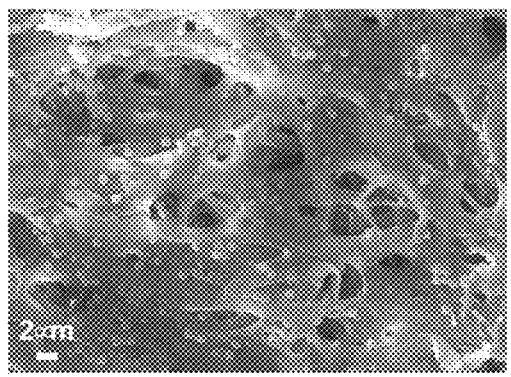
FIG. 26A is a scanning electron microscopy image of a section through a sample of fungal-derived textile (using fungal strain SB-0046, "0046") formed as described herein, in which nanoparticles have been impregnated, showing the nanoparticles' interaction with the hyphae.
Figure 26B:
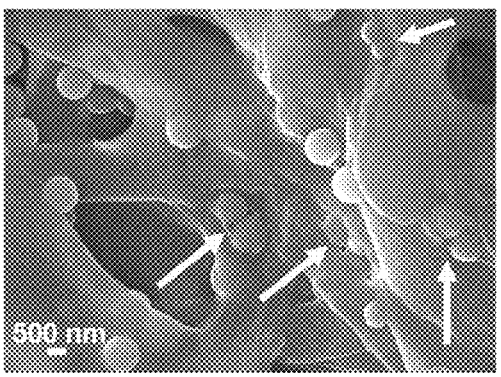
FIG. 26B shows a higher magnification of a region highlighting the location of the $SiO_2$ nanoparticles within two hyphae.

When mixed with another fungal strain such as 0046, the nanoparticles described in the previous example are also incorporated to the hyphae as observed in FIG. 26 A. As 0046 strain shows hyphae with a slightly higher mean diameter than the 0006 strain, the effect of the nanoparticles may be less evident at the selected size. However as highlighted in the enlarged microscope image in FIG. 26 B, the nanoparticles locate between two hyphae mediating in the approach between them.

Figure 27A:
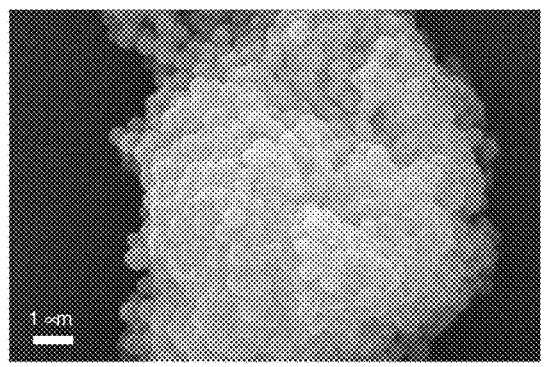
FIG. 27A is a scanning electron micrograph of $SiO_2$ nanoparticles using zein as an organic functionalizing agent synthesized as described herein.
Figure 27B:
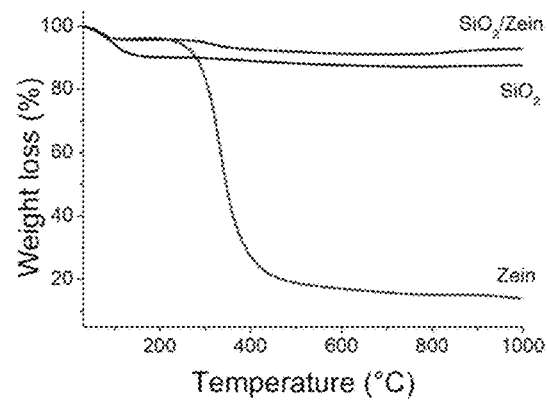
FIG. 27B is a graph of the thermogravimetric analysis profiles showing the functionalization of the $SiO_2$ nanoparticles with zein.
Figure 27C:
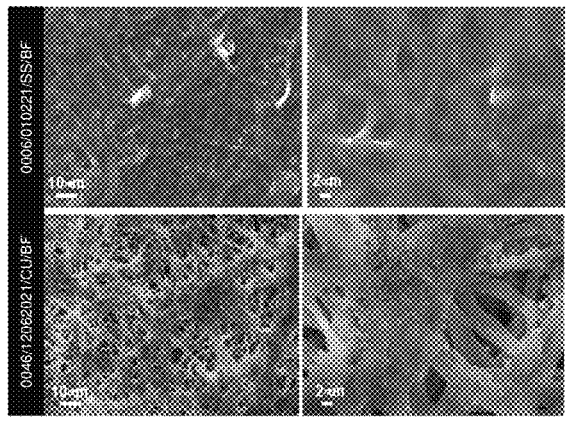
FIG. 27C is a scanning electron microscopy image of a section through a sample of fungal-derived textile (using fungal strains 0006 and 0046) showing a plurality of zein-functionalized $SiO_2$ nanoparticles.
Figure 27D:
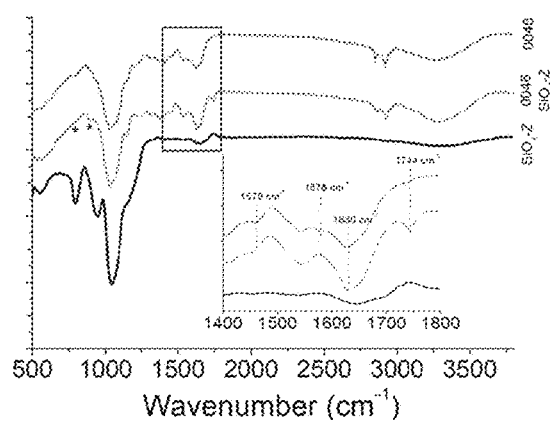
FIG. 27D shows an example of an ATR/FTIR spectra for the same sample material, showing the signals for 0046 fungal strain can be compared before and after incorporating the zein-functionalized $SiO_2$ nanoparticles.

An organic functionalizing agent such as zein (a prolamin obtained from milled corn) may be adsorbed at the silica surface to incorporate carboxylic and amino moieties from the protein residues. The amino acid profile of zein is primarily made of hydrophobic types, including leucine (19%), proline (10%) and alanine (12%). But it also contains polar acidic amino acids such as glutamic acid (20%). This approach requires from 0.1 to 1 wt. % of $SiO_2$ spheres dispersed in ethanolic solutions of zein with concentrations ranging from 0.015 to 1.5 wt. % at pH values ranging from 4 to 8 in a period from 5 in to 24 hours. A synthesis mixing zein and SiO$_2$ concentrations of 0.15 and 0.1 wt. % respectively, at neutral pH value under continuous stirring at room temperature for 12 hours yields the particles shown in FIG. 27A. The weight loss under nitrogen atmosphere around 350° C. observed in the thermogravimetric analysis of FIG. 27B indicates that the surface zein loading was around 2 wt. %, regarding the mass of the SiO$_2$. The interaction of these particles with prototypes from 0006 and 0046 strains shows a higher degree of aggregation between the particles which affects its distribution between the hyphae as shown in the SEM images of FIG. 27C. The FTIR spectra shown in FIG. 27D comparing the 0046 strain before and after the interaction with the nanoparticles functionalized with zein reveals two small signals at 760 and 900 cm$^{-1}$ (asterisks) related to the symmetric stretching of the Si—O bond. The disappearance of the peaks around 1480 and 1580 cm$^{-1}$ suggests that the amide moieties are involved in the interaction. Moreover, the apparition of the peak around 1740 cm$^{-1}$ suggests the incorporation of carboxylic groups, possibly from the zein glutamic acid.

Figure 28A:
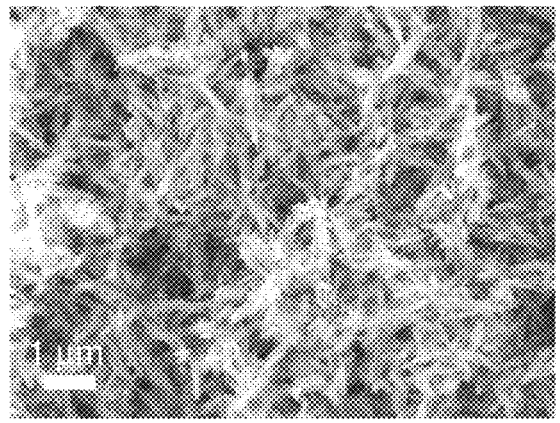
FIG. 28A is a scanning electron micrograph of zein-functionalized $Fe_2O_3$ nanorods.
Figure 28B:
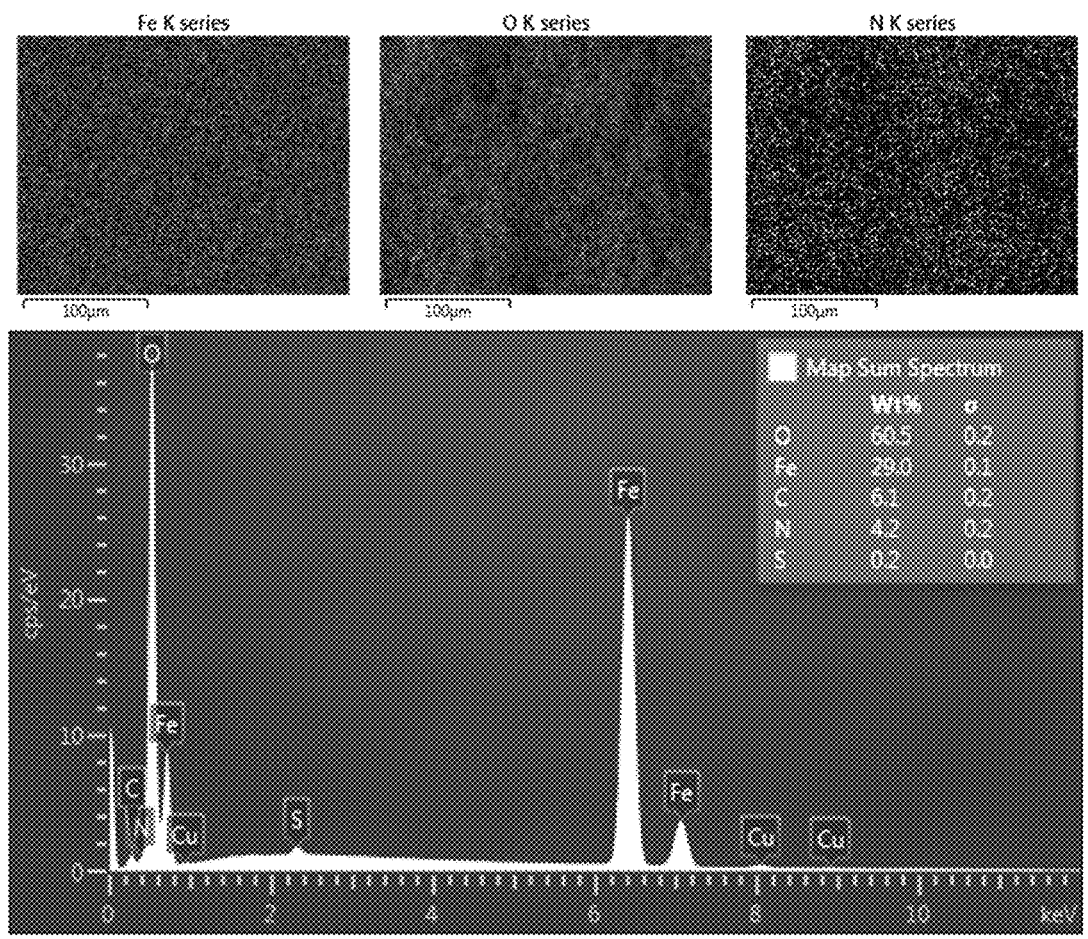
FIG. 28B is an EDS mapping of zein-functionalized $Fe_2O_3$ nanorods showing the distributions of the elements C, O, and N.
Figure 28C:
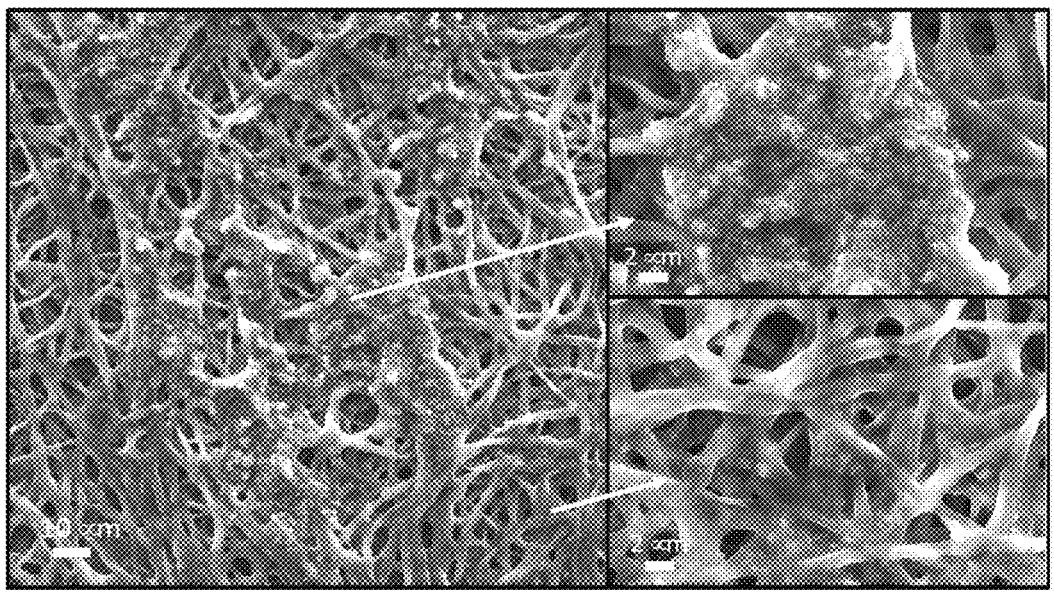
FIG. 28C is a scanning electron microscopy image of a section through a sample of fungal-derived textile using the fungal strains 0006 impregnated with the zein-functionalized $Fe_2O_3$ nanorods, showing different magnifications of the same region.
Figure 28D:
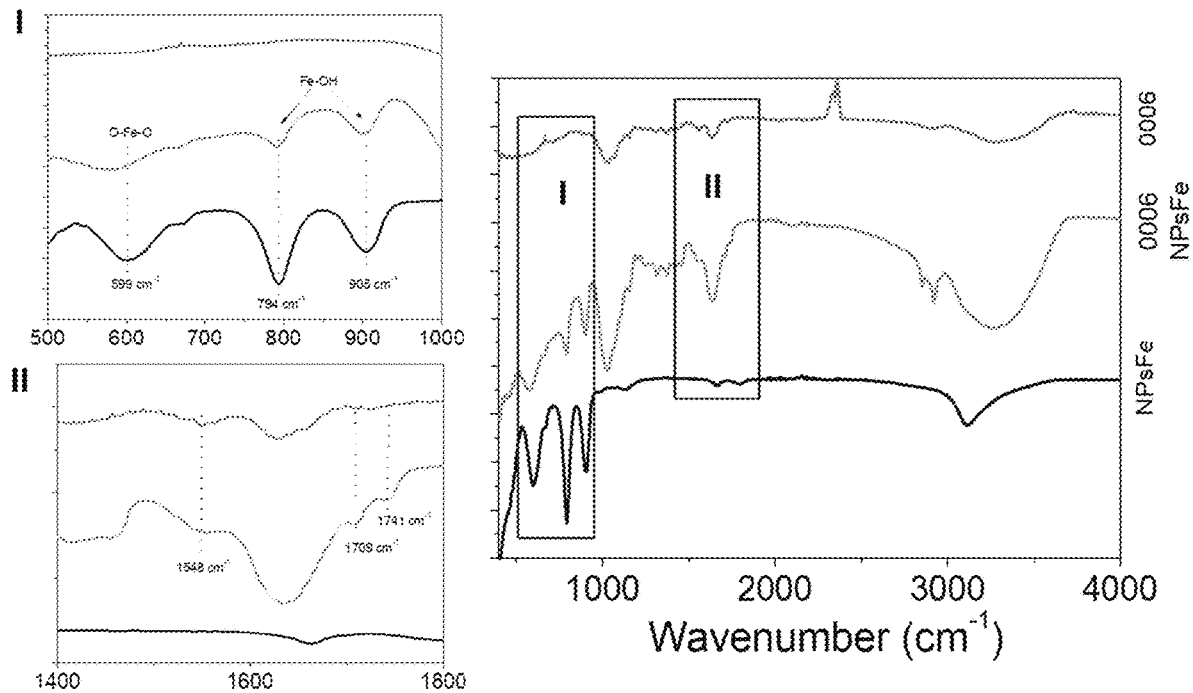
FIG. 28D is an ATR/FTIR spectra for the sample material showing the signals for 0006 fungal strain compared before and after incorporating the zein-functionalized $Fe_2O_3$ nanorods.

In another example, a different morphology of an inorganic material was tested. Iron oxide nanorods with approximate dimensions of 200×500 nm (wide×large) organically functionalized with zein as described for SiO$_2$ spheres are observed in FIG. 28A. This functionalization strategy does not change the morphology of the nanorods achieving homogenous nitrogen incorporations of around 4.2 wt. % according to the EDS analysis presented in FIG. 28B. The functionalized nanorods mixed with a fungal mycotextile obtained with the 0006 strain shows two distinctive regions highlighted at the right side of the FIG. 28C, in one region the particles appear agglomerated in small groups, while in the other regions they intertwine with fungal mycelium. The mean Fe$_2$O$_3$ content in the sample is 0.86±0.1 wt. % using this approach. FTIR spectra of the mycelium with and without particles as analyzed in frequency regions I and II reveal two major changes: in region I, the shift to lower frequencies of the bands at 599 905 cm$^{-1}$ related to Fe—O and Fe—OH stretching vibrations in Fe$_2$O$_3$ indicates a change in the chemical environment of the iron. In region II, the apparition of the peak around 1710 and 1740 cm$^{-1}$ irelated to carbonyl groups in carboxyl moieties.

Figure 29A:
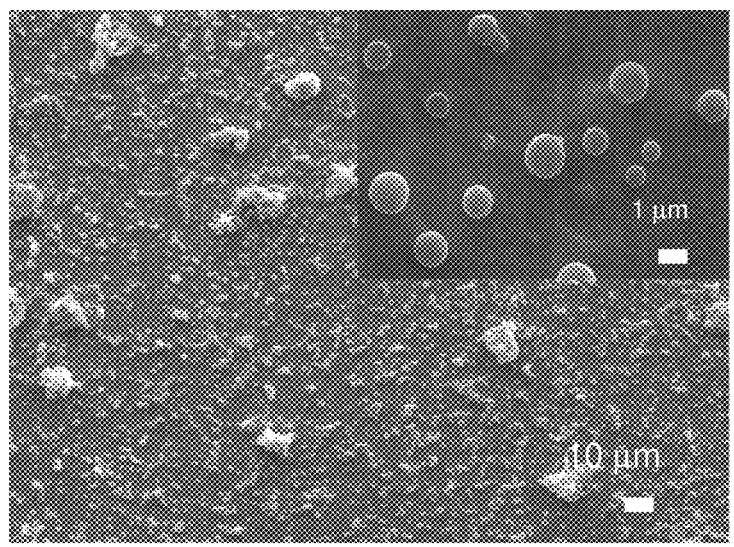
FIG. 29A shows a scanning electron micrograph of zein spherical nanoparticles synthesized as described herein, the inset reveals a higher magnification of the sample.
Figure 29B:
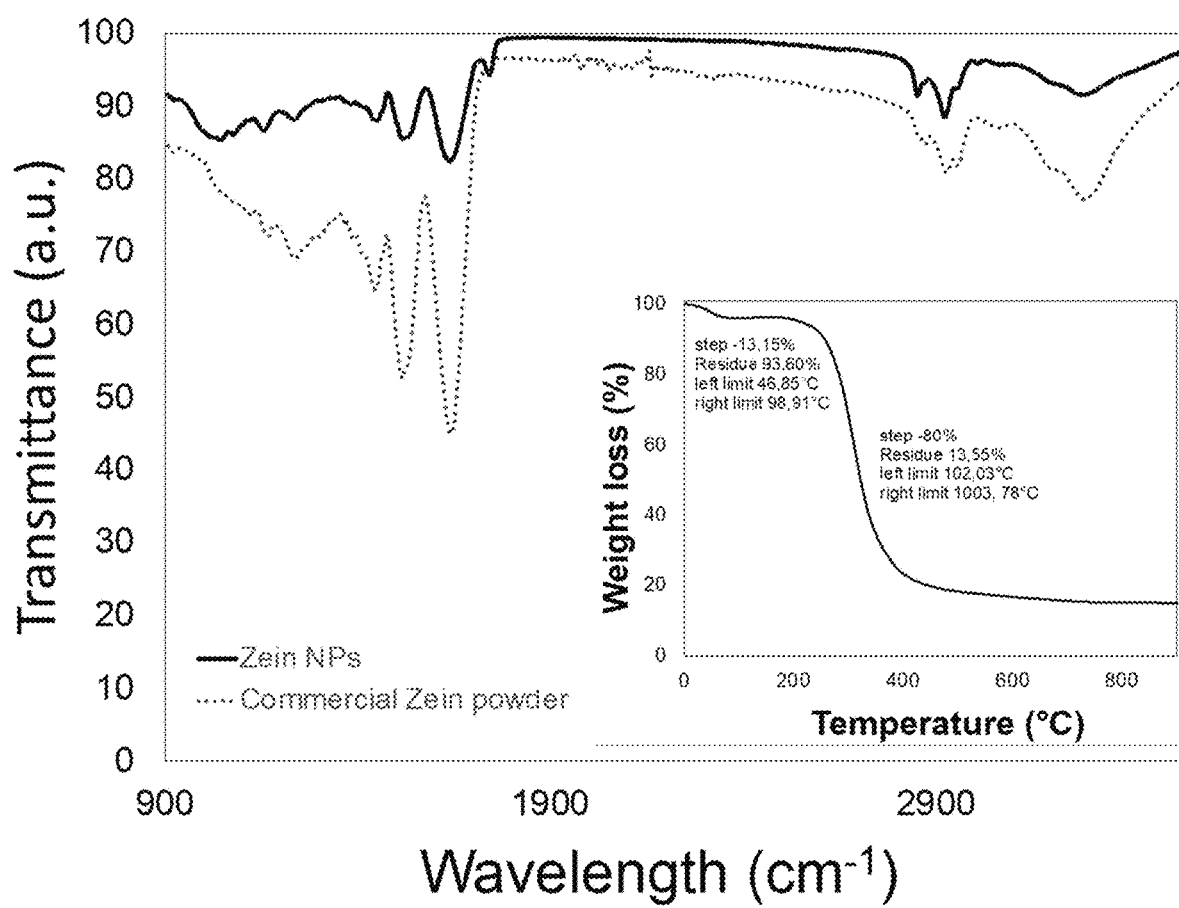
FIG. 29B shows an ATR/FTIR spectra of as-synthesized zein nanoparticles compared to commercial zein, the TGA profile in the inset corresponds to the zein nanoparticles.

In another example, zein spherical nanoparticles synthesized from an antisolvent method worked as organic cross-linkers. For this method, 100 g of milled corn was mixed with ethanol solution 70 v/v % at 70° C. for 1 hour under continuous agitation. The resulting yellow solution is poured in distilled water in a volume ratio of 1:3, the obtained solid is recovered by centrifugation at 12000 rpm during 10 min. SEM image in FIG. 29A shows a distribution of the material with particles size between 200 nm and 1000 nm, while FTIR spectrum at FIG. 29B reveal that the vibration bands of the nanoparticles obtained using such antisolvent method matches with the bands of a commercial zein (Merck, product code: Z3625). TGA analysis show a weight loss of 93.15% centered in two temperature ranges, the first of 13.15% around 60° C. related to water loss, and the second one around 350° C. with a weight loss of 80% related to the decomposition of the organic substance that perfectly matches the profile obtained for pure zein as observed in a previous example. The remaining 6.86% after 1000° C. corresponds to ashes content in the sample.

Figure 29C:
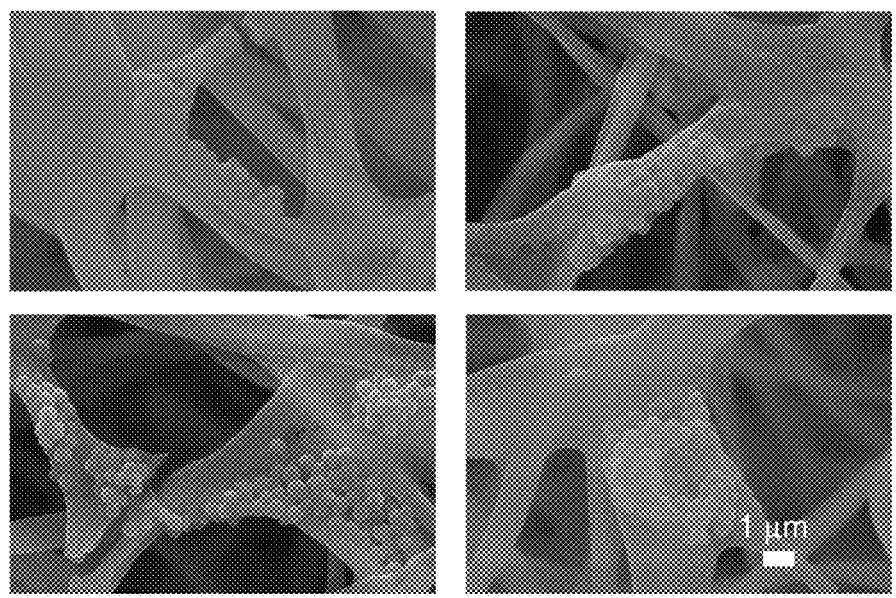
FIG. 29C shows a scanning electron micrograph of several sections through a sample of fungal-derived textile using the fungal strains 0006 impregnated with zein spherical nanoparticles.

An SEM image of the organic nanoparticles interacting with 0006 mycelia in a typical prototype is shown in FIG. 29C, at four different locations of the sample, to confirm the presence of the zein nanoparticles along the hyphae structure. It is observed that zein nanoparticles tend to agglomerate but they show great interaction with the surface. These particles are obtained with an easy strategy able to provide nanoscale carrier systems.

The nanoparticles described herein may be used as an environmentally-friendly (e.g., "green") alternative to traditional tanning applications and may also confer additional desired characteristics to the materials described herein, referred to as smart mycotextiles. For example, forming the nanoparticles by growing porous SiO$_2$ onto nano-magnetite would provide cross-linking nanoparticles that have a core-shell structure that may be responsive to magnetic stimuli. Another possible application is the capture of greenhouse gases, such as CO$_2$, by changing the functionalizing agent for branched amides. Decorating the carrier with photoactive nanoparticles such as TiO$_2$ or ZnO may allow self-cleaning textiles. Incorporating conductive fibers, such as graphene, carbon nanotubes, or nanofibers, could provide a conductive fibrous composite able to transmit electric signals useful to collect environmental or health data.

Pressing

As mentioned above, the material may be pressed (e.g., ironed) and/or stamped when forming. Pressing may be used to generate a more uniform thickness and/or density when fabricating the material. For example, one of the quality parameters of traditional leather is a homogeneous thickness. Pressing may be used with the materials described herein in order to provide homogeneity in the thickness of the materials. Pressing can occur through different mechanisms, either by mechanical pressing, e.g., using a parallel plate press, vacuum supported, or rollers. Rollers are commonly used in the textile industry to handle considerable lengths of material. Pressing may also be used to form a pattern or patterns into the material; for example, pressing can add a pattern that simulates grainy textures similar to animal leather.

The amount of force used for pressing and the temperature and manner of pressing may be within a predetermined range to avoid damaging the material. The pressure applied during the pressing process may be selected so that it does not damage the integrity of the mycelial layer(s). For example, the pressure may be between 20 and 60 Ton (between 20-55 Ton, between 20-50 Ton, between 20-45 Ton, between 20-40 Ton, between 20-35 Ton, between 20-30 Ton, less than 60 Ton, less than 55 Ton, less than 50 Ton, less than 45 Ton, less than 40 Ton, less than 35 Ton, less than 30 Ton, etc.). In some examples, the pressure applied is between 25 and 40 Ton when the support layer/scaffold is polyester or cotton. Pressing plates may include an embossing pattern to impart surface texture and appearance, such as but not limited to a grain pattern, in the mycotextile (leather) surface.

Chemical Activation with Mordant

Any of the materials described herein may be dyed or colored, and in some examples, a mordant may be used. In general, the fungal-derived textiles described herein may be dyed, and homogeneous and lasting impregnation of color is possible, incorporating specific molecules that help fix the dye in the fiber; these molecules are known as mordants. Mordants have been traditionally used as part of the color/dyeing process for modifying or fixing a color. They may include polymeric substances such as tannic acid and polyamide or ionic substances such as potassium alum, chrome alum, sodium chloride, and certain salts of aluminum, chromium, copper, iron, iodine, potassium, sodium, tungsten, and tin. Many colorants are applied in conjunction with substances that act as mordants, such as alum, potassium bichromate, tannin, and copper acetate.

Potassium alum, which is a double-hydrated aluminum and potassium salt $(KAl(SO_4)_2 \cdot 12H_2O)$ may be dissolved in the dye bath itself or it could be incorporated into the fabric beforehand to be impregnated into the fibers before coloring. In some fungal-derived textiles described herein, an aqueous solution with a concentration of between 1 and 10% w/w may be used. For example, an aqueous mordant solution may be sprayed on the fabric before staining/dyeing.

In any of the fungal-derived textiles described herein, polyamide resin may be combined with the dye in a proportion ranging 1 to 10% in an alcoholic solution. Polyamides act as a polymeric organic mordant or dye absorbers compatible with various types of polymeric fiber-forming materials. For instance, linear polyamides of relatively low melting point from hydroxy aromatic dicarboxylic acids and diamines are useful as mordants or dye absorbers in rendering fibers composed of cellulose acetate, cellulose triacetate, acrylonitrile polymers, polyamides, polyesters and polyhydrocarbon polymers such as polyethylene and polypropylene. Polyamides resins are linear condensation polymers with a high degree of crystallinity with repeating amide links in their molecular chain. Polyamides are engineering polymers characterized by exceptional hardness, good impact strength, and high abrasion resistance. Their excellent mechanical characteristics may be the result of the amide links leading to internal hydrogen bonds between the different polymer chains. Biobased polyamides that are commercially available are either based on sebacic acid or undecenoic acid, both of which can be derived from castor oil.

Dyeing

The fungal-derived textiles described herein may be used without significant coloring (dyeing), particularly if the color of the fungal strain used is desired. However, any of these materials described herein may be colored or dyed. Water-based dyes, or in a gel form, have excellent coverage and can be spread directly on the fungal-derived textile material. In addition, such dyes can be applied by soaking or spraying, including spraying separately or together with the mordant. The dyes that may be used may have one or more of the following components: water and/or, propylene glycol and/or, glycerin and/or, a hydrophilic biopolymer (e.g., starch), and artificial dyes (e.g., Red allura AC, red No 40, Azorubine, red No 3, Tartrazine, yellow No 5, Twilight yellow, yellow No 6-, Brilliant blue FCP, blue No 1, indigotin, blue No 2, etc., alone or in combinations among them). The post-fermentation processes described herein (including internal wetting, etc.), as well as the presence of biopolymers and plasticizers, means that the dyes or colorant (with or without mordant) may be used without dehydrating the material.

In some examples, the dyes may contain metal complex dyes for dyeing and finishing leather in a composition below 5 wt. % in alcohol solution using a convenient mordant according to the examples described above. In some examples, the application of these compositions could be performed either by immersion in a dye alcoholic bath for less than 180 s or by spraying under air pressure when polyamide resin is used as a mordant.

External Wetting/Humidity Barrier

Any of the materials described herein may also include an external wetting step and the resulting humidity barrier. For example, a humidity barrier may be applied to any of these materials by applying an external wetting composition to the outer surfaces (both surfaces or just one surface).

In general, the external wetting composition may include a biopolymer capable of forming biofilms near room temperature. For example, the external wetting composition may include a soluble polymer (e.g., chitosan, starch, gelatin, agar, polylactide, polyhydroxyalkanoates, zein, etc.) at proportions between 0.2-30%, preferable between 1 to 3%, a plasticizer (e.g., glycerol, polyglycols, polyalkylene oxides, or polyadipates) at proportions <1%, a wax (e.g., beeswax, carnauba wax, candelilla wax, etc.) at 50% or less (e.g., between about 1%-50%, 10%-50%, 15%-50%, 20%-50%, 25%-50%, 30%-50%, etc. and, an oil (e.g., coconut, silicon, linseed, soybean oil, etc.) in proportions less than 20% (e.g., between 0.1% to 20%, 1% to 20%, 10% to 20%, etc.) preferably, between 1 to 15, most preferably between 1 to 5%, compounded as a room-temperature paste. Optionally no plasticizer may be used, no wax may be used and/or no oil may be used.

Developing an efficient external moisture barrier may be helpful to prevent moisture loss that leads to material dehydration and fracture. External wetting compositions may include glycerol, sorbitol, or polylactic acid (a thermoplastic polyester). The moisture barrier should ideally form a thin layer on the surface that does not hide the appearance of the surface provided by the mycelium. The moisture barrier should act as a barrier both for the entry of water vapor and the exit of internal moisture and may prevent or reduce color loss. Although natural waxes have been suggested for both animal-derived textiles and fungal-derived textiles, compositions including natural waxes have been difficult to use for this type of application, partly because they are difficult to apply due to their solid nature. Ideally, an external wetting composition would comprise a mixture having the rheological properties appropriate to distribute the waxes homogeneously on the surface with little effort.

For example, any of these external wetting compositions may optimally include a biopolymer (e.g., polysaccharides or proteins) capable of forming biofilms near room temperature. Described herein are external wetting compositions comprising a plasticizing wax that has been specifically formulated and adapted from use with the fungal-derived textiles described herein. For example, a biopolymer may include chitosan, which is conveniently a by-product of the method for forming the textiles described herein. In one example, approximately 80 g of the external wetting composition (wax) may be formulated by: dissolving 1 g of medium molecular weight chitosan in 1 mL of glacial acetic acid and 50 mL of water. To ensure complete dissolution, the mixture may be left under stirring at 25° C. overnight. 0.2 g of glycerol may then be incorporated. 34 g of cosmetic grade beeswax may be melted at 80° C., and the chitosan solution may be brought to the same temperature as the wax. Under high agitation (10,000 rpm), the molten wax may be gradually incorporated into the composition. 3 g of coconut oil may be incorporated at 80° C. and the mixture left under stirring for 5 min. The material may form a white fluid paste, which at 70° C. completely melts into a transparent film. For its application, only the application area may be preheated, and a portion of wax may be well dispersed onto the material so that when it melts, it can be expanded over the entire surface. For example, on a 10×10 cm mat, approximately 2 g of the external wetting composition may adequately cover the surface. The external wetting composition (wax) may be spread onto the fungal-derived textile surfaces with the help of a roller press or an iron. FIG. 30A shows a view of a cross-section of a prototype fungal-derived textile, fabricated using the fungal strain 0006 and processed with each of the post-fermentation techniques described above. In FIG. 30B the image shows a section through the material imaged using a scanning electron microscope. The outermost layers of about 40 m correspond to the layer of external wetting composition (e.g., plasticizing wax) formulated as described above to protect the surface of the textile.

In another example, the external wetting composition may optimally include a protein such as zein or pea protein. A probable composition may include zein protein at 1 wt. % in a mixture of ethanol and glycerol (1:1). The zein mixture can be spread or sprayed on the surface. Another zein composition involves a pH adjustment up to 12 and a water-glycerol mixture (3:1). FIG. 31A shows the transversal cut of a material prepared as described herein, using the 0006 fungal strain, and applying the post-treatment scheme described herein, including internal wetting, crosslinking, pressing, activation with mordant, dyeing, and external wetting based on zein. FIG. 31B shows the homogeneity obtained on the surface of the material (top view of the same material).

In any of the materials described herein, the material's outer surface (e.g., including the external wetting/humidity layer) may include one or more texturing components (e.g., texturizing particles). The texturizing particles may be texturizing beads. For example, the outer surface may include polymeric expandable/swellable beads (e.g., "microbeads", such as EXPANCEL® beads), comprising ethylenically unsaturated monomers that may be incorporated into the humidity barrier or as an external topcoat to confer a new texture to the material. For example, microbeads may be distributed across the surface by suspending the microbeads in an acrylic emulsion. For example, polyethylene adipate/polymethylene methacrylate, P(EA/MMA). This could be applied as a last step of the post-processing scheme, e.g., after the external wetting/humidity barrier is applied. Alternatively, the texturing material (e.g., microbeads) may be incorporated and applied as part of the external wetting composition.

A texturizing material may include particles (texturing particles) having any shape (beads, spherical, oval, elongate/fibrous, etc.) and may be of any size, including a range of sizes (e.g., diameters between 1 μm and about 500 μm (e.g., between 10 μm and 900 μm, between 10 μm and 500 μm, between 20 μm and 400 μm, etc.). As mentioned, the texturing particles may be swellable/expandable.

Mechanical Properties

In general, the fungal-derived textile materials described herein include many beneficial characteristics that are apparent from the way they are manufactured. For example, the fungal-derived textiles described herein may include at least three layers, including the support layer/scaffold surrounded on either side by cross-linked mycelium strata, and one or both outer surfaces may be a humidity layer. The crosslinked mycelium strata may be interdigitated into the support layer/scaffold and typically are crosslinked by the inclusion of functionalized (crosslinking) nanoparticles.

Fungal-derived textiles described herein may have superior mechanical properties, particularly compared with other textiles incorporating fungal material. Fungal mycelium alone shows tensile strength values below 1 MPa. In contrast, this parameter varies between 8 and 20 MPa in cowhide leather. Synthetic leather can have values of 10-15 MPa. Other characteristics, such as elongation after the break, deacetylation strength, or abrasion resistance, are exceptionally good for cowhide. The materials described herein include features that may match or exceed these characteristic properties. Preliminary tests of the fungal-derived textiles described herein identified the mechanical characteristics, including tensile strength (TS) and elongation percentage before rupture (E %), according to the ASTM D2209 standard. The tests were carried out in a universal machine of the Shimadzu brand model AGX Plus, with a 1 kN load cell, speed of 254 mm/min, and pneumatic jaws with neoprene faces to avoid damage to the samples. Tear Strength (TeS) was also tested using the same equipment, applying ASTM D4704-13 standards. In both cases, the specimens of each sample were obtained utilizing a clamp or mold with the corresponding geometry requested by the standard. Abrasion resistance (AR) was examined according to the ASTM D3884 Taber abrasion resistance test. A TABER model 5155 abrasive was used for these measurements at a rotation speed of 120 rpm equipped with a wheel load of 500 g and following 1000 rotation cycles.

The results obtained are compiled in tables 6 to 11.

TABLE 6

Effect of the fungal strain on tensile strength and elongation of the mycotextile.

| Strain | Scaffold | Crosslinking | Tensile strength MPa | Elongation % |
|---|---|---|---|---|
| GL (control) | A1 | No (Freshly harvested) | 5.4 ± 1.3 | 170 ± 3 |
| | | Tannic acid | 11.1 ± 1.1 | 90 ± 8 |
| 0006 | | No (Freshly harvested) | 6.7 ± 0.3 | 243 ± 8 |
| | | Tannic acid | 7.5 ± 0.8 | 253 ± 8 |

TABLE 7

Effect of the activated scaffold on freshly harvested mycotextiles (no post-treatment)

| Scaffold | Tensile strength MPa | Elongation % | Tear Strength N*m | Flexibility cycles |
|---|---|---|---|---|
| None (Pure mycelium) | 0.06 ± 002 | 15 ± 7 | NM | <10 |
| A1 (65% polyester) | 6.7 ± 0.3 | 243 ± 8 | NM | NM |
| A2 (100% cotton) | 2.10 ± 0.01 | 29 ± 7 | NM | NM |
| A3 (50% polyester) | 4.1 ± 0.4 | 153 ± 5 | 2.8 | 50000* |

NM = not measured
*Detected tearing

TABLE 9

Effect of the $Fe_2O_3$ nanorods concentration to obtain a wild mycotextile using 006 fungal strain (without both nanoemulsion and finishing)

| Concentration (wt. %) | Tensile strength (TS) MPa | TS enhancement % | Elongation (E) % | E decreasing % |
|---|---|---|---|---|
| 0 | 4.1 ± 0.4 | 0 | 153 ± 5 | 0 |
| 0.05 | 6.0 ± 0.8 | 46 | 134 ± 5 | 12 |
| 0.125 | 7.2 ± 1.6 | 76 | 112 ± 44 | 27 |
| 0.25 | 8.1 ± 0.9 | 96 | 80 ± 3 | 48 |

TABLE 8

Effect of the nanoparticle type and functionalization on 0006 fungal strain prototypes crosslinking to obtain a wild mycotextile (no finishing)

| Type of nanoparticle | Functionalizing agent | Example | Tensile strength (TS) MPa | TS enhancement % | Elongation (E) % | E decreasing % |
|---|---|---|---|---|---|---|
| Prototype freshly harvested | | Control | 4.1 ± 0.4 | 0 | 153 ± 5 | 0 |
| Inorganic | Inorganic | $SiO_2$/P | 6.3 ± 0.8 | 56 | 121 ± 6 | 21 |
| | Organic | $SiO_2$/Z | 5.4 ± 2.1 | 32 | 142 ± 10 | 7 |
| | NA | $Fe_2O_3$ | 7.2 ± 1.6 | 76 | 112 ± 44 | 27 |
| | Organic | $Fe_2O_3$/Z | 4.8 ± 0.9 | 17 | 150 ± 12 | 2 |
| Organic | NA | Zein spheres | 4.9 ± 1.2 | 19 | 135 ± 4 | 12 |

NA = Not applies, P = polyphosphate, Z = zein, all examples use a concentration of 1 $gL^{-1}$ of the nanoparticle's suspension.

TABLE 10

Effect of the dyeing process in 0006 fungal strain prototypes obtained with the post-treatment scheme based on internal humectation with coconut oil emulsion, assisted-nano crosslinking using $SiO_2$/P nanoparticles and zein coating.

| Type of dyeing | Tensile strength (TS) MPa | Elongation (E) % | Tear Strength (TeS) N*m | Flexibility (F) cycles | Colorfastness (CF) (1-5) 50 cycles dry |
|---|---|---|---|---|---|
| No dyeing (Wild prototype) | 6.4 | 167 | 4.6 | >50000 | NA |
| Spray dyeing | 5.9 | 103 | 5.1 | >50000 | 2 |
| Dipping dyeing | 8.8 | 150 | 5.6 | >50000 | 4-5 |
| Dipping dyeing and embossing | 7.4 | 152 | 7.4 | >50000 | 4-5 |

NA = Not applies.

TABLE 11

Effect of the scaffold reinforcement to obtain a wild mycotextile using 0006 fungal strain with superb tensile strength values.

| Scaffold | Reinforcement | Tensile strength (TS) MPa | Elongation (E) % | Tear Strength (TeS) N*m | Flexibility (F) cycles |
|---|---|---|---|---|---|
| A1 | No | 6.7 ± 0.3 | 243 ± 8 | NM | >1000 |
| | GF | 5.2 ± 1.0 | 21 ± 2 | 39 | >1000 |
| | CF | 24 ± 2 | 41 ± 2 | 16 | >1000 |
| A3 | No | 6.4 | 167 | 4.6 | 50000 |
| | PAF | 5.9 | 146 | 7.3 | 50000* |
| | CI | 28 ± 5 | 19 ± 2 | NM | 50000* |

No = No reinforcement, NM = not measured, GF = glass fiber, CF = carbon fiber, PAF = polyaramid fiber, CI = 100% Cotton Interlining.
*Detected tearing in one of three replicates (33.33%).

As shown, values of some mechanical characteristics measured in different prototypes may vary depending on the scaffold/layer material (e.g., cotton, glass fiber, carbon fiber, etc.), as well as the fungal strain used (strain 0006 include properties described above such as the percentage of chitin and additional reactive sites), and the use of nanoparticles (NPs) as a crosslinking agent, and the fermentation strategy used. Table 6 shows an example material using the commercial strain *G. lucidum* (SB-0000, "GL"), which was formed in a manner that was otherwise equivalent to the wild fungal strain (e.g., strain 0006 having a chitin fraction of 45% or greater), without crosslinking had worse mechanical properties (TS=5.4 MPa) as compared with the fungal strain 0006 (TS=6.7 MPa). The TS value was lower than that of the prototype obtained with our 0006 strain because the wild fungal strain shows slightly larger diameter of the hyphae, higher chitin content and additional reactive carbonyl group providing, in sum, a greater number of crosslinking sites. In addition, wild fungal strains such as 0006 (e.g., having a chitin fraction ((1-6)-β-D-glucans plus chitin) of 45 to 80% and enriched for acetamide and/or amide groups) that were grown using the foam technique (e.g., the BIOrganic Foam). The treatment using tannic acid caused a significant effect on the commercial strain *G. lucidum* (SB-0000), reporting an increase of 106% in the TS and a decrease of 47% in E. When the conventional strategy (e.g., tannic acid) is used for 0006, TS increases from 6.7 MPa to 7.5 MPa, and E decreases by 3.8%.

The effect of the scaffold in freshly harvested prototypes (without post-treatment) is shown in Table 7. As compared to pure mycelium, the use of non-reinforced chemically activated scaffolds increases the TS but also the E %. The option named as A2 (raw 100% cotton fabric) showed the lowest TS and E %. However, those scaffolds composed of cotton and polyester (50% and 65%) showed higher TS and E %, both increasing proportionally with the polyester content.

The nanoparticle-assisted crosslinking was verified by varying the chemical nature of the nanoparticles and functionalizing agents (organic or inorganic), as well as the particle shape (nanospheres or nanorods). Table 8 compares the TS and E % for several prototypes from 0006 strain obtained by immersion in 0.1 wt. % suspensions of $SiO_2$ nanospheres, $Fe_2O_3$ nanorods, or zein nanospheres without other treatment. The immersion in the silica spheres suspension drastically increases the tensile strength up to 53% ($SiO_2$ loading of 3.3 wt. % in the final material). The immersion in iron oxide nanorods causes a TS enhancement of 73% despite the content in the final material being less than the obtained with silica spheres (0.86 wt. %). Thus, iron oxide nanorods may have a higher effect on the reinforcement. When both particles ($SiO_2$ and $Fe_2O_3$) are functionalized with zein, an organic functionalizing agent, the TS increases in 32% for $SiO_2$/Z and 17% for $Fe_2O_3$/Z, respectively, probably because of the poor dispersion observed in SEM images. Thus, higher dispersion of particles into the hyphae will promote a higher effect on tensile strength values. Zein nanospheres also caused a low enhancement in tensile strength (19%). The result showed that all nanoparticles cause a decrease in elongation. The highest diminution in the elongation percentage was obtained when using iron oxide nanorods.

The concentration of iron oxide nanorods in the suspension varied from 0.05 to 0.25 wt. %. Table 9 shows that TS enhances with the concentration of iron oxide nanorods while E % decreases with this. Higher content of iron oxide nanorods increases the density of the material as well as the hyphae's intertwining, hence the tensile strength is increased. These results account for the nanoparticles-assisted crosslinking.

The finishing strategy may also affect the mechanical properties. Table 10 summarizes tensile strength, elongation, tear strength, flexibility, and colorfastness of some examples using metal anilines and polyamide in the dyeing formula applied by spraying or dipping. Both strategies cause a slight increase in the TS and TeS but a slight decrease in E %. Dyeing by dipping increases TS in 16% and TeS in 22%. After the embossing TS increases in 37% and TeS in 61%. However, E % only decreased between 9 to 10%. When the dyeing formula is applied by spraying TeS increased 11% while the elongation and TS decreased by 38% and 8%, respectively. Without being bound by theory, it is possible that the mordant in these examples caused an extra reinforcement because of the chemical closeness with the polysaccharides that make up the cell wall of fungus. Colorfastness is better when dipping strategy is used for dyeing the materials. An optimal value of 5 both dry and wet could be improved with other coating strategies.

A1 scaffolds reinforced with inorganic fibers (e.g., glass, carbon, etc.), as observed in Table 11, resulted in prototypes with 5.2 and 24.0 MPa of TS. Glass fiber does not increase the tensile strength but drastically diminishes the E % to 21%, the TeS is the highest of the group (39 KN/m), and the AR exceeded 1000 abrasion cycles. The prototype obtained using a support layer/scaffold and carbon fiber as reinforcement, as described herein, has a tensile strength of 24.1 MPa, representing an increase of 458%, the elongation before breaking is 41%, the tear strength is 16 KN/m, and >1000 abrasion cycles. In other examples, A3 scaffolds reinforced with organic-based fibers such as polyaramid or cotton interlining show TS values of 5.8 and 27.6 MPa, respectively. Polyaramid fiber did not increase the TS but increased the TeS and decreased the E % in 59% and 13%. The incorporation of the cotton interlining into the prototype increased the TS in 331% and decreased the E % in 89%. Therefore, cotton interlining and carbon fiber may be particularly beneficial options that significantly enhance the mechanical properties of the mycotextile material. These values are similar to those used for animal and synthetic leather.

The use of the nanoparticles for crosslinking in combination with the fungal strains having a chitin fraction of 45 to 80% and enriched for acetamide and/or amide groups provided a highly durable material as compared with other strains or without the use of the nanoparticles, dramatically decreasing or eliminating the separation between the support layer/scaffold and the mycelium strata.

Thus, any of the fungal-derived textiles described herein may be reinforced with a material including (but not limited to) carbon fiber (CF) and/or cotton interlining, which may result in a tensile strength of >23 MPa with the mycelium (e.g., 24 MPa or more). These materials may be suitable for applications requiring higher mechanical properties, such as automotive upholstery, shoes, bags, etc. For other applications, such as the apparel industry, tensile strength values between 5 to 10 MPa are sufficient. At the same time, elongation (20-40%) and tear strength (>20 N) may be more relevant to ensure flexibility and resistance to tearing. Glass fiber reinforcement may also be used.

The support layer/scaffold material may have a fabric weight of between about 100 and 600 g/m$^2$, e.g., 100 to 200 g/m$^2$ for lighter textiles, between 200 and 400 g/m$^2$ for mid-weight textiles, and between about 400 to 600 g/m$^2$ for heavier textiles. In some cases, the support layer/scaffold may have a value of between about 130 to 150 g/m$^2$. The support layer/scaffold material (without mycelium) may have any appropriate thickness. For example, the support layer/scaffold may have a thickness of around 0.25 mm; multiple layers may be used (e.g., two layers in some prototypes have a thickness of 0.50 mm). An example using two layers is shown in FIGS. 19A-19B, obtained with *G. lucidum* SB-0000 (GL).

The fungal-derived textiles described herein (including support layer/scaffold, mycelium, and humidity barrier) may have a thickness from about 0.5 to about 2.5 mm. The mycelium layer may contribute between about 0.1 to 1 mm on each side. The thickness on the two sides may be different (the side containing aerial mycelium may be thicker). The final fungal-derived textile may have an optimal thickness between about 1-2 mm for different apparel applications such as bags, shoes (upper shoe), belts, etc., as well as for upholstery. By promoting aerial mycelium development, the thickness of the textiles manufactured as described herein may be between 1 to 2 mm, depending on their application.

The humidity barrier may be applied in any of these textiles in order to avoid excessive drying (that causes depletion of the mechanical properties) or, on the contrary, excessive wetting that could cause microbiological contamination (bacteria or fungi from the environment), accelerating the product's decomposition. The humidity barriers described herein may have a thickness of >10 and <100 microns. More than 100 microns may cause stiffness in the final product, and below 10 microns, there may be an insufficient barrier effect.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

As used herein, the terms "fungal-based textile", "fungal-based textiles", "mycotextile" or "mycotextiles" may be interchangeably used to refer to a biotextile made from fungal mycelium that colonize externally, internally, and within a scaffold (reinforced or not with organic or inorganic nanofillers, such as glass fiber, carbon fiber or cotton interlining, between others), that may have been previously activated to increase the affinity among the fungal hyphae and the vegetal layer, and which may be subsequently cross-linked using nanoparticles, as described herein, which may further enhance the mechanical properties of the material. These biotextiles may be internally moisturized, dyed, and coated with a humidity barrier that may allow both protection against humidity and wear, and a wide range of functionalities converting the final product into a functional and smart mycotextile.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively, or in combination, the processor can be configured to combine one or more steps of one or more methods as disclosed herein.

When a feature or element is herein referred to as being "on" another feature or element, it can be directly on the other feature or element, or intervening features and/or elements may also be present. In contrast, when a feature or element is referred to as being "directly on" another feature or element, no intervening features or elements are present. It will also be understood that when a feature or element is referred to as being "connected", "attached," or "coupled" to another feature or element, it can be directly connected, attached or coupled to the other feature or element or intervening features or elements may be present. In contrast, when a feature or element is referred to as being "directly connected", "directly attached," or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed of "adjacent" another feature may have portions that overlap or underlie the adjacent feature.

The terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal," and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise" and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that throughout the application, data is provided in a number of different formats and that this data represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not explicitly described herein, will be apparent to those of skill in the art upon reviewing the above description.

What is claimed is:

1. A mycotextile comprising:
   a support scaffold layer;
   a first crosslinked mycelium layer extending adjacent to a first side of the support scaffold layer, and a second crosslinked mycelium layer extending adjacent to a second side of the support scaffold layer; and
   a plurality of ceramic nanoparticles agglomerated along a surface of hyphae structures within the first and second crosslinked mycelium layers, wherein the plurality of nanoparticles are functionalized with an organic functionalizing agent adsorbed onto a surface of the ceramic nanoparticles to crosslink chitin and/or chitosan within hyphae of the first crosslinked mycelium layer and the second crosslinked mycelium layer.

2. The mycotextile of claim 1, wherein the plurality of nanoparticles are functionalized nanoparticles comprising one or more polyphosphate groups coupled to a surface of the nanoparticles, one or more amino groups coupled to a surface of the nanoparticles, one or more epoxy groups coupled to the surface of the nanoparticles, one or more acrylic groups coupled to the surface of the nanoparticles, one or more isocyanate groups coupled to the surface of the nanoparticles, one or more vinylic groups coupled to the surface of the nanoparticles.

3. The mycotextile of claim 2, wherein the functionalized nanoparticles comprise a functionalizing agent selected from the group consisting of: 3-(Trihydroxysilyl)propyl methylphosphonate, sodium polyphosphate, phosphorous acid, phosphoric acid.

4. The mycotextile of claim 2, wherein the functionalizing agents to achieve the terminal functional groups are selected form the group consisting of: polyethylenimines, aminosilane, 3-Glycidyloxypropyl)trimethoxysilane, 3-methacryloxypropyltrimethoxysilane, 3-(triethoxysilyl)propyl isocyanate, vinyltrimethoxysilane, hexadecyltrimethoxysilane, chloro(dimethyl)octylsilane.

5. The mycotextile of claim 1, wherein the plurality of nanoparticles within the hyphae of the first crosslinked mycelium layer comprise between 0.1% and 5% by weight of the mycotextile.

6. The mycotextile of claim 1, wherein the average diameter of the hyphae in the first mycelium layer and the second mycelium layer is greater than about 1 µm.

7. The mycotextile of claim 1, wherein a chitin fraction of the first crosslinked mycelium layer and the second crosslinked mycelium layer is 45 to 80% and wherein the first crosslinked mycelium layer and the second crosslinked mycelium layer are enriched for acetamide and/or amide groups.

8. The mycotextile of claim 1, wherein the scaffold layer comprises one or more reinforcement of: a glass fiber or, a carbon fiber or, a carbon nanofiber or an aramid fiber.

9. The mycotextile of claim 1, wherein the scaffold layer comprises a vegetable fiber layer.

10. The mycotextile of claim 1, wherein the scaffold layer comprises a reinforced chemically activated cotton layer.

11. The mycotextile of claim 1, further comprising a first external humidity barrier on an outer surface of the first crosslinked mycelium layer and a second external humidity barrier on an outer surface of the second crosslinked mycelium layer.

12. The mycotextile of claim 11, wherein the first external humidity barrier and the second external humidity barrier comprise a soluble biodegradable polymer between 1 to 5 wt. %, a plasticizer, and water.

13. A mycotextile comprising:
    a support scaffold layer;
    a first crosslinked mycelium layer comprising a first hyphal network, wherein hyphae of the first hyphal network have an average diameter of 1 µm or greater, the first crosslinked mycelium layer extending adjacent to a first side of the support scaffold layer;
    a second crosslinked mycelium layer comprising a second hyphal network, wherein hyphae of the second hyphal network have an average diameter of 1 µm or greater, the second crosslinked mycelium layer extending adjacent to a second side of the support scaffold layer; and
    a plurality of ceramic nanoparticles agglomerated along a surface of hyphae structures within the first and second crosslinked mycelium layers, wherein a surface of each nanoparticle of the plurality of nanoparticles is functionalized with an organic functionalizing agent adsorbed onto a surface of the ceramic nanoparticles to crosslink chitin within the hyphae of the first crosslinked mycelium layer and the second crosslinked mycelium layer.

14. The mycotextile of claim 13, wherein the plurality of nanoparticles are functionalized nanoparticles comprising one or more polyphosphate groups coupled to a surface of the nanoparticles, one or more amino groups coupled to a surface of the nanoparticles, one or more epoxy groups coupled to the surface of the nanoparticles, one or more acrylic groups coupled to the surface of the nanoparticles, one or more isocyanate groups coupled to the surface of the nanoparticles, one or more vinylic groups coupled to the surface of the nanoparticles.

15. The mycotextile of claim 14, wherein the functionalized nanoparticles comprise one or more polyphosphate groups bound to a surface of the nanoparticles with a functionalizing agent selected from the group consisting of: 3-(Trihydroxysilyl)propyl methylphosphonate, sodium polyphosphate, phosphorous acid, phosphoric acid.

16. The mycotextile of claim 14, wherein the functionalizing agents to achieve the terminal functional groups are selected form the group consisting of: polyethylenimines, aminosilane, 3-Glycidyloxypropyl)trimethoxysilane, 3-methacryloxypropyltrimethoxysilane, 3-(triethoxysilyl) propyl isocyanate, vinyltrimethoxysilane, hexadecyltrimethoxysilane, chloro(dimethyl)octylsilane.

17. The mycotextile of claim 13, wherein the plurality of nanoparticles within the to hyphae of the first crosslinked mycelium layer comprise between 0.1% and 5% by weight of the first crosslinked mycelium layer.

18. The mycotextile of claim 13, wherein a chitin fraction of the first crosslinked mycelium layer and the second crosslinked mycelium layer is 45 to 80% and wherein the first crosslinked mycelium layer and the second crosslinked mycelium layer are enriched for acetamide and/or amide groups.

19. The mycotextile of claim 13, wherein the scaffold layer comprises one or more of: a glass fiber or, a carbon fiber or, a carbon nanofiber or polyaramid fiber, or a cotton interlining.

20. The mycotextile of claim 13, wherein the scaffold layer comprises a vegetable fiber layer.

21. The mycotextile of claim 13, wherein the scaffold layer comprises a chemically activated cotton layer.

22. The mycotextile of claim 13, wherein the first crosslinked mycelium layer is thicker than the second crosslinked mycelium layer.

23. The mycotextile of claim 13, further comprising a first external humidity barrier on an outer surface of the first crosslinked mycelium layer and a second external humidity barrier on an outer surface of the second crosslinked mycelium layer.

24. The mycotextile of claim 23, wherein the first external humidity barrier and the second external humidity barrier comprise 1 to 5 wt. % of a polymer, a plasticizer and water.

25. A mycotextile comprising:
a support scaffold layer;
a crosslinked mycelium layer extending adjacent to at least a first side of the support scaffold layer;
an external humidity barrier on an outer surface of the crosslinked mycelium layer; and
a plurality of ceramic nanoparticles agglomerated along a surface of hyphae structures within the crosslinked mycelium layer, wherein a surface of each nanoparticle of the plurality of nanoparticles is functionalized with an organic functionalizing agent adsorbed onto a surface of the ceramic nanoparticles to crosslink chitin and/or chitosan within hyphae of the crosslinked mycelium layer.

* * * * *